(12) United States Patent
Brauker et al.

(10) Patent No.: US 8,882,741 B2
(45) Date of Patent: Nov. 11, 2014

(54) INTEGRATED DELIVERY DEVICE FOR CONTINUOUS GLUCOSE SENSOR

(75) Inventors: James H. Brauker, Addison, MI (US);
Mark A. Tapsak, Orangeville, PA (US);
Sean T. Saint, San Diego, CA (US);
Apurv U. Kamath, San Diego, CA (US); Paul V. Neale, San Diego, CA (US); Peter C. Simpson, Encinitas, CA (US); Michael Robert Mensinger, San Diego, CA (US); Dubravka Markovic, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 170 days.

(21) Appl. No.: 13/460,219

(22) Filed: Apr. 30, 2012

(65) Prior Publication Data

US 2012/0220979 A1 Aug. 30, 2012

Related U.S. Application Data

(60) Continuation of application No. 13/180,396, filed on Jul. 11, 2011, now Pat. No. 8,460,231, which is a continuation of application No. 12/536,852, filed on Aug. 6, 2009, now Pat. No. 7,976,492, which is a division of application No. 10/789,359, filed on Feb. 26, 2004, now Pat. No. 7,591,801.

(51) Int. Cl.
*A61M 31/00* (2006.01)
*A61M 37/00* (2006.01)
*A61B 5/00* (2006.01)
*A61M 5/315* (2006.01)
*G06F 19/00* (2011.01)
*A61B 5/145* (2006.01)
*A61B 5/1486* (2006.01)

(52) U.S. Cl.
CPC .... *A61M 5/31525* (2013.01); *A61B 2560/0443* (2013.01); *A61B 5/4839* (2013.01); *A61B 5/1486* (2013.01); *A61B 5/0002* (2013.01); *G06F 19/3406* (2013.01); *G06F 19/3468* (2013.01); *A61B 5/14532* (2013.01)
USPC ............... 604/503; 604/504; 604/66; 604/31

(58) Field of Classification Search
USPC .................. 604/31, 65–67, 503–504
See application file for complete search history.

(56) References Cited

U.S. PATENT DOCUMENTS 2,719,797 A 10/1955 Rosenblatt et al.
3,219,533 A 11/1965 Mullins
(Continued)

FOREIGN PATENT DOCUMENTS

EP 0 098 592 1/1984
EP 0 127 958 12/1984
(Continued)

OTHER PUBLICATIONS

EPO Communication dated Jan. 28, 2011 for EP 05723951.9, filed Feb. 24, 2005.

(Continued)

*Primary Examiner* — Rebecca E Eisenberg
(74) *Attorney, Agent, or Firm* — Knobbe Martens Olson & Bear, LLP.

(57) ABSTRACT

Systems and methods for integrating a continuous glucose sensor, including a receiver, a medicament delivery device, and optionally a single point glucose monitor are provided. Manual integrations provide for a physical association between the devices wherein a user (for example, patient or doctor) manually selects the amount, type, and/or time of delivery. Semi-automated integration of the devices includes integrations wherein an operable connection between the integrated components aids the user (for example, patient or doctor) in selecting, inputting, calculating, or validating the amount, type, or time of medicament delivery of glucose values, for example, by transmitting data to another component and thereby reducing the amount of user input required. Automated integration between the devices includes integrations wherein an operable connection between the integrated components provides for full control of the system without required user interaction.

17 Claims, 10 Drawing Sheets

(56) References Cited

U.S. PATENT DOCUMENTS

| | | | |
|---|---|---|---|
| 3,780,727 A | 12/1973 | King | |
| 3,837,339 A | 9/1974 | Aisenberg et al. | |
| 3,898,984 A | 8/1975 | Mandel et al. | |
| 3,929,971 A | 12/1975 | Roy | |
| 3,943,918 A | 3/1976 | Lewis | |
| 3,957,613 A | 5/1976 | Macur | |
| 3,979,274 A | 9/1976 | Newman | |
| 4,076,656 A | 2/1978 | White et al. | |
| 4,240,438 A | 12/1980 | Updike et al. | |
| 4,245,634 A | 1/1981 | Albisser et al. | |
| 4,253,469 A | 3/1981 | Aslan | |
| 4,403,984 A | 9/1983 | Ash et al. | |
| 4,415,666 A | 11/1983 | D'Orazio et al. | |
| 4,431,004 A | 2/1984 | Bessman et al. | |
| 4,436,094 A | 3/1984 | Cerami | |
| 4,454,295 A | 6/1984 | Wittmann et al. | |
| 4,494,950 A | 1/1985 | Fischell | |
| 4,506,680 A | 3/1985 | Stokes | |
| 4,535,786 A | 8/1985 | Kater | |
| 4,554,927 A | 11/1985 | Fussell | |
| 4,577,642 A | 3/1986 | Stokes | |
| 4,583,976 A | 4/1986 | Ferguson | |
| RE32,361 E | 2/1987 | Duggan | |
| 4,671,288 A | 6/1987 | Gough | |
| 4,680,268 A | 7/1987 | Clark, Jr. | |
| 4,703,756 A | 11/1987 | Gough et al. | |
| 4,711,251 A | 12/1987 | Stokes | |
| 4,721,677 A | 1/1988 | Clark | |
| 4,731,726 A | 3/1988 | Allen, III | |
| 4,757,022 A | 7/1988 | Shults et al. | |
| 4,759,828 A | 7/1988 | Young et al. | |
| 4,781,798 A | 11/1988 | Gough | |
| 4,805,624 A | 2/1989 | Yao et al. | |
| 4,805,625 A | 2/1989 | Wyler | |
| 4,807,632 A | 2/1989 | Liess et al. | |
| 4,831,070 A | 5/1989 | McInally et al. | |
| 4,849,458 A | 7/1989 | Reed et al. | |
| 4,852,573 A | 8/1989 | Kennedy | |
| 4,890,620 A | 1/1990 | Gough | |
| 4,927,516 A | 5/1990 | Yamaguchi et al. | |
| 4,950,246 A | 8/1990 | Muller | |
| 4,953,552 A | 9/1990 | DeMarzo | |
| 4,975,636 A | 12/1990 | Desautels | |
| 4,986,671 A | 1/1991 | Sun et al. | |
| 4,988,341 A | 1/1991 | Columbus et al. | |
| 4,994,167 A | 2/1991 | Shults et al. | |
| 5,002,572 A | 3/1991 | Picha | |
| 5,019,974 A | 5/1991 | Beckers | |
| 5,030,333 A | 7/1991 | Clark, Jr. | |
| 5,050,612 A | 9/1991 | Matsumura | |
| 5,068,536 A | 11/1991 | Rosenthal | |
| 5,077,476 A | 12/1991 | Rosenthal | |
| 5,101,814 A | 4/1992 | Palti | |
| 5,108,819 A | 4/1992 | Heller et al. | |
| 5,137,028 A | 8/1992 | Nishimura | |
| 5,140,985 A | 8/1992 | Schroeder et al. | |
| 5,160,418 A | 11/1992 | Mullen | |
| 5,165,407 A | 11/1992 | Wilson et al. | |
| 5,198,771 A | 3/1993 | Fidler et al. | |
| 5,243,983 A | 9/1993 | Tarr et al. | |
| 5,262,305 A | 11/1993 | Heller et al. | |
| 5,264,104 A | 11/1993 | Gregg et al. | |
| 5,269,891 A | 12/1993 | Colin | |
| 5,284,570 A | 2/1994 | Savage et al. | |
| 5,299,571 A | 4/1994 | Mastrototaro | |
| 5,307,263 A | 4/1994 | Brown | |
| 5,314,471 A | 5/1994 | Brauker et al. | |
| 5,316,008 A | 5/1994 | Suga et al. | |
| 5,322,063 A | 6/1994 | Allen et al. | |
| 5,324,322 A | 6/1994 | Grill, Jr. et al. | |
| 5,330,634 A | 7/1994 | Wong et al. | |
| 5,331,555 A | 7/1994 | Hashimoto et al. | |
| 5,372,133 A | 12/1994 | Hogen Esch | |
| 5,376,070 A | 12/1994 | Purvis et al. | |
| 5,390,671 A | 2/1995 | Lord et al. | |
| 5,391,250 A | 2/1995 | Cheney, II et al. | |
| 5,429,735 A | 7/1995 | Johnson et al. | |
| 5,431,160 A | 7/1995 | Wilkins | |
| 5,448,992 A | 9/1995 | Kuperschmidt | |
| 5,462,051 A | 10/1995 | Oka et al. | |
| 5,462,064 A | 10/1995 | D'Angelo et al. | |
| 5,466,356 A | 11/1995 | Schneider et al. | |
| 5,474,552 A | 12/1995 | Palti | |
| 5,482,473 A | 1/1996 | Lord et al. | |
| 5,494,562 A | 2/1996 | Maley et al. | |
| 5,497,772 A | 3/1996 | Schulman et al. | |
| 5,507,288 A | 4/1996 | Bocker et al. | |
| 5,508,203 A | 4/1996 | Fuller et al. | |
| 5,513,636 A | 5/1996 | Palti | |
| 5,518,601 A | 5/1996 | Foos et al. | |
| 5,527,288 A | 6/1996 | Gross et al. | |
| 5,531,679 A | 7/1996 | Schulman et al. | |
| 5,531,878 A | 7/1996 | Vadgama et al. | |
| 5,540,828 A | 7/1996 | Yacynych | |
| 5,553,616 A | 9/1996 | Ham et al. | |
| 5,568,806 A | 10/1996 | Cheney, II et al. | |
| 5,569,186 A | 10/1996 | Lord et al. | |
| 5,582,184 A | 12/1996 | Erickson et al. | |
| 5,584,813 A | 12/1996 | Livingston et al. | |
| 5,586,553 A | 12/1996 | Halili et al. | |
| 5,589,133 A | 12/1996 | Suzuki | |
| 5,653,863 A | 8/1997 | Genshaw et al. | |
| 5,660,163 A | 8/1997 | Schulman et al. | |
| 5,665,065 A | 9/1997 | Colman et al. | |
| 5,674,289 A | 10/1997 | Fournier et al. | |
| 5,695,623 A | 12/1997 | Michel et al. | |
| 5,696,314 A | 12/1997 | McCaffrey et al. | |
| 5,711,861 A | 1/1998 | Ward et al. | |
| 5,730,654 A | 3/1998 | Brown | |
| 5,743,262 A | 4/1998 | Lepper, Jr. et al. | |
| 5,781,455 A | 7/1998 | Hyodo et al. | |
| 5,795,774 A | 8/1998 | Matsumoto et al. | |
| 5,800,420 A | 9/1998 | Gross et al. | |
| 5,806,517 A | 9/1998 | Gerhardt et al. | |
| 5,807,375 A | 9/1998 | Gross et al. | |
| 5,814,599 A | 9/1998 | Mitragotri et al. | |
| 5,820,622 A | 10/1998 | Gross et al. | |
| 5,822,715 A | 10/1998 | Worthington et al. | |
| 5,836,887 A | 11/1998 | Oka et al. | |
| 5,848,991 A | 12/1998 | Gross et al. | |
| 5,861,019 A | 1/1999 | Sun et al. | |
| 5,871,514 A | 2/1999 | Wiklund et al. | |
| 5,897,578 A | 4/1999 | Wiklund et al. | |
| 5,899,855 A | 5/1999 | Brown | |
| 5,913,998 A | 6/1999 | Butler et al. | |
| 5,914,026 A | 6/1999 | Blubaugh, Jr. et al. | |
| 5,919,215 A | 7/1999 | Wiklund et al. | |
| 5,919,216 A | 7/1999 | Houben et al. | |
| 5,925,021 A | 7/1999 | Castellano et al. | |
| 5,931,814 A | 8/1999 | Alex et al. | |
| 5,954,643 A | 9/1999 | Van Antwerp et al. | |
| 5,957,854 A | 9/1999 | Besson et al. | |
| 5,961,451 A | 10/1999 | Reber et al. | |
| 5,964,993 A | 10/1999 | Blubaugh et al. | |
| 5,965,380 A | 10/1999 | Heller et al. | |
| 5,971,922 A | 10/1999 | Arita et al. | |
| 5,976,085 A | 11/1999 | Kimball et al. | |
| 5,997,501 A | 12/1999 | Gross et al. | |
| 6,011,984 A | 1/2000 | Van Antwerp et al. | |
| 6,016,448 A | 1/2000 | Busacker et al. | |
| 6,027,445 A | 2/2000 | Von Bahr | |
| 6,036,924 A | 3/2000 | Simons et al. | |
| 6,049,727 A | 4/2000 | Crothall | |
| 6,059,946 A | 5/2000 | Yukawa et al. | |
| 6,081,735 A | 6/2000 | Diab et al. | |
| 6,083,523 A | 7/2000 | Dionne et al. | |
| 6,091,975 A | 7/2000 | Daddona et al. | |
| 6,093,172 A | 7/2000 | Funderburk et al. | |
| 6,107,083 A | 8/2000 | Collins et al. | |
| 6,117,290 A | 9/2000 | Say et al. | |
| 6,122,536 A | 9/2000 | Sun et al. | |
| 6,123,827 A | 9/2000 | Wong et al. | |
| 6,129,891 A | 10/2000 | Rolander et al. | |
| 6,135,978 A | 10/2000 | Houben et al. | |

(56) References Cited

U.S. PATENT DOCUMENTS

| | | |
|---|---|---|
| 6,144,869 A | 11/2000 | Berner et al. |
| 6,162,611 A | 12/2000 | Heller et al. |
| 6,163,720 A | 12/2000 | Gyory et al. |
| 6,169,155 B1 | 1/2001 | Alvarez et al. |
| 6,175,752 B1 | 1/2001 | Say et al. |
| 6,192,891 B1 | 2/2001 | Gravel et al. |
| 6,201,980 B1 | 3/2001 | Darrow et al. |
| 6,201,993 B1 | 3/2001 | Kruse et al. |
| 6,212,416 B1 | 4/2001 | Ward et al. |
| 6,212,424 B1 | 4/2001 | Robinson |
| 6,223,083 B1 | 4/2001 | Rosar |
| 6,230,059 B1 | 5/2001 | Duffin |
| 6,233,471 B1 | 5/2001 | Berner et al. |
| 6,234,964 B1 * | 5/2001 | Iliff .............................. 600/300 |
| 6,248,067 B1 | 6/2001 | Causey, III et al. |
| 6,256,522 B1 | 7/2001 | Schultz |
| 6,259,937 B1 | 7/2001 | Schulman et al. |
| 6,299,578 B1 | 10/2001 | Kurnik et al. |
| 6,299,583 B1 | 10/2001 | Eggers et al. |
| 6,302,855 B1 | 10/2001 | Lav et al. |
| 6,309,351 B1 | 10/2001 | Kurnik et al. |
| 6,309,884 B1 | 10/2001 | Cooper et al. |
| 6,312,388 B1 | 11/2001 | Marcovecchio et al. |
| 6,329,161 B1 | 12/2001 | Heller et al. |
| 6,329,929 B1 | 12/2001 | Weijand et al. |
| 6,330,464 B1 | 12/2001 | Colvin, Jr. et al. |
| 6,343,225 B1 | 1/2002 | Clark, Jr. |
| 6,356,776 B1 | 3/2002 | Berner et al. |
| 6,370,941 B2 | 4/2002 | Nakamura |
| 6,379,301 B1 | 4/2002 | Worthington et al. |
| 6,406,066 B1 | 6/2002 | Uegane |
| 6,424,847 B1 | 7/2002 | Mastrototaro et al. |
| 6,461,496 B1 | 10/2002 | Feldman et al. |
| 6,464,849 B1 | 10/2002 | Say et al. |
| 6,466,810 B1 | 10/2002 | Ward et al. |
| 6,471,689 B1 | 10/2002 | Joseph et al. |
| 6,477,392 B1 | 11/2002 | Honigs et al. |
| 6,477,395 B2 | 11/2002 | Schulman et al. |
| 6,484,046 B1 | 11/2002 | Say et al. |
| 6,512,939 B1 | 1/2003 | Colvin et al. |
| 6,526,298 B1 | 2/2003 | Khalil et al. |
| 6,527,729 B1 | 3/2003 | Turcott |
| 6,544,212 B2 * | 4/2003 | Galley et al. .................. 604/31 |
| 6,546,268 B1 | 4/2003 | Ishikawa et al. |
| 6,549,796 B2 * | 4/2003 | Sohrab ........................ 600/345 |
| 6,551,496 B1 | 4/2003 | Moles et al. |
| 6,558,320 B1 | 5/2003 | Causey, III et al. |
| 6,558,351 B1 | 5/2003 | Steil et al. |
| 6,558,955 B1 | 5/2003 | Kristal et al. |
| 6,562,001 B2 | 5/2003 | Lebel et al. |
| 6,565,509 B1 | 5/2003 | Say et al. |
| 6,571,128 B2 | 5/2003 | Lebel et al. |
| 6,572,545 B2 | 6/2003 | Knobbe et al. |
| 6,574,490 B2 | 6/2003 | Abbink et al. |
| 6,577,899 B2 | 6/2003 | Lebel et al. |
| 6,579,498 B1 | 6/2003 | Eglise |
| 6,579,690 B1 | 6/2003 | Bonnecaze et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,595,919 B2 | 7/2003 | Berner et al. |
| 6,605,072 B2 | 8/2003 | Struys et al. |
| 6,618,934 B1 | 9/2003 | Feldman et al. |
| 6,620,138 B1 | 9/2003 | Marrgi et al. |
| 6,635,014 B2 | 10/2003 | Starkweather et al. |
| 6,648,821 B2 | 11/2003 | Lebel et al. |
| 6,673,022 B1 | 1/2004 | Bobo et al. |
| 6,699,188 B2 | 3/2004 | Wessel |
| 6,702,857 B2 | 3/2004 | Brauker et al. |
| 6,702,972 B1 | 3/2004 | Markle |
| 6,740,072 B2 | 5/2004 | Starkweather et al. |
| 6,741,877 B1 | 5/2004 | Shults et al. |
| 6,743,635 B2 | 6/2004 | Neel et al. |
| 6,750,055 B1 | 6/2004 | Connelly et al. |
| 6,832,200 B2 | 12/2004 | Greeven et al. |
| 6,869,413 B2 | 3/2005 | Langley et al. |
| 6,875,195 B2 | 4/2005 | Choi |
| 6,895,263 B2 | 5/2005 | Shin et al. |
| 6,925,393 B1 | 8/2005 | Kalatz et al. |
| 6,936,006 B2 | 8/2005 | Sabra |
| 6,936,029 B2 * | 8/2005 | Mann et al. .................. 604/131 |
| 6,965,791 B1 | 11/2005 | Hitchcock et al. |
| 7,025,743 B2 | 4/2006 | Mann et al. |
| 7,029,444 B2 | 4/2006 | Shin et al. |
| 7,058,437 B2 | 6/2006 | Buse et al. |
| 7,060,059 B2 | 6/2006 | Keith et al. |
| 7,081,195 B2 | 7/2006 | Simpson et al. |
| 7,162,290 B1 | 1/2007 | Levin |
| 7,169,289 B2 | 1/2007 | Schulein et al. |
| 7,225,535 B2 | 6/2007 | Feldman et al. |
| 7,229,288 B2 | 6/2007 | Stuart et al. |
| 7,261,690 B2 | 8/2007 | Teller et al. |
| 7,267,665 B2 | 9/2007 | Steil et al. |
| 7,276,029 B2 | 10/2007 | Goode et al. |
| 7,278,983 B2 * | 10/2007 | Ireland et al. .................. 604/66 |
| 7,282,029 B1 | 10/2007 | Poulsen et al. |
| 7,291,114 B2 | 11/2007 | Mault |
| 7,344,500 B2 | 3/2008 | Talbot et al. |
| 7,354,420 B2 | 4/2008 | Steil et al. |
| 7,359,723 B2 | 4/2008 | Jones |
| 7,367,942 B2 | 5/2008 | Grage et al. |
| 7,402,153 B2 | 7/2008 | Steil et al. |
| 7,417,164 B2 | 8/2008 | Suri |
| 7,426,408 B2 | 9/2008 | DeNuzzio et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,618,368 B2 | 11/2009 | Brown |
| 7,624,028 B1 | 11/2009 | Brown |
| 7,640,032 B2 | 12/2009 | Jones |
| 7,640,048 B2 | 12/2009 | Dobbles et al. |
| 7,647,237 B2 * | 1/2010 | Malave et al. .................. 705/3 |
| 7,657,297 B2 | 2/2010 | Simpson et al. |
| 7,901,394 B2 | 3/2011 | Ireland et al. |
| 7,946,985 B2 | 5/2011 | Mastrototaro et al. |
| 8,512,276 B2 | 8/2013 | Talbot et al. |
| 2001/0007950 A1 * | 7/2001 | North et al. .................. 607/59 |
| 2001/0051768 A1 | 12/2001 | Schulman et al. |
| 2002/0019022 A1 | 2/2002 | Dunn et al. |
| 2002/0042090 A1 | 4/2002 | Heller et al. |
| 2002/0043471 A1 | 4/2002 | Ikeda et al. |
| 2002/0045808 A1 * | 4/2002 | Ford et al. .................. 600/347 |
| 2002/0065453 A1 * | 5/2002 | Lesho et al. .................. 600/347 |
| 2002/0068860 A1 | 6/2002 | Clark, Jr. |
| 2002/0099282 A1 | 7/2002 | Knobbe et al. |
| 2002/0111547 A1 | 8/2002 | Knobbe et al. |
| 2002/0155615 A1 | 10/2002 | Novikov et al. |
| 2002/0188185 A1 | 12/2002 | Sohrab |
| 2002/0198513 A1 | 12/2002 | Lebel et al. |
| 2003/0004432 A1 | 1/2003 | Assenheimer |
| 2003/0006669 A1 | 1/2003 | Pei et al. |
| 2003/0023317 A1 | 1/2003 | Brauker et al. |
| 2003/0028089 A1 | 2/2003 | Galley et al. |
| 2003/0032874 A1 | 2/2003 | Rhodes et al. |
| 2003/0050546 A1 | 3/2003 | Desai et al. |
| 2003/0060753 A1 | 3/2003 | Starkweather et al. |
| 2003/0060765 A1 | 3/2003 | Campbell et al. |
| 2003/0070548 A1 | 4/2003 | Clausen |
| 2003/0076082 A1 | 4/2003 | Morgan et al. |
| 2003/0078560 A1 | 4/2003 | Miller et al. |
| 2003/0097082 A1 | 5/2003 | Purdy et al. |
| 2003/0114836 A1 | 6/2003 | Estes et al. |
| 2003/0120152 A1 | 6/2003 | Omiya |
| 2003/0125612 A1 | 7/2003 | Fox et al. |
| 2003/0125613 A1 | 7/2003 | Enegren et al. |
| 2003/0130616 A1 | 7/2003 | Steil et al. |
| 2003/0187338 A1 | 10/2003 | Say et al. |
| 2003/0208113 A1 | 11/2003 | Mault et al. |
| 2003/0212317 A1 | 11/2003 | Kovatchev et al. |
| 2003/0235817 A1 | 12/2003 | Bartkowiak et al. |

(56) References Cited

U.S. PATENT DOCUMENTS

| | | |
|---|---|---|
| 2004/0011671 A1 | 1/2004 | Shults et al. |
| 2004/0040840 A1 | 3/2004 | Mao et al. |
| 2004/0044272 A1* | 3/2004 | Moerman et al. ............ 600/300 |
| 2004/0045879 A1 | 3/2004 | Shults et al. |
| 2004/0106857 A1 | 6/2004 | Gough |
| 2004/0122297 A1* | 6/2004 | Stahmann et al. ............ 600/300 |
| 2004/0143173 A1 | 7/2004 | Reghabi et al. |
| 2004/0152187 A1 | 8/2004 | Haight et al. |
| 2004/0152622 A1 | 8/2004 | Keith et al. |
| 2004/0162678 A1 | 8/2004 | Hetzel et al. |
| 2004/0173472 A1 | 9/2004 | Jung et al. |
| 2004/0186362 A1 | 9/2004 | Brauker et al. |
| 2004/0199059 A1 | 10/2004 | Brauker et al. |
| 2004/0204687 A1 | 10/2004 | Mogensen et al. |
| 2004/0254433 A1 | 12/2004 | Bandis |
| 2005/0010265 A1 | 1/2005 | Baru Fassio et al. |
| 2005/0027180 A1 | 2/2005 | Goode et al. |
| 2005/0027182 A1 | 2/2005 | Siddiqui et al. |
| 2005/0049472 A1 | 3/2005 | Manda et al. |
| 2005/0096519 A1 | 5/2005 | DeNuzzio et al. |
| 2005/0101847 A1 | 5/2005 | Routt et al. |
| 2005/0113653 A1 | 5/2005 | Fox et al. |
| 2005/0113744 A1* | 5/2005 | Donoghue et al. ............ 604/66 |
| 2005/0115832 A1 | 6/2005 | Simpson et al. |
| 2005/0121322 A1 | 6/2005 | Say |
| 2005/0139489 A1 | 6/2005 | Davies et al. |
| 2005/0143635 A1 | 6/2005 | Kamath et al. |
| 2005/0143675 A1 | 6/2005 | Neel et al. |
| 2005/0154271 A1 | 7/2005 | Rasdal et al. |
| 2005/0177398 A1 | 8/2005 | Watanabe et al. |
| 2005/0182451 A1 | 8/2005 | Griffin et al. |
| 2005/0192557 A1 | 9/2005 | Brauker et al. |
| 2005/0203360 A1 | 9/2005 | Brauker et al. |
| 2005/0211571 A1 | 9/2005 | Schulein et al. |
| 2005/0215872 A1 | 9/2005 | Berner et al. |
| 2005/0239154 A1 | 10/2005 | Feldman et al. |
| 2005/0245904 A1 | 11/2005 | Estes et al. |
| 2005/0261563 A1 | 11/2005 | Zhou et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0079809 A1 | 4/2006 | Goldberger et al. |
| 2006/0100588 A1 | 5/2006 | Brunnberg et al. |
| 2006/0173406 A1 | 8/2006 | Hayes et al. |
| 2006/0183984 A1 | 8/2006 | Dobbles et al. |
| 2006/0183985 A1 | 8/2006 | Brister et al. |
| 2006/0222566 A1 | 10/2006 | Brauker et al. |
| 2006/0258929 A1 | 11/2006 | Goode et al. |
| 2007/0027385 A1 | 2/2007 | Brister et al. |
| 2007/0038044 A1 | 2/2007 | Dobbles et al. |
| 2007/0049873 A1 | 3/2007 | Hansen et al. |
| 2007/0066956 A1 | 3/2007 | Finkel |
| 2007/0100222 A1 | 5/2007 | Mastrototaro et al. |
| 2007/0106135 A1 | 5/2007 | Sloan et al. |
| 2007/0112298 A1 | 5/2007 | Mueller et al. |
| 2007/0173761 A1 | 7/2007 | Kanderian et al. |
| 2007/0179434 A1 | 8/2007 | Weinert et al. |
| 2007/0203410 A1 | 8/2007 | Say et al. |
| 2007/0208246 A1 | 9/2007 | Brauker et al. |
| 2007/0213610 A1 | 9/2007 | Say et al. |
| 2007/0225579 A1 | 9/2007 | Lucassen et al. |
| 2007/0293742 A1* | 12/2007 | Simonsen et al. ............ 600/316 |
| 2008/0033254 A1 | 2/2008 | Kamath et al. |
| 2008/0097289 A1 | 4/2008 | Steil et al. |
| 2008/0183061 A1 | 7/2008 | Goode et al. |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0188731 A1 | 8/2008 | Brister et al. |
| 2008/0194935 A1 | 8/2008 | Brister et al. |
| 2008/0194937 A1 | 8/2008 | Goode et al. |
| 2008/0210557 A1 | 9/2008 | Heller et al. |
| 2008/0214915 A1 | 9/2008 | Brister et al. |
| 2008/0262469 A1 | 10/2008 | Brister et al. |
| 2008/0269723 A1 | 10/2008 | Mastrototaro et al. |
| 2008/0305009 A1 | 12/2008 | Gamsey et al. |
| 2008/0305506 A1 | 12/2008 | Suri |
| 2008/0306433 A1 | 12/2008 | Cesaroni |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0018418 A1 | 1/2009 | Markle et al. |
| 2009/0018426 A1 | 1/2009 | Markle et al. |
| 2009/0061528 A1 | 3/2009 | Suri |
| 2009/0062635 A1 | 3/2009 | Brauker et al. |
| 2009/0076360 A1 | 3/2009 | Brister et al. |
| 2009/0076361 A1 | 3/2009 | Kamath et al. |
| 2009/0081803 A1 | 3/2009 | Gamsey et al. |
| 2009/0099434 A1 | 4/2009 | Liu et al. |
| 2009/0124877 A1 | 5/2009 | Goode, Jr. et al. |
| 2009/0124878 A1 | 5/2009 | Goode, Jr. et al. |
| 2009/0156924 A1 | 6/2009 | Shariati et al. |
| 2009/0177143 A1 | 7/2009 | Markle et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0264719 A1 | 10/2009 | Markle et al. |
| 2009/0264856 A1 | 10/2009 | Lebel et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0022855 A1 | 1/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036224 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0076283 A1 | 3/2010 | Simpson et al. |
| 2010/0081908 A1 | 4/2010 | Dobbles et al. |
| 2010/0161269 A1 | 6/2010 | Kamath et al. |
| 2010/0179401 A1 | 7/2010 | Rasdal et al. |
| 2011/0201910 A1 | 8/2011 | Rasdal et al. |
| 2011/0270158 A1 | 11/2011 | Brauker et al. |
| 2012/0186581 A1 | 7/2012 | Brauker et al. |
| 2012/0190953 A1 | 7/2012 | Brauker et al. |

(56) References Cited

U.S. PATENT DOCUMENTS

| | | |
|---|---|---|
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0227737 A1 | 9/2012 | Mastrototaro et al. |
| 2012/0238852 A1 | 9/2012 | Brauker et al. |
| 2012/0259278 A1 | 10/2012 | Hayes et al. |
| 2012/0296311 A1 | 11/2012 | Brauker et al. |

FOREIGN PATENT DOCUMENTS

| | | |
|---|---|---|
| EP | 0 320 109 | 6/1989 |
| EP | 0 353 328 | 2/1990 |
| EP | 0 390 390 | 10/1990 |
| EP | 0 441 394 | 8/1991 |
| EP | 0 563 795 | 10/1993 |
| EP | 0 729 366 | 9/1996 |
| EP | 0 817 809 | 1/1998 |
| EP | 0 838 230 | 4/1998 |
| EP | 0 885 932 | 12/1998 |
| EP | 1 077 634 | 2/2001 |
| EP | 1 102 194 A2 | 5/2001 |
| EP | 1 266 607 | 12/2002 |
| EP | 1 338 295 A1 | 8/2003 |
| EP | 1 498 067 | 1/2005 |
| EP | 2 226 086 | 8/2010 |
| FR | 2656423 | 6/1991 |
| GB | 1 442 303 | 7/1976 |
| JP | 07/083871 | 3/1995 |
| JP | 62083849 | 4/1997 |
| JP | 2004-000555 | 1/2004 |
| WO | WO 89/02720 | 4/1989 |
| WO | WO 92/13271 | 8/1992 |
| WO | WO 93/14693 | 8/1993 |
| WO | WO 94/22367 | 10/1994 |
| WO | WO 95/13838 | 5/1995 |
| WO | WO 96/14026 | 5/1996 |
| WO | WO 96/25089 | 8/1996 |
| WO | WO 96/30431 | 10/1996 |
| WO | WO 97/01986 | 1/1997 |
| WO | WO 97/06727 | 2/1997 |
| WO | WO 99/56613 | 4/1999 |
| WO | WO 99/58051 | 11/1999 |
| WO | WO 99/59657 | 11/1999 |
| WO | WO 00/12720 | 3/2000 |
| WO | WO 00/78210 | 5/2000 |
| WO | WO 00/49941 | 8/2000 |
| WO | WO 00/74753 | 12/2000 |
| WO | WO 01/20019 | 3/2001 |
| WO | WO 01/20334 | 3/2001 |
| WO | WO 01/34243 | 5/2001 |
| WO | WO 01/68901 | 9/2001 |
| WO | WO 01/69222 | 9/2001 |
| WO | WO 01/88524 | 11/2001 |
| WO | WO 02/082989 | 10/2002 |
| WO | WO 02/100266 | 12/2002 |
| WO | WO 03/022327 | 3/2003 |
| WO | WO 2004/009161 | 1/2004 |
| WO | WO 2005/011489 | 2/2005 |
| WO | WO 2005/012873 | 2/2005 |
| WO | WO 2005/057168 | 6/2005 |
| WO | WO 2005/057175 | 6/2005 |
| WO | WO 2005/026689 | 10/2005 |
| WO | WO 2006/017358 | 2/2006 |
| WO | WO 2006/021430 | 3/2006 |
| WO | WO 2006/105146 | 10/2006 |
| WO | WO 2007/097754 | 8/2007 |
| WO | WO 2008/076868 | 6/2008 |

OTHER PUBLICATIONS

European Office Action dated Feb. 20, 2012 in EP 05723951.9, filed Feb. 24, 2005.

European Response filed Jun. 28, 2012 in EP 05723951.9, filed Feb. 24, 2005.

Japanese Decision on Appeal mailed Jul. 24, 2012 for Application No. JP 2007-500777, filed Feb. 24, 2005.

American Diabetes Association. (Jan. 2007) Position Statement: Diagnosis and Classification of Diabetes Mellitus. Diabetes Care 30(Supp. 1):S42-S47.

American Diabetes Association. (Jan. 2007) Position Statement: Standards of Medical Care in Diabetes-2007; Diabetes Care 30(Supp. 1):S4-S41.

American Diabetes Association. (Jan. 2007) Summary of Revisions for the 2007 Clinical Practice Recommendations; Diabetes Care 30(Supp. 1): S3.

Aussedat et al. (2000) Interstitial glucose concentration and glycemia: Implications for continuous subcutaneous glucose monitoring; Am J Physiol Endocrinol Metab 278: E716-E728.

Chase et al. (2005) Targeted Glycemic Reduction in Critical Care Using Closed-Loop Control; Diab Tech Therap. 7(2): 274-282.

El-Khatib et al. 2007. Adaptive closed-loop control provides blood-glucose regulation using dual subcutaneous insulin and glucagon infusion in diabetic swine, Journal of Diabetes Science and Technology, 1(2):181-192.

Frohnauer et al. 2001. Graphical human insulin time-activity profiles using standardized definitions. Diabetes Technology & Therapeutics 3(3):419-429.

Garg et al. 2004. Improved Glucose Excursions Using an Implantable Real-Time continuous Glucose Sensor in Adults with Type I Diabetes. Diabetes Care 27:734-738.

Garg, Satish K. (2005) New Insulin Analogues; Diab Tech Therap. 7(5): 813-817.

Hagvik, Joakim. (Mar. 2007) Glucose Measurment: Time for a Gold Standard; J Diab Scie Technol. 1(2): 169-172.

Heinemann et al. (2004) Review: Measurement of Insulin Absorption and Insulin Action. Diab Tech Therap. 6(5): 698-718.

Heinemann, Lutz. (2002) Review: Variability of Insulin Absorption and Insulin Action. Diab Tech Therap. 4(5): 673-682.

Heinemann, Lutz. (Mar. 2007) Measurement Quality of Blood Glucose Meters: Is there a need for an institution with an unbiased view? J Diab Scie Technol. 1(2): 178-180.

Hovorka et al. (2004) Closing the Loop: The Adicol Experience. Diab Tech Therap. 6(3): 307-318.

Hunsley et al. (Mar. 2007) Whole Blood Glucose Standard Is Key to Accurate Insulin Dosages. J Diab Scie Technol. 1(2): 173-177.

Jones et al. (2005) Optimal Insulin Pump Dosing and Postprandial Glycemia Following a Pizza Meal Using the Continuous Glucose Monitoring System; Diab Tech Therap. 7(2): 233-240.

Kizilel et al. (2005) Review: The Bioartificial Pancreas: Progress and Challenges; Diab Tech Therap. 7(6): 968-985.

Klonoff, David C. (2002) Editorial: Current, Emerging, and Future Trends in Metabolic Monitoring; Diab Tech Therap. 4(5): 582-588.

Koschinsky et al. (2003) Review: Glucose Sensors and the Alternate Site Testing-like Phenomenon: Relationship Between Rapid Blood Glucose Changes and Glucose Sensor Signals. Diab Tech Therap. 5(5): 829-842.

Lee et al. (May 2007) Combined Insulin Pump Therapy with Real-time Continuous Glucose Monitoring Significantly Improves Glycemic Control Compared to Multiple Daily Injection Therapy in Pump Naive Patients with Type 1 Diabetes; Single Center Pilot Study Experience; J Diab Scie Tech. 1(3): 400-404.

Ristic et al. (2003) Review: Effets of Rapid-acting Insulin Analogs on Overall Glycemic Control in Type 1 and Type 2 Diabetes Mellitus; Diab Tech Therap. 5(1): 57-66.

Thennadil et al. (2001) Comparison of Glucose Concentration in Interstitial Fluid, and Capillary and Venous Blood During Rapid Changes in Blood Glucose Levels; Diab Tech Therap. 3(3): 357-365.

Vesper et al. (2006) Assessment of Trueness of a Glucose Monitor Using Interstitial Fluid and Whole Blood as Specimen Matrix; Diab Tech Therap. 8(1): 76-80.

Wentholt et al. (2007) Relationship between Interstitial and Blood Glucose in Type 1 Diabetes Patients: Delay and the Push-pull Phenomenon Revisited; Diab Tech Therap. 9(2): 169-175.

Wolpert, Howard A. (2003) A Clinician's Perspective on Some of the Challenges in "Closing the Loop". Dia Tech Therap. 5(5): 843-846.

EPO Summons to Attend Oral Hearing dated Oct. 11, 2012 for Application No. 10163654.6, filed Feb. 24, 2005.

(56) References Cited

OTHER PUBLICATIONS

Electronic File History of Inter Partes Control No. 95/001,818, filed Nov. 11, 2011 containing Reexamination Request dated Nov. 11, 2011, Office Action(s) dated Nov, 25, 2011, Dec. 21, 2011, Aug. 23, 2012, Oct. 3, 2012, Dec. 19, 2012 and Feb. 8, 2013; Third Party submissions Jan. 23, 2012, Feb. 21, 2012 and Apr. 19, 2012, and Patent Owner(s) Response(s) filed Feb. 6, 2012, Mar. 20, 2012, Jul. 17, 2012 and Oct. 31, 2012 [Reexam Certification issued Feb. 27, 2013].

Adilman, Glenn, Videogames: Knowing the Score, Creative Computing, V9, p. 224(5), Dec. 1983, Dialog: File 148, Acc# 01891055.

Aussedat et al. 1997. A user-friendly method for calibrating a subcutaneous glucose sensor-based hypoglycaemic alarm. Biosensors & Bioelectronics 12(11):1061-1071.

Baker et al. 1993. Dynamic concentration challenges for biosensor characterization. Biosensors & Bioelectronics 8:433-441.

Baker et al. 1996. Dynamic delay and maximal dynamic error in continuous biosensors. Anal Chem 68(8):1292-1297.

Bani Amer, M. M. 2002. An accurate amperometric glucose sensor based glucometer with eliminated cross-sensitivity. J Med Eng Technol 26(5):208-213.

Bard et al. 1980. Electrochemical Methods. John Wiley & Sons, pp. 173-175.

Bland et al. 1986. Statistical methods for assessing agreement between two methods of clinical measurement. Lancet 1:307-310.

Bolinder et al. 1992. Microdialysis measurement of the absolute glucose concentration in subcutaneous adipose tissue allowing glucose monitoring in diabetic patients. Diabetologia 35:1177-1180.

Bolinder et al. 1997. Self-monitoring of blood glucose in type 1 diabetic patients: Comparison with continuous microdialysis measurements of glucose in subcutaneous adipose tissue during ordinary life conditions. Diabetes Care 20(1):64-70.

Bott, A. 1998. Electrochemical methods for the determination of glucose. Current Separations 17(1):25-31.

Bremer et al. 1999. Is blood glucose predictable from previous values? A solicitation for data. Diabetes 48:445-451.

Brunstein et al. 1989. Preparation and validation of implantable electrodes for the measurement of oxygen and glucose. Biomed Biochim. Acta 48(11/12):911-917.

Cameron et al. 1997. Micromodular Implants to provide electrical stimulation of paralyzed muscles and limbs. IEEE Transactions on Biomedical Engineering 44(9):781-790.

Chen et al. 2002. Defining the period of recovery of the glucose concentration after its local perturbation by the implantation of a miniature sensor. Clin. Chem. Lab. Med. 40:786-789.

Chia et al. 2004. Glucose sensors: toward closed loop insulin delivery. Endocrinol Metab Clin North Am 33:175-95.

Choleau et al. 2002. Calibration of a subcutaneous amperometric glucose sensor implanted for 7 days in diabetic patients. Part 1. Effect of measurement uncertainties on the determination of sensor sensitivity and background current. Biosensors and Bioelectronics 17:641-646.

Choleau et al. 2002. Calibration of a subcutaneous amperometric glucose sensor implanted for 7 days in diabetic patients. Part 2. Superiority of the one-point calibration method. Biosensors and Bioelectronics 17:647-654.

Clarke et al. Sep.-Oct. 1987. Evaluating Clinical Accuracy of Systems for Self-Monitoring of Blood Glucose. Diabetes Care 10(5):622-628.

Csöregi et al. 1994. Amperometric microbiosensors for detection of hydrogen peroxide and glucose based on peroxidase-modified carbon fibers. Electroanalysis 6:925-933.

Currie et al., Novel non-intrusive trans-dermal remote wireless micro-fluidic monitoring systme applied to continuous glucose and lactate assays for casualty care and combat readiness assessment, RTO HFM Symposium, St. Pete Beach, RTO-MP-HFM-109, Aug. 16-18, 2004, 18 pp.

Davies, et al. 1992. Polymer membranes in clinical sensor applications. I. An overview of membrane function, Biomaterials, 13(14):971-978.

Deutsch et al., "Time series analysis and control of blood glucose levels in diabetic patients". Computer Methods and Programs in Biomedicine 41 (1994) 167-182.

Diabetes Educational Video Game Recognized by Software Publishers Association, Press Release, Novo Nordisk, Mar. 14, 1994.

EPO Communication dated Nov. 21, 2007 in European App. No. 05723951.9, filed Feb. 24, 2005.

Fabietti et al. 2007. Clinical validation of a new control-oriented model of insulin and glucose dynamcs in subjects with type 1 diabetes, Diabetes Technology & Therapeutics, 9(4):327-338.

Freiberger, Paul, Video Game Takes on Diabetes Superhero 'Captain Novolin' Offers Treatment Tips, San Francisco Examiner, Jun. 26, 1992, Fourth Edition, Business Sec. B1.

Garg et al. 1999. Correlation of fingerstick blood glucose measurements with GlucoWatch biographer glucose results in young subjects with type 1 diabetes. Diabetes Care 22(10):1708-1714.

Heise et al. 2003. Hypoglycemia warning signal and glucose sensors: Requirements and concepts. Diabetes Technology & Therapeutics 5:563-571.

Heller, "Electrical wiring of redox enzymes," Acc. Chem. Res., 23:128-134 (1990).

ISR and WO for PCT/US05/006301 filed Feb. 24, 2005.

IPRP for PCT/US05/006301 filed Feb. 24, 2005.

Jablecki et al. 2000. Simulations of the frequency response of implantable glucose sensors. Analytical Chemistry 72:1853-1859.

Jaremko et al. 1998. Advances toward the implantable artificial pancreas for treatment of diabetes. Diabetes Care 21(3):444-450.

Jeong et al. 2003. In vivo calibration of the subcutaneous amperometric glucose sensors using a non-enzyme electrode. Biosensors and Bioelectronics 19:313-319.

Jeutter et al. 1993. Design of a radio-linked implantable cochlear prosthesis using surface acoustic wave devices. IEEE Transactions on ultrasonics, ferroelectrics and frequency control 40(5):469-477.

Joung et al. 1998. An energy transmission system for an artificial heart using leakage inductance compensation of transcutaneous transformer. IEEE Transactions on Power Electronics 13(6):1013-1022.

Kerner, W. 2001. Implantable glucose sensors: Present status and future developments. Exp. Clin. Endocrinol. Diabetes 109(Suppl 2):S341-346.

Ko, Wen H. 1985. Implantable Sensors for Closed-Loop Prosthetic Systems, Futura Pub. Co., Inc., Mt. Kisco, NY, Chapter 15:197-210.

Kovatchev et al. Aug. 2004. Evaluating the accuracy of continuous glucose-monitoring sensors: continuous glucose-error grid analysis illustrated by TheraSense Freestyle Navigator data. Diabetes Care 27(8):1922-1928.

Krouwer, J. S. 2002. Setting performance goals and evaluating total analytical error for diagnostic assays. Clinical Chemistry 48(6):919-927.

Kurnik et al. 1999. Application of the mixtures of experts algorithm for signal processing in a noninvasive glucose monitoring system. Sensors and Actuators B, 60:19-26.

LaCourse et al. 1993. Optimization of waveforms for pulsed amperometric detection of carbohydrates based on pulsed voltammetry. Analytical Chemistry 65:50-52.

Lohn et al., A knowledge-based system for real-time validation of calibrations and measurements, Chemometrics and Intelligent Laboratory Systems, 1999 46, 57-66.

Lynch et al. 2001. Estimation-based model predictive control of blood glucose in type I diabetics: A simulation study. Proceedings of the IEEE 27th Annual Northeast Bioengineering Conference, pp. 79-80.

Lynn, P. A. 1971. Recursive digital filters for biological signals. Med. & Biol. Engng. 9:37-43.

Mancy et al. 1962. A galvanic cell oxygen analyzer. Journal of Electroanalytical Chemistry 4:65-92.

Martin, R. F. 2000. General Deming regression for estimating systematic bias and its confidence interval in method-comparison studies. Clinical Chemistry, 46(1):100-104.

Matsuki. 1994. Energy transfer system utilizing amorphous wires for implantable medical devices. IEEE Transactions on Magnetics 31(2):1276-1282.

(56) References Cited

OTHER PUBLICATIONS

Mazzola et al., (Oct. 1983) Video Diabetes: A Teaching Tool for Children with Insulin-Dependent Diabetes, Proceedings—7th Annual Symposium on Computer Applications in Medical Care; Washington, D.C.; Dialog:, File 8, Acc# 01624462, 1 page Abstract.
Metzger et al. Jul. 2002. Reproducibility of glucose measurements using the glucose sensor. Diabetes Care 25(6):1185-1191.
Miller et al. 1993. Development of an autotuned transcutaneous energy transfer system ASAIO Journal 39:M706-M710.
Monsod et al. 2002. Do sensor glucose levels accurately predict plasma glucose concentrations during hypoglycemia and hyperinsulinemia? Diabetes Care 25(5):889-893.
Moussy et al. 1994. A miniaturized Nafion-based glucose sensor: In vitro and in vivo evaluation in dogs. Int. J. Artif. Organs 17(2):88-94.
Neuburger et al. 1987. Pulsed amperometric detection of carbohydrates at gold electrodes with a two-step potential waveform. Anal. Chem. 59:150-154.
Nintendo Healthcare, Wired, Dec. 1993.
Parker et al. 1999. A model-based algorithm for blood glucose control in type I diabetic patients. IEEE Trans. Biomed. Eng. 46(2):148-157.
Phillips. 1995. A high capacity transcutaneous energy transmission system. ASAIO Journal 41:M259-M262.
Pickup et al. 1993. Responses and Calibration of Amperometric Glucose Sensors Implanted in the Subcutaneous Tissue of Man. ACTA Diabetol, pp. 143-148.
Poirier et al. 1998. Clinical and statistical evaluation of self-monitoring blood glucose meters. Diabetes Care 21(11):1919-1924.
Raya Systems Pioneers Healthy Video Games, PlayRight, Nov. 1993 (pp. 14-15).
Rebrin et al. 1999. Subcutaneous glucose predicts plasma glucose independent of insulin: Implications for continuous monitoring. Am. J. Physiol. 277:E561-71.
Rinken et al. 1998. Calibration of glucose biosensors by using pre-steady state kinetic data. Biosensors & Bioelectronics, 13:801-807.
Schmidt et al. 1992. Calibration of a wearable glucose sensor. The International Journal of Artificial Organs 15(1):55-61.
Schmidtke et al. May 1998. Accuracy of the one-point in vivo calibration of "wired" glucose oxidase electrodes implanted in jugular veins of rats in periods of rapid rise and decline of the glucose concentration. Anal Chem 70(10): 2149-2155.
Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.
Smith et al. 1998. An externally powered, multichannel, implantable stimulator-telemeter for control of paralyzed muscle. IEEE Transactions on Biomedical Engineering 45(4):463-475.
Sokolov et al. 1995. Metrological opportunities of the dynamic mode of operating an enzyme amperometric biosensor. Med. Eng. Phys. 17(6):471-476.
Sparacino et al., 2008. Continuous glucose monitoring time series and hypo/hyperglycemia prevention: requirements, methods, open problems, Current Diabetes Reviews, 4:181-192.
Sproule et al. 2002. Fuzzy pharmacology: Theory and applications. Trends in Pharmacological Sciences, 23(9):412-417.
Sternberg et al. 1996. Does fall in tissue glucose precede fall in blood glucose? Diabetologia 39:609-612.
Street et al. 1988. A note on computing robust regression estimates via iteratively reweighted least squares. The American Statistician 42(2):152-154.
Tamura, T. et al. 2000. Preliminary study of continuous glucose monitoring with a microdialysis technique and a null method—a numerical analysis. Frontiers Med. Biol. Engng. 10(2):147-156.
Tilbury et al. 2000. Receiver operating characteristic analysis for intelligent medical systems—A new approach for finding confidence intervals. IEEE Transactions on Biomedical Engineering 47(7):952-963.

Trajanoski et al. 1998. Neural predictive controller for insulin delivery using the subcutaneous route. IEEE Transactions on Biomedical Engineering 45(9):1122-1134.
Updike et al. 1979. Continuous glucose monitor based on an immobilized enzyme electrode detector. J Lab Clin Med, 93(4):518-527.
Updike et al. 1982. Implanting the glucose enzyme electrode: Problems, progress, and alternative solutions. Diabetes Care, 5(3):207-212.
Valdes et al. 2000. In vitro and in vivo degradation of glucose oxidase enzyme used for an implantable glucose biosensor. Diabetes Technol. Ther. 2:367-376.
Velho et al. 1989. In vitro and in vivo stability of electrode potentials in needle-type glucose sensors. Influence of needle material. Diabetes 38:164-171.
Velho et al. 1989. Strategies for calibrating a subcutaneous glucose sensor. Biomed Biochim Acta 48(11/12):957-964.
von Woedtke et al. 1989. In situ calibration of implanted electro-chemical glucose sensors. Biomed Biochim. Acta 48(11/12):943-952.
Ward et al. 1999. Assessment of chronically implanted subcutaneous glucose sensors in dogs: The effect of surrounding fluid masses. ASAIO Journal, 45:555-561.
Zavalkoff et al. 2002. Evaluation of conventional blood glucose monitoring as an indicator of integrated glucose values using a continuous subcutaneous sensor. Diabetes Care 25(9):1603-1606.
Ziaie et al. 1997. A single-channel implantable microstimulator for functional neuromuscular stimulation. IEEE Transactions on Biomedical Engineering 44(10):909-920.
Panteleon et al. 2003. The role of the independent variable to glucose sensor calibration. Diabetes Technology & Therapeutics 5(3):401-410.
EPO Communication dated Sep. 7, 2010 in EP App. No. 05723951.9.
EPO Communication dated Aug. 3, 2010 for EP 10163675.1, Filed Feb. 24, 2005.
EPO Communication dated Mar. 17, 2011 for EP 10163675.1, filed Feb. 24, 2005.
EPO Communication dated Aug. 3, 2010 for EP 10163654.6, filed Feb. 24, 2005.
ISR and WO dated Aug. 28, 2008 for PCT/US07/080848, filed Oct. 9, 2007.
IPRP dated Apr. 22, 2010 for PCT/US07/080848, filed Oct. 9, 2007.
ISR and WO dated Aug. 8, 2008 for PCT/US08/058158, filed Mar. 25, 2008.
IPRP dated Sep. 29, 2009 for PCT/US08/058158, filed Mar. 25, 2008.
JIPO Communication dated Aug. 17, 2010 in JP Application No. 2007-500777 filed Feb. 24, 2005.
JIPO Communication dated Jun. 28, 2011 in JP Application No. 2007-500777, filed Feb. 24, 2005.
Office Action dated Nov. 28, 2007 in U.S. Appl. No. 10/991,966.
Office Action dated Jul. 22, 2008 in U.S. Appl. No. 10/991,966.
Office Action dated Jul. 29, 2010 in U.S. Appl. No. 12/364,786.
Office Action dated Oct. 5, 2010 in U.S. Appl. No. 12/055,098.
Electronic File History of U.S. Appl. No. 12/579,385, filed Oct. 14, 2009 containing Office Action(s) dated Aug. 23, 2010, Feb. 17, 2011 and Jul. 14, 2011 and Applicant(s) Response(s) filed Nov. 16, 2010, Apr. 18, 2011 and Jul. 25, 2011 as of Jul. 25, 2011.
Electronic File History of U.S. Appl. No. 10/789,359, filed Feb. 26, 2004 (now US Patent No. 7,591,801, issued Sep. 22, 2009) containing Office Action(s) dated Aug. 9, 2006, Nov. 27, 2006, Mar. 20, 2008, Oct. 3, 2008, Feb. 24, 2009, Mar. 30, 2009, Apr. 22, 2009, Apr. 23, 2009, and Jul. 15, 2009 and Applicant(s) Response(s) filed Aug. 31, 2006, Feb. 6, 2007, May 28, 2008, Nov. 24, 2008, Mar. 31, 2009, and Apr. 22, 2009.
Electronic File History of U.S. Appl. No. 12/133,820, filed Jun. 5, 2008 containing Office Action(s) dated Aug. 20, 2010, Nov. 5, 2010, Jan. 26, 2011, and Mar. 22, 2011 and Applicant Response(s) filed Aug. 25, 2010, Feb. 7, 2011, and Jun. 22, 2011 as of Jun. 23, 2011.
Electronic File History of U.S. Appl. No. 12/536,852, filed Aug. 6, 2009 (now U.S. Patent No. 7,976,492 issued Jul. 12, 2011) containing Office Action(s) dated Jun. 25, 2010, Oct. 18, 2010, and Feb. 25, 2011 and Applicant(s) Response(s) filed Aug. 3, 2010, Dec. 8, 2010, and May 11, 2011.

(56) References Cited

OTHER PUBLICATIONS

Electronic File History of U.S. Appl. No. 12/133,738, filed Jun. 5, 2008 containing Office Action(s) dated Aug. 23, 2010, Sep. 10, 2010 and Feb. 14, 2011 and Applicant(s) Response(s) filed Aug. 31, 2010, Dec. 7, 2010 and May 16, 2011 as of May 18, 2011.
Electronic File History of U.S. Appl. No. 12/133,761, filed Jun. 5, 2008 containing Office Action(s) dated Aug. 23, 2010, Sep. 7, 2010 and Feb. 14, 2011 and Applicant Response(s) filed Aug. 25, 2010, Dec. 6, 2010, Apr. 14, 2011 and May 16, 2011 as of May 19, 2011.
Electronic File History of U.S. Appl. No. 12/133,786, filed Jun. 5, 2008 containing Office Action(s) dated Aug. 23, 2010, Sep. 8, 2010 and Feb. 14, 2011 and Applicant Response(s) filed Aug. 25, 2010, Dec. 7, 2010, Apr. 13, 2011 and Mar 13, 2011 as of May 19, 2011.
de Vos et al., Considerations for succesfful transplantation of encapsulated pancreatic islets, Diabetol. (2002) 45: 159-173.
Gough (May 2001) The implantable glucose sensor: An example of bioengineering design. Introduction to Bioengineering, Chapter 3, pp. 57-66.
Gross et al. 2000 Performance evaluation of the MiniMed® continuous glucose monitoring system during patient home use. Diabetes Technology & Therapeutics 2(1): 49-56.
Koschinsky et al. 2001 Sensors for glucose monitoring: Technical and clinical aspects. Diabetes Metab. Res. Rev. 17:113-123.
Smith et al. 1991 A Comparison of Islet Transplantation and Subcutaneous Insulin Injections for the Treatment of Diabetes Mellitus, Comput Biol Med. 21(6): 417-427.
Street et al. Dec. 2004 Islet Graft Assessment in the Edmonton Protocol: Implications for Predicting Long-Term Clinical Outcome, Diabetes, 53: 3107-3114.
US 7,530,950, 5/2009, Brister et al. (withdrawn).
Aalders et al. 1991. Development of a wearable glucose sensor; studies in healthy volunteers and in diabetic patients. The International Journal of Artificial Organs 14(2):102/108.
Abe et al. 1992. Characterization of glucose microsensors for intracellular measurements. Alan. Chem. 64(18):2160/2163.
Abel et al. 1984. Experience with an implantable glucose sensor as a prerequisite of an artifical beta cell, Biomed. Biochim. Acta 43(5):577/584.
Alcock & Turner. 1994. Continuous Analyte Monitoring to Aid Clinical Practice. IEEE Engineering in Med. & Biol. Mag. 13:319/325.
American Heritage Dictionary, 4th Edition. 2000. Houghton Mifflin Company, p. 82.
Amin et al. 2003. Hypoglycemia prevalence in prepubertal children with type 1 diabetes on standard insulin regimen: Use of continuous glucose monitoring system. Diabetes Care 26(3):662/667.
Answers.com. "xenogenic." The American Heritage Stedman's Medical Dictionary. Houghton Mifflin Company, 2002. Answers.com Nov. 7, 2006 http://www. Answers.com/topic/xenogenic.
Atanasov et al. 1994. Biosensor for continuous glucose monitoring. Biotechnology and Bioengineering 43:262/266.
Atanasov et al. 1997. Implantation of a refillable glucose monitoring/telemetry device. Biosens Bioelectron 12:669/680.
Bailey et al. 2007. Reduction in hemoglobin A1c with real/time continuous glucose monitoring: results from a 12/week observational study. Diabetes Technology & Therapeutics 9(3):203/210.
Beach et al. 1999. Subminiature implantable potentiostat and modified commercial telemetry device for remote glucose monitoring. IEEE Transactions on Instrumentation and Measurement 48(6):1239/1245.
Bellucci et al. Jan. 1986. Electrochemical behaviour of graphite/epoxy composite materials (GECM) in aqueous salt solutions, Journal of Applied Electrochemistry, 16(1):15/22.
Bessman et al., Progress toward a glucose sensor for the artificial pancreas, Proceedings of a Workshop on Ion/Selective Microelectrodes, Jun. 4/5, 1973, Boston, MA, 189/197.
Biermann et al. 2008. How would patients behave if they were continually informed of their blood glucose levels? A simulation study using a "virtual" patient. Diab. Thechnol. & Therapeut., 10:178/187.

Bindra et al. 1989. Pulsed amperometric detection of glucose in biological fluids at a surface/modified gold electrode. Anal Chem 61:2566/2570.
Bindra et al. 1991. Design and In Vitro Studies of a Needle/Type Glucose Senso for Subcutaneous Monitoring. Anal. Chem 63:1692/96.
Bisenberger et al. 1995. A triple/step potential waveform at enzyme multisensors with thick/film gold electrodes for detection of glucose and sucrose. Sensors and Actuators, B 28:181/189.
Boedeker Plastics, Inc. 2009. Polyethylene Specifications Data Sheet, http://www.boedeker.com/polye_p.htm [Aug. 19, 2009 3:36:33 PM].
Boland et al. 2001. Limitations of conventional methods of self/monitoring of blood glucose. Diabetes Care 24(11):1858/1862.
Bott, A. W. 1997. A Comparison of Cyclic Voltammetry and Cyclic Staircase Voltammetry Current Separations 16:1, 23/26.
Bowman, L.; Meindl, J. D. 1986. The packaging of implantable integrated sensors. IEEE Trans Biomed Eng BME33(2):248/255.
Brauker et al. Jun. 27, 1996. Local Inflammatory Response Around Diffusion Chambers Containing Xenografts Transplantation 61(12):1671/1677.
Braunwald, 2008. Biomarkers in heart failure. N. Engl. J. Med., 358: 2148/2159.
Bremer et al. 2001. Benchmark data from the literature for evaluation of new glucose sensing technologies. Diabetes Technology & Therapeutics 3(3):409/418.
Brooks et al. "Development of an on/line glucose sensor for fermentation monitoring," Biosensors, 3:45/56 (1987/88).
Bruckel et al. 1989. In vivo measurement of subcutaneous glucose concentrations with an enzymatic glucose sensor and a wick method. Klin Wochenschr 67:491/495.
Cai et al. 2004. A wireless, remote query glucose biosensor based on a pH/sensitive polymer. Anal Chem 76(4):4038/4043.
Campanella et al. 1993. Biosensor for direct determination of glucose and lactate in undiluted biological fluids. Biosensors & Bioelectronics 8:307/314.
Cassidy et al., Apr. 1993. Novel electrochemical device for the detection of cholesterol or glucose, Analyst, 118:415/418.
Chase et al. 2001. Continuous subcutaneous glucose monitoring in children with type 1 diabetes. Pediatrics 107:222/226.
Ciba® Irgacure 2959 Photoinitiator Product Description, Ciba Specialty Chemicals Inc., Basel, Switzerland, Apr. 2, 1998, 3 pages.
Claremont et al. 1986. Subcutaneous implantation of a ferrocene/mediated glucose sensor in pigs. Diabetologia 29:817/821.
Claremont et al. Jul. 1986. Potentially/implntable, ferrocene/mediated glucose sensor. J. Biomed. Eng. 8:272/274.
Clark et al. 1987. Configurational cyclic voltammetry: increasing the specificity and reliablity of implanted electrodes, IEEE/Ninth Annual Conference of the Engineering in Medicine and Biology Society, pp. 0782-0783.
Clark et al. 1988. Long/term stability of electroenzymatic glucose sensors implanted in mice. Trans Am Soc Artif Intern Organs 34:259/265.
Clark et al., 1981. One/minute electrochemical enzymic assay for cholesterol in biological materials, Clin. Chem. 27(12):1978/1982.
CLSI. Performance metrics for continuous interstitial glucose monitoring; approved guideline, CLSI document POCT05/A. Wayne, PA: Clinical and Laboratory Standards Institute: 2008 28(33), 72 pp.
Colangelo et al. 1967. Corrosion rate measurements in vivo, Journal of Biomedical Materials Research, 1:405/414.
Colowick et al. 1976. Methods in Enzymlology, Volume XLIV, Immobilized Enzymes. New York: Academic Press.
Cox et al. 1985. Accuracy of perceiving blood glucose in IDDM. Diabetes Care 8(6):529/536.
Csoregi et al., 1994. Design, characterization, and one/point in vivo calibration of a subcutaneously implanted glucose electrode. Anal Chem. 66(19):3131/3138.
Danielsson et al. 1988. Enzyme thermistors, Methods in Enzymology, 137:181/197.
Dassau et al., In silico evaluation platform for artifical pancreatic β/cell development/a dynamic simulator for closed loop control with hardware/in/the/loop, Diabetes Technology & Therapeutics, 11(3):1/8, 2009.

(56) References Cited

OTHER PUBLICATIONS

Davis et al. 1983. Bioelectrochemical fuel cell and sensor based on a quinoprotein, alcohol dehydrogenase. Enzyme Microb. Technol., 5: 383/388.

de Vos et al., Considerations for successful transplantation of encapsulated pancreatic islets, Diabetol. (2002) 45: 159/173.

Direct 30/30® Blood Glucose Sensor, (Markwell Medical) Catalog, © 1990, ELCO Diagnostics Company. 1 page.

Dixon et al. 2002. Characterization in vitro and in vivo of the oxygen dependence of an enzyme/polymer biosensor for monitoring brain glucose. Journal of Neuroscience Methods 119:135/142.

DuPont[1] Dimension AR® (Catalog), 1998, 18 pages.

Durliat et al. 1976. Spectrophotometric and electrochemical determinations of L(+)/lactate in blood by use of lactate dehydrogenase from yeast, Clin. Chem. 22(11):1802/1805.

Edwards Lifesciences. Accuracy for your and your patients. Marketing materials, 4 pp. 2002.

El Degheidy et al. 1986. Optimization of an implantable coated wire glucose sensor. J. Biomed Eng. 8: 121/129.

El/Khatib et al. 2007. Adaptive closed/loop control provides blood/glucose regulation using dual subcutaneous insulin and glucagon infusion in diabetic swine, Journal of Diabetes Science and Technology, 1(2):181/192.

El/Sa'ad et al. 1990. Moisture Absorption by Epoxy Resins: the Reverse Thermal Effect. Journal of Materials Science 25:3577/3582.

Ernst et al. 2002. Reliable glucose monitoring through the use of microsystem technology. Anal. Bioanal. Chem. 373:758/761.

Fahy et al., An analysis: hyperglycemic intensive care patients need continuous glocuse monitoring//easier said than done, Journal of Diabetese Science and Technology, 2(2):201/204, Mar. 2008.

Fare et al. 1998. Functional characterization of a conducting polymer/based immunoassay system. Biosensors & Bioelectronics 13(3/4):459/470.

Feldman et al. 2003. A continuous glucose sensor based on wired enzyme technology//results from a 3/day trial in patients with type/1 diabetes. Diabetes Technol Ther 5(5):769/779.

Fischer et al. 1987. Assessment of subcutaneous glucose concentration: validation of the wick technique as a reference for implanted electrochemical sensors in normal and diabetic dogs, Diabetologia 30:940/945.

Fischer et al. 1989. Oxygen Tension at the Subcutaneous Implantation Site of Glucose Sensors. Biomed. Biochem 11/12:965/972.

Fischer et al. 1995. Hypoglycaemia/warning by means of subcutaneous electrochemical glucose sensors: an animal study, Horm. Metab. Rese. 27:53.

Freedman et al. 1991. Statistics, Second Edition, W.W. Norton & Company, p. 74.

Frohnauer et al. 2001. Graphical human insulin time/activity profiles using standardized definitions. Diabetes Technology & Therapeutics 3(3):419/429.

Gabbay et al. 2008. Optical coherence tomography/based continuous noninvasive glucose monitoring in patients with diabetes. Diab. Thechnol. & Therapeut., 10:188/193.

Ganesan et al., Gold layer/based dual crosslinking procedure of glucose oxidase with ferrocene monocarboxylic acid provides a stable biosensor, Analytical Biochemistry 343:188/191, 2005.

Ganesh et al., Evaluation of the VIA® blood chemistry monitor for glucose in healthy and diabetic volunteers, Journal of Diabetese Science and Technology, 2(2):182/193, Mar. 2008.

Gerritsen et al. 1999. Performance of subcutaneously implanted glucose sensors for continuous monitoring. The Netherlands Journal of Medicine 54:167/179.

Gerritsen, M. 2000. Problems associated with subcutaneously implanted glucose sensors. Diabetes Care 23(2):143/145.

Gilligan et al. 1994. Evaluation of a subcutaneous glucose sensor out to 3 months in a dog model. Diabetes Care 17(8):882/887.

Godsland et al. 2001. Maximizing the Success Rate of Minimal Model Insulin Sensitivity Measurement in Humans: The Importance of Basal Glucose Levels. The Biochemical Society and the Medical Research Society, 1/9.

Gouda et al., Jul. 4, 2003. Thermal inactiviation of glucose oxidase, The Journal of Biological Chemistry, 278(27):24324/24333.

Gough et al. 2000. Immobilized glucose oxidase in implantable glucose sensor technology. Diabetes Technology & Therapeutics 2(3):377/380.

Gough et al. 2003. Frequency characterization of blood glucose dynamics. Annals of Biomedical Engineering 31:91/97.

Gross et al. 2000. Efficacy and reliability of the continuous glucose monitoring system. Diabetes Technology & Therapeutics, 2(Suppl 1):S19/26.

Gross et al. 2000. Performance evaluation of the MiniMed® continuous glucose monitoring system during patient home use. Diabetes Technology & Therapeutics 2(1): 49/56.

Hall et al. 1998. Electrochemical oxidation of hydrogen peroxide at platinum electrodes. Part I: An adsorption/controlled mechanism. Electrochimica Acta, 43(5/6):579/588.

Hall et al. 1998. Electrochemical oxidation of hydrogen peroxide at platinum electrodes. Part II: Effect of potential. Electrochimica Acta 43(14/15):2015/2024.

Hall et al. 1999. Electrochemical oxidation of hydrogen peroxide at platinum electrodes. Part III: Effect of temperature. Electrochimica Acta, 44:2455/2462.

Hall et al. 1999. Electrochemical oxidation of hydrogen peroxide at platinum electrodes. Part IV: Phosphate buffer dependence. Electrochimica Acta, 44:4573/4582.

Hall et al. 2000. Electrochemical oxidation of hydrogen peroxide at platinum electrodes. Part V: Inhibition by chloride. Electrochimica Acta, 45:3573/3579.

Hamilton Syringe Selection Guide. 2006. Syringe Selection. www.hamiltoncompany.com.

Hashiguchi et al. (1994). "Development of a miniaturized glucose monitoring system by combining a needle/type glucose sensor with microdialysis sampling method: Long/term subcutaneous tissue glucose monitoring in ambulatory diabetic patients," *Diabetes Care*, 17(5): 387/396.

Heller, A. 1992. Electrical Connection of Enzyme Redox Centers to Electrodes. J. Phys. Chem. 96:3579/3587.

Heller, A. 2003. Plugging metal connectors into enzymes. Nat Biotechnol 21:631/2.

Hicks, 1985. In Situ Monitoring, Clinical Chemistry, 31(12):1931/1935.

Hitchman, M. L. 1978. Measurement of Dissolved Oxygen. In Elving et al. (Eds.). Chemical Analysis, vol. 49, Chap. 3, pp. 34-49, 59-123. New York: John Wiley & Sons.

Hoel, Paul G. 1976. Elementary Statistics, Fourth Edition. John Wiley & Sons, Inc.. pp. 113-114.

Hrapovic et al. 2003. Picoamperometric detection of glucose at ultrasmall platinum/based biosensors: preparation and characterization. Anal Chem 75:3308/3315.

http://www.merriam/webster.com/dictionary, definition for "aberrant," Aug. 19, 2008, p. 1.

Hu, et al. 1993. A needle/type enzyme/based lactate sensor for in vivo monitoring, Analytica Chimica Acta, 281:503/511.

Huang et al., Sep. 1997, A 0.5mW Passive Telemetry IC for Biomedical Applications, Proceedings of the 23rd European Solid/State Circuits Conference (ESSCIRC '97), pp. 172/175, Southampton, UK.

Huang et al. Aug. 1975. Electrochemical Generation of Oxygen. 1: The Effects of Anions and Cations on Hydrogen Chemisorption and Anodic Oxide Film Formation on Platinum Electrode. 2: The Effects of Anions and Cations on Oxygen Generation on Platinum Electrode. U.S. Department of Commerce/NTIS, pp. 1/116.

Ishikawa et al. 1998. Initial evaluation of a 290/mm diameter subcutaneous glucose sensor: Glucose monitoring with a biocompatible, flexible/wire, enzyme/based amperometric microsensor in diabetic and nondiabetic humans. Journal of Diabetes and its Complications, 12:295/301.

Jaffari et al., Recent advances in amperometric glucose biosensors for in vivo monitoring, Physiol. Meas. 16 (1995) 1/15.

Jensen et al. 1997. Fast wave forms for pulsed electrochemical detection of glucose by incorporation of reductive desorption of oxidation products. Analytical Chemistry 69(9):1776/1781.

(56) References Cited

OTHER PUBLICATIONS

Jeutter, D. C. 1982. A transcutaneous implanted battery recharging and biotelemeter power switching system. IEEE Trans Biomed Eng 29:314/321.

Johnson (1991). "Reproducible electrodeposition of biomolecules for the fabrication of miniature electroenzymatic biosensors," Sensors and Actuators B, 5:85/89.

Jovanovic, L. 2000. The role of continuous glucose monitoring in gestational diabetes mellitus. Diabetes Technology & Therapeutics, 2 Suppl 1, S67/71.

Kacaniklic et al. May/Jun. 1994. Amperometric Biosensors for Detection of L/ and D/Amino Acids Based on Coimmoblized Peroxidase and L/ and D/Amino Acid Oxidases in Carbon Paste Electrodes. Electroanalysis, 6(5/6): 381/390.

Kamath et al. Calibration of a continuous glucose monitor: effect of glucose rate of change, Eighth Annual Diabetes Technology Meeting, Nov. 13-15, 2008, p. A88.

Kang et al. 2003. In vitro and short/term in vivo characteristics of a Kel/F thin film modified glucose sensor. Anal Sci 19:1481/1486.

Kaufman et al. 2001. A pilot study of the continuous glucose monitoring system. Diabetes Care 24(12):2030/2034.

Kaufman. 2000. Role of the continuous glucose monitoring system in pediatric patients. Diabetes Technology & Therapeutics 2(1):S/49 / S/52.

Kawagoe et al. 1991. Enzyme/modified organic conducting salt microelectrode, Anal. Chem. 63:2961/2965.

Keedy et al. 1991. Determination of urate in undiluted whole blood by enzyme electrode. Biosensors & Bioelectronics, 6: 491/499.

Kerner et al. "The function of a hydrogen peroxide/detecting electroenzymatic glucose electrode is markedly impaired in human sub/cutaneous tissue and plasma," Biosensors & Bioelectronics, 8:473/482 (1993).

Kerner et al. 1988. A potentially implantable enzyme electrode for amperometric measurement of glucose, Horm Metab Res Suppl. 20:8/13.

Klueh et al. 2003. Use of Vascular Endothelia Cell Growth Factor Gene Transfer to Enhance Implantable Sensor Function in Vivo, Biosensor Function and Vegf/Gene Transfer, pp. 1072-1086.

Kondo et al. 1982. A miniature glucose sensor, implantable in the blood stream. Diabetes Care. 5(3):218/221.

Kost et al. 1985. Glucose/sensitive membranes containing glucose oxidase: activitiy, swelling, and permeability studies, Journal of Biomedical Materials Research 19:1117/1133.

Koudelka et al. 1989. In vivo response of microfabricated glucose sensors to glycemia changes in normal rats. Biomed Biochim Acta 48(11/12):953/956.

Koudelka et al. 1991. In/vivo behaviour of hypodermically implanted microfabricated glucose sensors. Biosensors & Bioelectronics 6:31/36.

Kraver et al. 2001. A mixed/signal sensor interface microinstrument. Sensors and Actuators A 91:266/277.

Kruger et al. 2000. Psychological motivation and patient education: A role for continuous glucose monitoring. Diabetes Technology & Therapeutics, 2(Suppl 1):S93/97.

Kulys et al., 1994. Carbon/paste biosensors array for long/term glucose measurement, Biosensors& Beioelectronics, 9:491/500.

Kunjan et al., Automated blood sampling and glocuse sensing in critical care settings, Journal of Diabetes Science and Technology 2(3):194/200, Mar. 2008.

Kurtz et al. 2005. Recommendations for blood pressure measurement in humans and experimental animals, Part 2: Blood pressure measurement in experimental animals, A statement for professionals from the subcommittee of professional and public education of the American Heart Association Council on High Blood Pressure Research. Hypertension 45:299/310.

Ladd et al., Structure Determination by X/ray Crystallography, 3rd ed. Plenum, 1996, Ch. 1, pp. xxi-xxiv and 1-58.

Lewandowski et al. 1988. Evaluation of a miniature blood glucose sensor. Trans Am Soc Artif Intern Organs 34:255/258.

Leypoldt et al. 1984. Model of a two/substrate enzyme electrode for glucose. Anal. Chem. 56:2896/2904.

Linke et al. 1994. Amperometric biosensor for in vivo glucose sensing based on glucose oxidase immobilized in a redox hydrogel. Biosensors & Bioelectronics 9:151/158.

Lowe, 1984. Biosensors, Trends in Biotechnology, 2(3):59/65.

Luong et al. 2004. Solubilization of Multiwall Carbon Nanotubes by 3/Aminopropyltriethoxysilane Towards the Fabrication of Electrochemical Biosensors with Promoted Electron Transfer. Electronanalysis 16(1/2):132/139.

Lyandres et al. (2008). Progress toward an in vivo surface/enhanced raman spectroscopy glucose sensor. Diabetes Technology & Therapeutics, 10(4): 257/265.

Maidan et al. 1992. Elimination of Electrooxidizable Interferent/Produced Currents in Amperometric Biosensors, Analytical Chemistry, 64:2889/2896.

Makale et al. 2003. Tissue window chamber system for validation of implanted oxygen sensors. Am. J. Physiol. Heart Circ. Physiol. 284:H2288/2294.

Malin et al. 1999. Noninvasive Prediction of Glucose by Near/Infrared Diffuse Reflectance Spectroscopy. Clinical Chemistry 45:9, 1651/1658.

Maran et al. 2002. Continuous subcutaneous glucose monitoring in diabetic patients: A multicenter analysis. Diabetes Care 25(2):347/352.

Marena et al. 1993. The artifical endocrine pancreas in clinical practice and research. Panminerva Medica 35(2):67/74.

Mascini et al. 1989. Glucose electrochemical probe with extended linearity for whole blood. J Pharm Biomed Anal 7(12): 1507/1512.

Mastrototaro et al. "An electroenzymatic glucose sensor fabricated on a flexible substrate," Sensors and Actuators B, 5:139/44 (1991).

Mastrototaro et al. 2003. Reproducibility of the continuous glucose monitoring system matches previous reports and the intended use of the product. Diabetes Care 26:256; author reply p. 257.

Mastrototaro, J. J. 2000. The MiniMed continuous glucose monitoring system. Diabetes Technol Ther 2(Suppl 1):S13/8.

Matsumoto et al. 1998. A micro/planar amperometeric glucose sensor unsusceptible to interference species. Sensors and Actuators B 49:68/72.

Matthews et al. 1988. An amperometric needle/type glucose sensor testing in rats and man. Diabetic Medicine 5:248/252.

Mazze et al. 2008. Characterizing glucose exposure for individuals with normal glucose tolerance using continuous glucose monitoring and ambulatory glucose profile analysis. Diab. Thechnol. & Therapeut., 10:149/159.

Mazzola et al., Video Diabetes: A Teaching Tool for Children with Insulin/ Dependent Diabetes, Proceedings / 7th Annual Symposium on Computer Applications in Medical Care; Washington, D.C.; Dialog:, (Oct. 1983), File 8, Acc# 01624462.

McCartney et al. 2001. Near/infrared fluorescence lifetime assay for serum glucose based on allophycocyanin/labeled concanavalin A. Anal Biochem 292:216/221.

McGrath et al. 1995. The use of differential measurements with a glucose biosensor for interference compensation during glucose determinations by flow injection analysis. Biosens Bioelectron 10:937/943.

Memoli et al. 2002. A comparison between different immobilised glucoseoxidase/based electrodes. J Pharm Biomed Anal 29:1045/1052.

Merriam/Webster Online Dictionary. Definition of "acceleration". http://www.merriam/webster.com/dictionary/Acceleration Jan. 11, 2010.

Merriam/Webster Online Dictionary. Definition of "system". http://www.merriam/webster.com/dictionary/System Jan. 11, 2010.

Merriam/Webster Online Dictionary. The term "nominal." http://www.m/w.com/dictionary/nominal Apr. 23, 2007.

Meyerhoff et al. 1992. On line continuous monitoring of subcutaneous tissue glucose in men by combining portable glucosensor with microdialysis. Diabetologia 35:1087/1092.

Moatti/Sirat et al. 1992. Towards continuous glucose monitoring: in vivo evaluation of a miniaturized glucose sensor implanted for several days in rat subcutaneous tissue. Diabetologia 35:224/230.

(56) References Cited

OTHER PUBLICATIONS

Moatti/Sirat et al., Reduction of acetaminophen interference in glucose sensors by a composite Nafion membrane: demonstration in rats and man, Diabetologia 37(6):610/616, Jun. 1994.
Morff et al. 1990. Microfabrication of reproducible, economical, electroenzymatic glucose sensors, Annual International Conference of the IEEE Engineering in Medicine and Biology Society, 12(2):0483/0484.
Mosbach et al. 1975. Determination of heat changes in the proximity of immobilized enzymes with an enzyme termistor and its use for the assay of metobolites, Biochim. Biophys. Acta. (Enzymology), 403:256/265.
Motonaka et al. 1993. Determination of cholesteral and cholesteral ester with novel enzyme microsensors, Anal. Chem. 65:3258/3261.
Murphy, et al. 1992. Polymer membranes in clinical sensor applications. II. The design and fabrication of permselective hydrogels for electrochemical devices, Biomaterials, 13(14):979/990.
Muslu. 1991. Trickling filter performance. Apllied Biochemistry and Biotechnology 37:211/224.
Nafion® 117 Solution Product Description, Product No. 70160, Sigma/Aldrich Corp., St. Louis, MO. Apr. 7, 2005.
Ohara et al. 1994. "Wired" enzyme electrodes for amperometric determination of glucose or lactate in the presence of interfering substances. Anal Chem 66:2451/2457.
Ohara, et al. Dec. 1993. Glucose electrodes based on cross/linked bis(2,2'/bipyridine)chloroosmium(+/2+) complexed poly(1/vinylimidazole) films, Analytical Chemistry, 65:3512/3517.
Okuda et al. 1971. Mutarotase effect on micro determinations of D/glucose and its anomers with β/D/glucose oxidase. Anal Biochem 43:312/315.
Oxford English Dictionary Online. Definition of "impending". http://www.askoxford.com/results/?view=dev dict&field/12668446 Impending&branch= Jan. 11, 2010.
Palmisano et al. 2000. Simultaneous monitoring of glucose and lactate by an interference and cross/talk free dual electrode amperometric biosensor based on electropolymerized thin films. Biosensors & Bioelectronics 15:531/539.
Patel et al. 2003. Amperometric glucose sensors based on ferrocene containing polymeric electron transfer systems/a preliminary report. Biosens Bioelectron 18:1073/6.
Peacock et al. 2008. Cardiac troponin and outcome in acute heart failure. N. Engl. J. Med., 358: 2117/2126.
Pfeiffer et al. 1992. On line continuous monitoring of subcutaneous tissue glucose is feasible by combining portable glucosensor with microdialysis. Horm. Metab. Res. 25:121/124.
Pfeiffer, E.F. 1990. The glucose sensor: the missing link in diabetes therapy, Horm Metab Res Suppl. 24:154/164.
Pichert et al. 2000. Issues for the coming age of continuous glucose monitoring Diabetes Educ 26(6):969/980.
Pickup et al. "Implantable glucose sensors: choosing the appropriate sensing strategy," Biosensors, 3:335/346 (1987/88).
Pickup et al. 1989. Potentially/implantable, amperometric glucose sensors with mediated electron transfer: improving the operating stability. Biosensors 4:109/119.
Pickup et al. 1993. Developing glucose sensors for in vivo use. Elsevier Science Publishers Ltd (UK), Tibtech vol. 11: 285/291.
Pinner et al., Cross/linking of cellulose acetate by ionizing radiation, Nature, vol. 184, 1303/1304, Oct. 24, 1959.
Pitzer et al. 2001. Detection of hypoglycemia with the GlucoWatch biographer. Diabetes Care 24(5):881/885.
Poitout et al. 1994. Development of a glucose sensor for glucose monitoring in man: the disposable implant concept. Clinical Materials 15:241/246.
Poitout, et al. 1991. In Vitro and In Vivo Evaluation in Dogs of a Miniaturized Glucose Sensor, ASAIO Transactions, 37:M298/M300.
Postlethwaite et al. 1996. Interdigitated array electrode as an alternative to the rotated ring/disk electrode for determination of the reaction products of dioxygen reduction. Analytical Chemistry 68:2951/2958.

Quinn et al. 1995. Kinetics of glucose delivery to subcutaneous tissue in rats measured with 0.3/mm amperometric microsensors. The American Physiological Society E155/E161.
Quinn et al. 1997. Biocompatible, glucose/permeable hydrogel for in situ coating of implantable biosensors. Biomaterials 18:1665/1670.
Rabah et al., 1991. Electrochemical wear of graphite anodes during electrolysis of brine, Carbon, 29(2):165/171.
Rafael, Ehab, Cell Transplantation and Immunoisolation: Studies on a macroencapsulation device, Departments of Transplantation Surgery and Pathology, Karolinska Institutet, Huddinge Hospital, Stockholm, Sweden (1999) pp. 1-82.
Reach et al. 1986. A Method for Evaluating in vivo the Functional Characteristics of Glucose Sensors. Biosensors 2:211/220.
Reach et al. 1992. Can continuous glucose monitoring be used for the treatment of diabetes? Analytical Chemistry 64(5):381/386.
Reach, G. 2001. Which threshold to detect hypoglycemia? Value of receiver/operator curve analysis to find a compromise between sensitivity and specificity. Diabetes Care 24(5):803/804.
Reach, Gerard. 2001. Letters to the Editor Re: Diabetes Technology & Therapeutics, 2000;2:49/56. Diabetes Technology & Therapeutics 3(1):129/130.
Rebrin et al. 1992. Subcutaenous glucose monitoring by means of electrochemical sensors: fiction or reality? J. Biomed. Eng. 14:33/40.
Reusch. 2004. Chemical Reactivity. Organometallic Compounds. Virtual Textbook of Organic Chem. pp. 1-16, http://www.cem.msu.edu/~reusch/VirtualText/orgmetal.htm.
Rhodes et al. 1994. Prediction of pocket/portable and implantable glucose enzyme electrode performance from combined species permeability and digital simulation analysis. Analytical Chemistry 66(9):1520/1529.
Rigla et al. 2008. Real/time continuous glucose monitoring together with telemedical assitance improves glycemic control and glucose stability in pump/treated patients. Diab. Thechnol. & Theraput., 10:194/199.
Sakakida et al. 1992. Development of Ferrocene/Mediated Needle/Type Glucose Sensor as a Measure of True Subcutaneous Tissue Glucose Concentrations. Artif. Organs Today 2(2):145/158.
Sakakida et al. 1993. Ferrocene/Mediated Needle Type Glucose Sensor Covered with Newly Designed Biocompatible Membran, Sensors and Actuators B 13/14:319/322.
Salardi et al. 2002. The glucose area under the profiles obtained with continuous glucose monitoring system relationships with HbA1c in pediatric type 1 diabetic patients. Diabetes Care 25(10):1840/1844.
San Diego Plastics, Inc. 2009. Polyethylene Data Sheet, http://www.sdplastics.com/polyeth.html.
Sansen et al. 1990. A smart sensor for the voltammetric measurement of oxygen or glucose concentrations. Sensors and Actuators B 1:298/302.
Schmidt et al. 1993. Glucose concentration in subcutaneous extracellular space. Diabetes Care 16(5):695/700.
Schmidtke et al., Measurement and modeling of the transient difference between blood and subcutaneous glucose concentrations in the rat after injection of insulin. Proc Natl Acad Sci U S A 1998, 95, 294/299.
Schoemaker et al. 2003. The SCGM1 system: Subcutaneous continuous glucose monitoring based on microdialysis technique. Diabetes Technology & Therapeutics 5(4):599/608.
Schoonen et al. 1990 Development of a potentially wearable glucose sensor for patients with diabetes mellitus: design and in/vitro evaluation. Biosensors & Bioelectronics 5:37/46.
Service et al. 1987. Measurements of glucose control. Diabetes Care, 10: 225/237.
Service, R. F. 2002. Can sensors make a home in the body? Science 297:962/3.
Sharkawy et al. 1996. Engineering the tissue which encapsulates subcutaneous implants. I. Diffusion properties, J Biomed Mater Res, 37:401/412.
Shaw et al. "In vitro testing of a simply constructed, highly stable glucose sensor suitable for implantation in diabetic patients," Biosensors & Bioelectronics, 6:401/406 (1991).
Shichiri et al. 1989. Membrane Design for Extending the Long/Life of an Implantable Glucose Sensor. Diab. Nutr. Metab. 2:309/313.

(56) References Cited

OTHER PUBLICATIONS

Slater/Maclean et al. 2008. Accuracy of glycemic measurements in the critically ill. Diab. Thechnol. & Therapeut., 10:169/177.
Sriyudthsak et al. 1996. Enzyme/epoxy membrane based glucose analyzing system and medical applications. Biosens Bioelectron 11:735/742.
Steil et al. 2003. Determination of plasma glucose during rapid glucose excursions with a subcutaneous glucose sensor. Diabetes Technology & Therapeutics 5(1):27/31.
Stern et al., 1957. Electrochemical polarization: 1. A theoretical analysis of the shape of polarization curves, Journal of the Electrochemical Society, 104(1):56/63.
Sternberg et al. 1988. Study and Development of Multilayer Needle/type Enzyme/based Glucose Microsensors. Biosensors 4:27/40.
Sumino T. et al. 1998. Preliminary study of continuous glucose monitoring with a microdialysis technique. Proceedings of the IEEE, 20(4):1775/1778.
Takegami et al. 1992. Pervaporation of ethanol water mixtures using novel hydrophobic membranes containing polydimethylsiloxane, Journal of Membrane Science, 75(93/105).
Tanenberg et al. 2000. Continuous glucose monitoring system: A new approach to the diagnosis of diabetic gastroparesis. Diabetes Technology & Therapeutics, 2 Suppl 1:S73/80.
Tatsuma et al. 1991. Oxidase/peroxidase bilayer/modified electrodes as sensors for lactate, pyruvate, cholesteral and uric acid, Analytica Chimica Acta, 242:85/89.
Thome et al. 1995. /Abstract / Can the decrease in subcutaneous glucose concentration precede the decrease in blood glucose level? Proposition for a push/pull kinetics hypothesis, Horm. Metab. Res. 27:53.
Thome/Duret et al. 1996. Use of a subcutaneous glucose sensor to detect decreases in glucose concentration prior to observation in blood, Anal. Chem. 68:3822/3826.
Thomé/Duret et al. 1998. Continuous glucose monitoring in the free/moving rat. Metabolism, 47:799/803.
Tierney et al. 2000. The GlucoWatch® biographer: A frequent, automatic and noninvasive gluco monitor. Ann. Med. 32:632/641.
Torjman et al., Glucose monitoring in acute care: technologies on the horizon, Journal of Deabetes Science and Technology, 2(2):178/181, Mar. 2008.
Trecroci, D. 2002. A Glimpse into the Future/ Continuous Monitoring of Glucose with a Microfiber. Diabetes Interview 42/43.
Tse and Gough. 1987. Time/Dependent Inactivation of Immobilized Glucose Oxidase and Catalase. Biotechnol. Bioeng. 29:705/713.
Turner and Pickup, "Diabetes mellitus: biosensors for research and management," Biosensors, 1:85/115 (1985).
Turner et al. 1984. Carbon Monoxide: Acceptor Oxidoreductase from *Pseudomonas* Thermocarboxydovorans Strain C2 and its use in a Carbon Monoxide Sensor. Analytica Chimica Acta, 163: 161/174.
Updike et al. 1967. The enzyme electrode. Nature, 214:986/988.
Updike et al. 1988. Laboratory Evaluation of New Reusable Blood Glucose Sensor. Diabetes Care, 11:801/807.
Updike et al. 1994. Enzymatic glucose sensor: Improved long/term performance in vitro and in vivo. ASAIO Journal, 40(2):157/163.
Updike et al. 2000. A subcutaneous glucose sensor with improved longevity, dynamic range, and stability of calibration. Diabetes Care 23(2):208/214.
Vadgama, P. Nov. 1981. Enzyme electrodes as practical biosensors. Journal of Medical Engineering & Technology 5(6):293/298.
Vadgama. 1988. Diffusion limited enzyme electrodes. NATO ASI Series: Series C, Math and Phys. Sci. 226:359/377.
Wang et al. 1994. Highly Selective Membrane/Free, Mediator/Free Glucose Biosensor. Anal. Chem. 66:3600/3603.
Wang et al. 1997. Improved ruggedness for membrane/based amperometric sensors using a pulsed amperometric method. Anal Chem 69:4482/4489.

Ward et al. 2000. Understanding Spontaneous Output Fluctuations of an Amperometric Glucose Sensor: Effect of Inhalation Anesthesia and e of a Nonenzyme Containing Electrode. ASAIO Journal 540/546.
Ward et al. 2000. Rise in background current over time in a subcutaneous glucose sensor in the rabbit: Relevance to calibration and accuracy. Biosensors & Bioelectronics, 15:53/61.
Ward et al. 2002. A new amperometric glucose microsensor: In vitro and short/term in vivo evaluation. Biosensors & Bioelectronics, 17:181/189.
Wikipedia 2006. "Intravenous therapy," http://en.wikipedia.org/wiki/Intravenous_therapy, Aug. 15, 2006, 6 pp.
Wiley Electrical and Electronics Engineering Dictionary. 2004. John Wiley & Sons, Inc. pp. 141, 142, 548, 549.
Wilkins et al. 1988. The coated wire electrode glucose sensor, Horm Metab Res Suppl., 20:50/55.
Wilson et al. 2000. Enzyme/based biosensors for in vivo measurements. Chem. Rev., 100:2693/2704.
Wood, W. et al. Mar. 1990. Hermetic Sealing with Epoxy. Mechanical Engineering 1/3.
Woodward. 1982. How Fibroblasts and Giant Cells Encapsulate Implants: Considerations in Design of Glucose Sensor. Diabetes Care 5:278/281.
Worsley et al., Measurement of glucose in blood with a phenylboronic acid optical sensor, Journal of Diabetes Science and Technology, 2(2):213/220, Mar. 2008.
Wright et al., Bioelectrochemical dehalogenations via direct electrochemistry of poly(ethylene oxide)/modified myoglobin, Electrochemistry Communications 1 (1999) 603/611.
Wu et al. 1999. In situ electrochemical oxygen generation with an immunoisolation device. Annals New York Academy of Sciences, pp. 105-125.
Yamasaki et al. 1989. Direct measurement of whole blood glucose by a needle/type sensor. Clinica Chimica Acta. 93:93/98.
Yamasaki, Yoshimitsu. Sep. 1984. The development of a needle/type glucose sensor for wearable artificial endocrine pancreas. Medical Journal of Osaka University 35(1/2):25/34.
Yang et al. 1998. Development of needle/type glucose sensor with high selectivity. Science and Actuators B 46:249/256.
Yang, et al. 2004. A Comparison of Physical Properties and Fuel Cell Performance of Nafion and Zirconium Phosphate/Nafion Composite Membranes. Journal of Membrane Science 237:145/161.
Ye et al. 1993. High Current Density 'Wired' Quinoprotein Glucose Dehydrogenase Electrode. Anal. Chem. 65:238/241.
Zethelius et al. 2008. Use of multiple biomarkers to improve the prediction of death from cardiovascular causes. N. Engl. J. Med., 358: 2107/2116.
Zhang et al (1993). Electrochemical oxidation of H2O2 on Pt and Pt + Ir electrodes in physiological buffer and its applicability to H2O2/based biosensors. J. Electroanal. Chem., 345:253/271.
Zhang et al. 1993. In vitro and in vivo evaluation of oxygen effects on a glucose oxidase based implantable glucose sensor. Analytica Chimica Acta, 281:513/520.
Zhang et al. 1994. Elimination of the acetaminophen interference in an implantable glucose sensor. Analytical Chemistry 66(7):1183/1188.
Zhu et al. (1994). "Fabrication and characterization of glucose sensors based on a microarray H2O2 electrode." Biosensors & Bioelectronics, 9: 295/300.
NewsRx (Aug. 3, 2003). Medical Letter on the CDC & FDA via NewsRx.com. "Glucose Monitoring: FDA OKs new device to manage diabetes".
Renard, Eric (2002), Current Opinion in Pharmacology 2:708-716. Implantable closed-loop glucose and insulin delivery: the future for insulin pump therapy.

\* cited by examiner

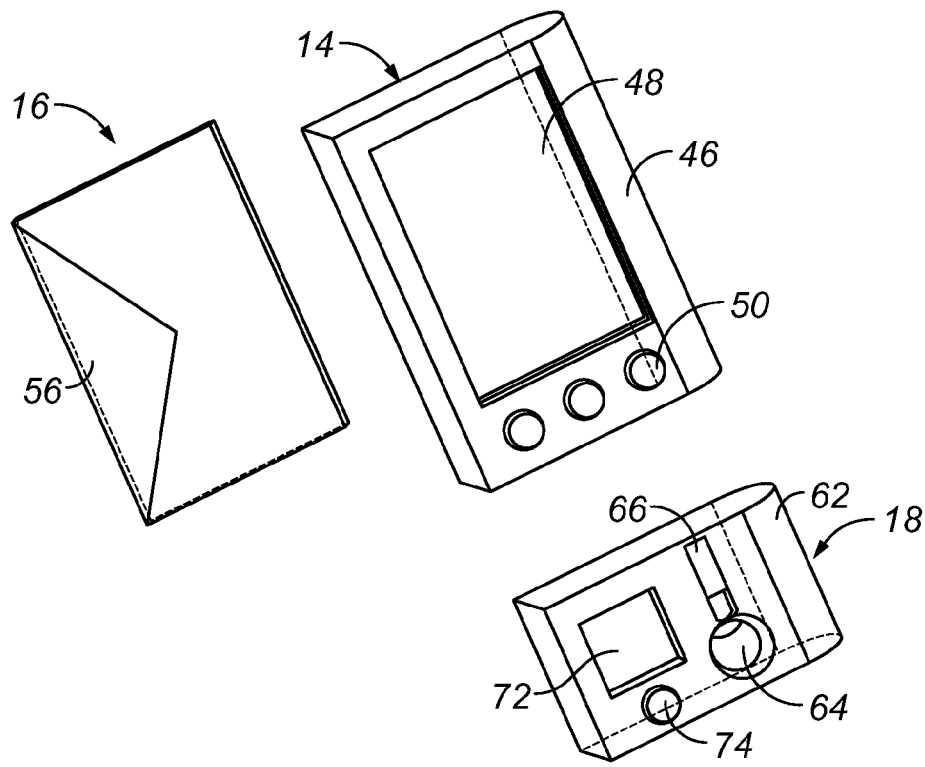
FIG. 5A
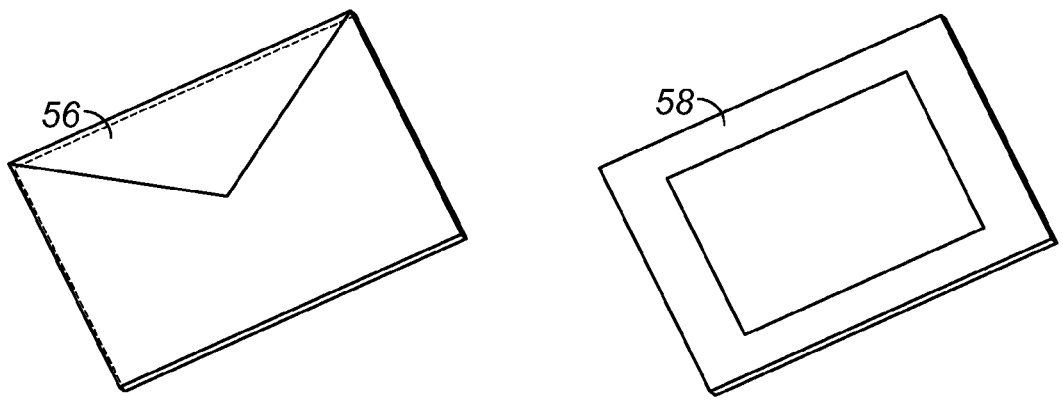
FIG. 5B  FIG. 5C

INTEGRATED DELIVERY DEVICE FOR CONTINUOUS GLUCOSE SENSOR

CROSS-REFERENCE TO RELATED APPLICATIONS

This application is a continuation of U.S. application Ser. No. 13/180,396 filed Jul. 11, 2011, which is a continuation of U.S. application Ser. No. 12/536,852 filed Aug. 6, 2009, now U.S. Pat. No. 7,976,492, which is a divisional of U.S. application Ser. No. 10/789,359 filed Feb. 26, 2004, now U.S. Pat. No. 7,591,801, each of which is incorporated by reference herein in its entirety, and each of which is hereby made a part of this specification.

FIELD OF THE INVENTION

The present invention relates generally to systems and methods monitoring glucose in a host. More particularly, the present invention relates to an integrated medicament delivery device and continuous glucose sensor.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which may cause an array of physiological derangements (for example, kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically comprises uncomfortable finger pricking methods. Due to the lack of comfort and convenience, a diabetic will normally only measure his or her glucose level two to four times per day. Unfortunately, these time intervals are so far spread apart that the diabetic will likely find out too late, sometimes incurring dangerous side effects, of a hyper- or hypo-glycemic condition. In fact, it is not only unlikely that a diabetic will take a timely SMBG value, but the diabetic will not know if their blood glucose value is going up (higher) or down (lower) based on conventional methods, inhibiting their ability to make educated insulin therapy decisions.

Home diabetes therapy requires personal discipline of the user, appropriate education from a doctor, proactive behavior under sometimes-adverse situations, patient calculations to determine appropriate therapy decisions, including types and amounts of administration of insulin and glucose into his or her system, and is subject to human error. Technologies are needed that ease the burdens faced by diabetic patients, simplify the processes involved in treating the disease, and minimize user error which may cause unnecessarily dangerous situations in some circumstances.

SUMMARY OF THE INVENTION

In a first embodiment, a method for treating diabetes with an integrated glucose sensor and medicament delivery device is provided, including: receiving in a receiver a data stream from a glucose sensor, including one or more sensor data points; calculating medicament therapy responsive to the one or more sensor data points; validating the calculated therapy based on at least one of data input into the receiver and data obtained from an integrated single point glucose monitor; and outputting validated information reflective of the therapy recommendations.

In an aspect of the first embodiment, the therapy validation is configured to trigger a fail-safe module, if the validation fails, wherein the user must confirm a therapy decision prior to outputting therapy recommendations.

In an aspect of the first embodiment, the output step includes outputting the sensor therapy recommendations to a user interface.

In an aspect of the first embodiment, the output step includes displaying the sensor therapy recommendations on the user interface of at least one of a receiver and a medicament delivery device.

In an aspect of the first embodiment, the output step includes transmitting the therapy recommendations to a medicament delivery device.

In an aspect of the first embodiment, the output step includes delivering the recommended therapy via an automated delivery device.

In a second embodiment, a method for treating diabetes in a host with an integrated glucose sensor and medicament delivery device is provided, including: receiving in a receiver medicament delivery data responsive to medicament delivery from a medicament delivery device; receiving in a receiver a data stream from a glucose sensor, including one or more sensor data points for a time period before and after the medicament delivery; determining a host's metabolic response to the medicament delivery; receiving a subsequent data stream from the glucose sensor including one or more sensor data points; and calculating medicament therapy responsive to the host's metabolic response to the medicament delivery.

In an aspect of the second embodiment, the host's metabolic response is calculated using a pattern recognition algorithm.

In an aspect of the second embodiment, the step of determining a host's metabolic response to medicament delivery is repeated when the receiver receives additional medicament delivery data.

In an aspect of the second embodiment, the host's metabolic response iteratively determined for a time period exceeding one week.

In a third embodiment, a method for estimating glucose levels from an integrated glucose sensor and medicament delivery device is provided, including: receiving in a receiver a data stream from a glucose sensor, including one or more sensor data points; receiving in the receiver medicament delivery data responsive to medicament delivery from a medicament delivery device; evaluating medicament delivery data with glucose sensor data corresponding to delivery and release times of the medicament delivery data to determine individual metabolic patterns associated with medicament delivery; and estimating glucose values responsive to individual metabolic patterns associated with the medicament delivery.

In an aspect of the third embodiment, the individual's metabolic patterns associated with medicament delivery are calculated using a pattern recognition algorithm.

In an aspect of the third embodiment, the step of determining the individual's metabolic patterns to medicament delivery is repeated when the receiver receives additional medicament delivery data.

In an aspect of the third embodiment, the individual's metabolic patterns are iteratively determined for a time period exceeding one week.

In a fourth embodiment, an integrated system for monitoring and treating diabetes is provided, including: a glucose sensor, wherein the glucose sensor substantially continuously measures glucose in a host for a period exceeding one week, and outputs a data stream, including one or more sensor data points; a receiver operably connected to the glucose sensor, wherein the receiver is configured to receive the data stream; and a medicament delivery device, wherein the delivery device is at least one of physically and operably connected to the receiver.

In an aspect of the fourth embodiment, the glucose sensor includes an implantable glucose sensor.

In an aspect of the fourth embodiment, the glucose sensor includes a long-term subcutaneously implantable glucose sensor.

In an aspect of the fourth embodiment, the medicament delivery device includes a syringe detachably connectable to the receiver.

In an aspect of the fourth embodiment, the medicament delivery device includes one or more transdermal patches detachably connectable to the receiver.

In an aspect of the fourth embodiment, the medicament delivery device includes an inhaler or spray delivery device detachably connectable to the receiver.

In an aspect of the fourth embodiment, the medicament delivery device includes a pen or jet-type injector.

In an aspect of the fourth embodiment, the medicament delivery device includes a transdermal pump.

In an aspect of the fourth embodiment, the medicament delivery device includes an implantable pump.

In an aspect of the fourth embodiment, the medicament delivery device includes a manual implantable pump.

In an aspect of the fourth embodiment, the medicament delivery device includes a cell transplantation device.

In an aspect of the fourth embodiment, the medicament delivery device is detachably connected to the receiver.

In an aspect of the fourth embodiment, the medicament delivery device is operably connected to the receiver by a wireless connection.

In an aspect of the fourth embodiment, the medicament delivery device is operably connected by a wired connection.

In an aspect of the fourth embodiment, further including a single point glucose monitor, wherein the single point glucose monitor is at least one of physically and operably connected to the receiver.

In an aspect of the fourth embodiment, the glucose sensor includes an enzyme membrane system for electrochemical detection of glucose the single point glucose monitor includes an enzyme membrane system for electrochemical detection of glucose.

In an aspect of the fourth embodiment, the receiver includes a microprocessor, and wherein the microprocessor includes programming for calculating and outputting medicament delivery instructions.

In an aspect of the fourth embodiment, the microprocessor further includes a validation module that validates the medicament delivery instructions prior to outputting the instructions.

In an aspect of the fourth embodiment, the receiver is configured to receive medicament delivery data responsive to medicament delivery for a first time period from the medicament delivery device.

In an aspect of the fourth embodiment, the receiver includes a microprocessor, and wherein the microprocessor includes programming to determine a host's metabolic response to the medicament delivery by evaluating the sensor data points substantially corresponding to delivery and release of the medicament delivery for the first time period.

In an aspect of the fourth embodiment, the microprocessor calculates medicament therapy for a second time period responsive to sensor data and the host's metabolic response to the medicament delivery.

In an aspect of the fourth embodiment, the microprocessor includes programming to estimate glucose values responsive to glucose sensor data and host's metabolic response.

BRIEF DESCRIPTION OF THE DRAWINGS

FIGS. 5A to 5C are perspective views of an integrated system in one embodiment, wherein a receiver is integrated with a medicament delivery device in the form of one or more transdermal patches housed within a holder, and optionally includes a single point glucose monitor.

DETAILED DESCRIPTION OF THE PREFERRED EMBODIMENT

Figure 1:
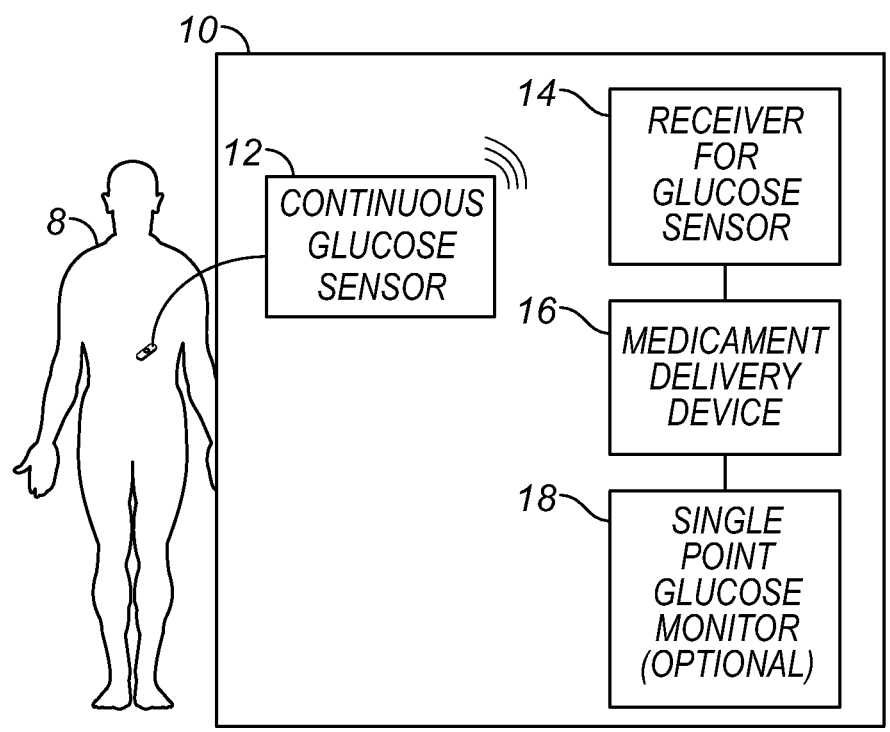
FIG. 1 is a block diagram of an integrated system of the preferred embodiments, including a continuous glucose sensor, a receiver for processing and displaying sensor data, a medicament delivery device, and an optional single point glucose-monitoring device.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

DEFINITIONS

In order to facilitate an understanding of the disclosed invention, a number of terms are defined below.

The term "continuous glucose sensor," as used herein, is a broad term and are used in its ordinary sense, including, but not limited to, a device that continuously or continually measures glucose concentration, for example, at time intervals ranging from fractions of a second up to, for example, 1, 2, or 5 minutes, or longer. It should be understood that continual or continuous glucose sensors can continually measure glucose concentration without requiring user initiation and/or interaction for each measurement, such as described with reference to U.S. Pat. No. 6,001,067, for example.

The phrase "continuous glucose sensing," as used herein, is a broad term and is used in its ordinary sense, including, but not limited to, the period in which monitoring of plasma glucose concentration is continuously or continually performed, for example, at time intervals ranging from fractions of a second up to, for example, 1, 2, or 5 minutes, or longer.

The term "biological sample," as used herein, is a broad term and is used in its ordinary sense, including, but not limited to, sample of a host body, for example, blood, interstitial fluid, spinal fluid, saliva, urine, tears, sweat, or the like.

The term "host," as used herein, is a broad term and is used in its ordinary sense, including, but not limited to, mammals such as humans.

The term "biointerface membrane," as used herein, is a broad term and is used in its ordinary sense, including, without limitation, a permeable or semi-permeable membrane that can include two or more domains and is typically constructed of materials of a few microns thickness or more, which can be placed over the sensing region to keep host cells (for example, macrophages) from gaining proximity to, and thereby damaging the sensing membrane or forming a barrier cell layer and interfering with the transport of glucose across the tissue-device interface.

The term "sensing membrane," as used herein, is a broad term and is used in its ordinary sense, including, without limitation, a permeable or semi-permeable membrane that can be comprised of two or more domains and is typically constructed of materials of a few microns thickness or more, which are permeable to oxygen and are optionally permeable to glucose. In one example, the sensing membrane comprises an immobilized glucose oxidase enzyme, which enables an electrochemical reaction to occur to measure a concentration of glucose.

The term "domain," as used herein is a broad term and is used in its ordinary sense, including, without limitation, regions of a membrane that can be layers, uniform or non-uniform gradients (for example, anisotropic), functional aspects of a material, or provided as portions of the membrane.

As used herein, the term "copolymer," as used herein, is a broad term and is used in its ordinary sense, including, without limitation, polymers having two or more different repeat units and includes copolymers, terpolymers, tetrapolymers, etc.

The term "sensing region," as used herein, is a broad term and is used in its ordinary sense, including, without limitation, the region of a monitoring device responsible for the detection of a particular glucose. In one embodiment, the sensing region generally comprises a non-conductive body, a working electrode (anode), a reference electrode and a counter electrode (cathode) passing through and secured within the body forming an electrochemically reactive surface at one location on the body and an electronic connection at another location on the body, and a sensing membrane affixed to the body and covering the electrochemically reactive surface. The counter electrode typically has a greater electrochemically reactive surface area than the working electrode. During general operation of the sensor a biological sample (for example, blood or interstitial fluid) or a portion thereof contacts (for example, directly or after passage through one or more domains of the sensing membrane) an enzyme (for example, glucose oxidase); the reaction of the biological sample (or portion thereof) results in the formation of reaction products that allow a determination of the glucose level in the biological sample.

The term "electrochemically reactive surface," as used herein, is a broad term and is used in its ordinary sense, including, without limitation, the surface of an electrode where an electrochemical reaction takes place. In the case of the working electrode, the hydrogen peroxide produced by the enzyme catalyzed reaction of the glucose being detected reacts creating a measurable electronic current (for example, detection of glucose utilizing glucose oxidase produces $H_2O_2$ as a by product, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species (for example, $O_2$) is reduced at the electrode surface in order to balance the current being generated by the working electrode.

The term "electrochemical cell," as used herein, is a broad term and is used in its ordinary sense, including, without limitation, a device in which chemical energy is converted to electrical energy. Such a cell typically consists of two or more electrodes held apart from each other and in contact with an electrolyte solution. Connection of the electrodes to a source of direct electric current renders one of them negatively charged and the other positively charged. Positive ions in the electrolyte migrate to the negative electrode (cathode) and there combine with one or more electrons, losing part or all of their charge and becoming new ions having lower charge or neutral atoms or molecules; at the same time, negative ions migrate to the positive electrode (anode) and transfer one or more electrons to it, also becoming new ions or neutral particles. The overall effect of the two processes is the transfer of electrons from the negative ions to the positive ions, a chemical reaction.

The term "proximal" as used herein, is a broad term and is used in its ordinary sense, including, without limitation, near to a point of reference such as an origin or a point of attachment. For example, in some embodiments of a sensing membrane that covers an electrochemically reactive surface, the electrolyte domain is located more proximal to the electrochemically reactive surface than the interference domain.

The term "distal" as used herein, is a broad term and is used in its ordinary sense, including, without limitation, spaced relatively far from a point of reference, such as an origin or a point of attachment. For example, in some embodiments of a sensing membrane that covers an electrochemically reactive surface, a resistance domain is located more distal to the electrochemically reactive surfaces than the enzyme domain.

The term "substantially" as used herein, is a broad term and is used in its ordinary sense, including, without limitation, being largely but not necessarily wholly that which is specified.

The term "microprocessor," as used herein, is a broad term and is used in its ordinary sense, including, without limitation, a computer system or processor designed to perform arithmetic and logic operations using logic circuitry that responds to and processes the basic instructions that drive a computer.

The term "ROM," as used herein, is a broad term and is used in its ordinary sense, including, but not limited to, read-only memory, which is a type of data storage device manufactured with fixed contents. ROM is broad enough to include EEPROM, for example, which is electrically erasable programmable read-only memory (ROM).

The term "RAM," as used herein, is a broad term and is used in its ordinary sense, including, but not limited to, a data storage device for which the order of access to different locations does not affect the speed of access. RAM is broad enough to include SRAM, for example, which is static random access memory that retains data bits in its memory as long as power is being supplied.

The term "A/D Converter," as used herein, is a broad term and is used in its ordinary sense, including, but not limited to, hardware and/or software that converts analog electrical signals into corresponding digital signals.

The term "RF transceiver," as used herein, is a broad term and is used in its ordinary sense, including, but not limited to, a radio frequency transmitter and/or receiver for transmitting and/or receiving signals.

The terms "raw data stream" and "data stream," as used herein, are broad terms and are used in their ordinary sense, including, but not limited to, an analog or digital signal directly related to the analyte concentration measured by the analyte sensor. In one example, the raw data stream is digital data in "counts" converted by an A/D converter from an analog signal (for example, voltage or amps) representative of an analyte concentration. The terms broadly encompass a plurality of time spaced data points from a substantially continuous analyte sensor, which comprises individual measurements taken at time intervals ranging from fractions of a second up to, for example, 1, 2, or 5 minutes or longer.

The term "counts," as used herein, is a broad term and is used in its ordinary sense, including, but not limited to, a unit of measurement of a digital signal. In one example, a raw data stream measured in counts is directly related to a voltage (for example, converted by an A/D converter), which is directly related to current from a working electrode.

The term "electronic circuitry," as used herein, is a broad term and is used in its ordinary sense, including, but not limited to, the components (for example, hardware and/or software) of a device configured to process data. In the case of an analyte sensor, the data includes biological information obtained by a sensor regarding the concentration of the analyte in a biological fluid. U.S. Pat. Nos. 4,757,022, 5,497,772 and 4,787,398, which are hereby incorporated by reference in their entirety, describe suitable electronic circuits that can be utilized with devices of certain embodiments.

The term "potentiostat," as used herein, is a broad term and is used in its ordinary sense, including, but not limited to, an electrical system that controls the potential between the working and reference electrodes of a three-electrode cell at a preset value. The potentiostat forces whatever current is necessary to flow between the working and counter electrodes to keep the desired potential, as long as the needed cell voltage and current do not exceed the compliance limits of the potentiostat.

The terms "operably connected" and "operably linked," as used herein, are broad terms and are used in their ordinary sense, including, but not limited to, one or more components being linked to another component(s) in a manner that allows transmission of signals between the components. For example, one or more electrodes can be used to detect the amount of glucose in a sample and convert that information into a signal; the signal can then be transmitted to an electronic circuit. In this case, the electrode is "operably linked" to the electronic circuit. These terms are broad enough to include wired and wireless connectivity.

The term "algorithmically smoothed," as used herein, is a broad term and is used in its ordinary sense, including, but not limited to, modification of a set of data to make it smoother and more continuous and remove or diminish outlying points, for example, by performing a moving average of the raw data stream.

The term "algorithm," as used herein, is a broad term and is used in its ordinary sense, including, but not limited to, the computational processes (for example, programs) involved in transforming information from one state to another, for example using computer processing.

The term "regression," as used herein, is a broad term and is used in its ordinary sense, including, but not limited to, finding a line in which a set of data has a minimal measurement (for example, deviation) from that line. Regression can be linear, non-linear, first order, second order, and so forth. One example of regression is least squares regression.

The terms "recursive filter" and "auto-regressive algorithm," as used herein, are broad terms and are used in their ordinary sense, including, but not limited to, an equation in which previous averages are part of the next filtered output. More particularly, the generation of a series of observations whereby the value of each observation is partly dependent on the values of those that have immediately preceded it. One example is a regression structure in which lagged response values assume the role of the independent variables.

The terms "velocity" and "rate of change," as used herein, are broad terms and are used in their ordinary sense, including, but not limited to, time rate of change; the amount of change divided by the time required for the change. In one embodiment, these terms refer to the rate of increase or decrease in an analyte for a certain time period.

The term "acceleration" as used herein, is a broad term and is used in its ordinary sense, including, but not limited to, the rate of change of velocity with respect to time. This term is broad enough to include deceleration.

The term "clinical risk," as used herein, is a broad term and is used in its ordinary sense, including, but not limited to, an identified danger or potential risk to the health of a patient based on a measured or estimated analyte concentration, its rate of change, and/or its acceleration.

The term "clinically acceptable," as used herein, is a broad term and is used in its ordinary sense, including, but not limited to, an analyte concentration, rate of change, and/or acceleration associated with that measured analyte that is considered to be safe for a patient.

The term "time period," as used herein, is a broad term and is used in its ordinary sense, including, but not limited to, an amount of time including a single point in time and a path (for example, range of time) that extends from a first point in time to a second point in time.

The term "measured analyte values," as used herein, is a broad term and is used in its ordinary sense, including, but not limited to, an analyte value or set of analyte values for a time period for which analyte data has been measured by an analyte sensor. The term is broad enough to include data from the analyte sensor before or after data processing in the sensor and/or receiver (for example, data smoothing, calibration, or the like).

The term "alarm," as used herein, is a broad term and is used in its ordinary sense, including, but not limited to, audible, visual, or tactile signal that are triggered in response to detection of clinical risk to a patient. In one embodiment, hyperglycemic and hypoglycemic alarms are triggered when present or future clinical danger is assessed based on continuous analyte data.

The term "computer," as used herein, is broad term and is used in its ordinary sense, including, but not limited to, machine that can be programmed to manipulate data.

The term "modem," as used herein, is a broad term and is used in its ordinary sense, including, but not limited to, an electronic device for converting between serial data from a computer and an audio signal suitable for transmission over a telecommunications connection to another modem.

Overview

FIG. 1 is a block diagram of an integrated system 10 of the preferred embodiments, including a continuous glucose sensor 12, a receiver 14 for processing and displaying sensor data, a medicament delivery device 16, and optionally a single point glucose-monitoring device 18. The integrated diabetes management system 10 of the preferred embodiments provides improved convenience and accuracy thus affording a diabetic patient 8 with improved convenience, functionality, and safety in the care of their disease.

FIG. 1 shows a continuous glucose sensor 12 that measures a concentration of glucose or a substance indicative of the concentration or presence of the glucose. In some embodiments, the glucose sensor 12 is an invasive, minimally invasive, or non-invasive device, for example a subcutaneous, transdermal, or intravascular device. In some embodiments, the sensor 12 may analyze a plurality of intermittent biological samples. The glucose sensor may use any method of glucose-measurement, including enzymatic, chemical, physical, electrochemical, spectrophotometric, polarimetric, calorimetric, radiometric, or the like. In alternative embodiments, the sensor 12 may be any sensor capable of determining the level of an analyte in the body, for example oxygen, lactase, insulin, hormones, cholesterol, medicaments, viruses, or the like. The glucose sensor 12 uses any known method to provide an output signal indicative of the concentration of the glucose. The output signal is typically a raw data stream that is used to provide a useful value of the measured glucose concentration to a patient or doctor, for example.

Accordingly, a receiver 14 is provided that receives and processes the raw data stream, including calibrating, validating, and displaying meaningful glucose values to a patient, such as described in more detail below. A medicament delivery device 16 is further provided as a part of the integrated system 10. In some embodiments, the medicament delivery device 16 is a manual delivery device, for example a syringe, inhaler, or transdermal patch, which is manually integrated with the receiver 14. In some embodiments, the medicament delivery device 16 is a semi-automated delivery device, for example a pen or jet-type injector, an inhaler, a spray, or pump, which provides a semi-automated integration with the receiver 14. In some embodiments, the medicament delivery device 16 is an automated delivery device, for example a transcutaneous or implantable pump system, which provides an automated integration with the receiver 14. In some embodiments, an optional single point glucose monitor 18 is further provided as a part of the integrated system 10, for example a self-monitoring blood glucose meter (SMBG), non-invasive glucose meter, or the like.

Conventionally, each of these devices separately provides valuable information and or services to diabetic patients. Thus, a typical diabetic patient has numerous individual devices, which they track and consider separately. In some cases, the amount of information provided by these individual devices may require complex understanding of the nuances and implications of each device, for example types and amounts of insulin to deliver. Typically, each individual device is a silo of information that functions as well as the data provided therein, therefore when the devices are able to communicate with each other, enhanced functionality and safety may be realized. For example, when a continuous glucose monitor functions alone (for example, without data other than that which was gathered by the device), sudden changes in glucose level are tracked, but may not be fully understood, predicted, preempted, or otherwise considered in the processing of the sensor data; however, if the continuous glucose sensor were provided with information about time, amount, and type of insulin injections, calories consumed, time or day, meal time, or like, more meaningful, accurate and useful glucose estimation, prediction, and other such processing can be provided, such as described in more detail herein. By integrating these devices, the information from each component can be leveraged to increase the intelligence, benefit provided, convenience, safety, and functionality of the continuous glucose sensor and other integrated components. Therefore, it would be advantageous to provide a device that aids the diabetic patient in integrating these individual devices in the treatment of his/her disease.

Glucose Sensor

Figure 2:
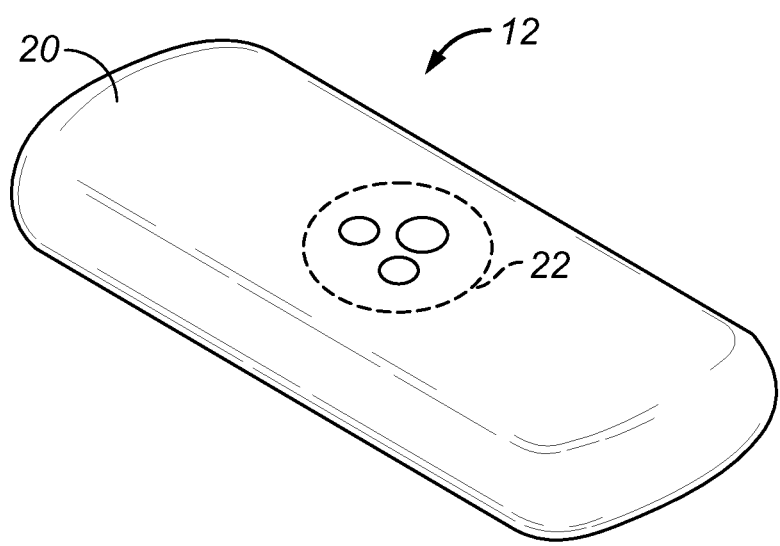
FIG. 2 is a perspective view of a continuous glucose sensor in one embodiment.
Figure 3:
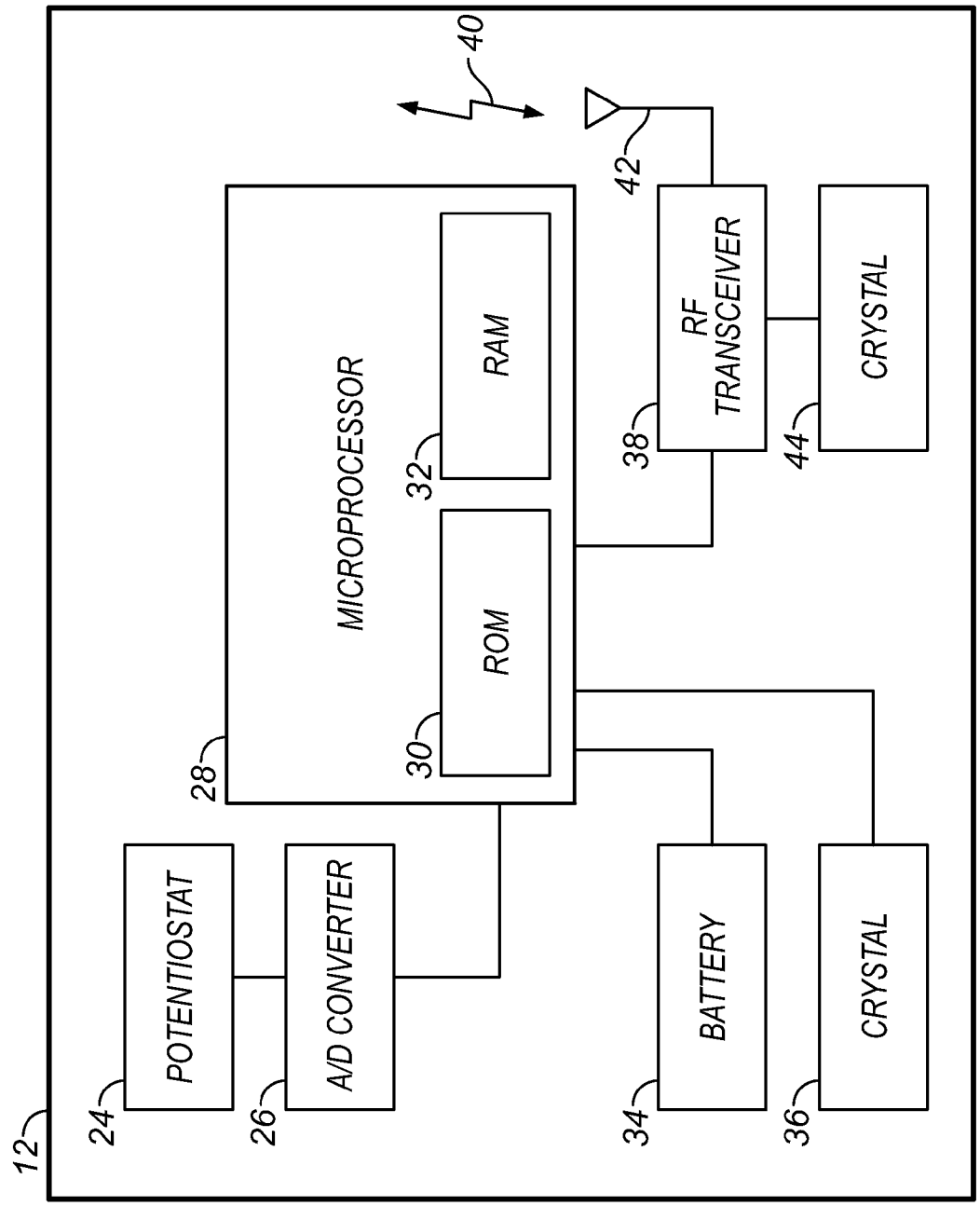
FIG. 3 is a block diagram of the electronics associated with a continuous glucose sensor in one embodiment.

FIG. 2 is a perspective view of one embodiment of a continuous glucose sensor 12. In this embodiment, a body 20 and a sensing region 22 house the electrodes and sensor electronics (FIG. 3). The three electrodes within the sensing region are operably connected to the sensor electronics (FIG. 3) and are covered by a sensing membrane and a biointerface membrane (not shown), which are described in more detail below.

The body 20 is preferably formed from epoxy molded around the sensor electronics, however the body may be formed from a variety of materials, including metals, ceramics, plastics, or composites thereof. Co-pending U.S. patent application Ser. No. 10/646,333, entitled, "Optimized Sensor Geometry for an Implantable Glucose Sensor" discloses suitable configurations suitable for the body 20, and is incorporated by reference in its entirety.

In one embodiment, the sensing region 22 comprises three electrodes including a platinum working electrode, a platinum counter electrode, and a silver/silver chloride reference electrode, for example. However a variety of electrode materials and configurations may be used with the implantable glucose sensor of the preferred embodiments. The top ends of the electrodes are in contact with an electrolyte phase (not shown), which is a free-flowing fluid phase disposed between the sensing membrane and the electrodes. In one embodiment, the counter electrode is provided to balance the current generated by the species being measured at the working electrode. In the case of a glucose oxidase based glucose sensor, the species being measured at the working electrode is $H_2O_2$. Glucose oxidase catalyzes the conversion of oxygen and glucose to hydrogen peroxide and gluconate according to the following reaction:

$$Glucose + O_2 \rightarrow Gluconate + H_2O_2$$

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons ($2H^+$), two electrons ($2e^-$), and one oxygen molecule ($O_2$).

In one embodiment, a potentiostat (FIG. 3) is employed to monitor the electrochemical reaction at the electroactive surface(s). The potentiostat applies a constant potential to the working and reference electrodes to determine a current value. The current that is produced at the working electrode (and flows through the circuitry to the counter electrode) is substantially proportional to the amount of $H_2O_2$ that diffuses to the working electrode. Accordingly, a raw signal can be produced that is representative of the concentration of glucose in the user's body, and therefore can be utilized to estimate a meaningful glucose value.

In some embodiments, the sensing membrane includes an enzyme, for example, glucose oxidase, and covers the electrolyte phase. In one embodiment, the sensing membrane generally includes a resistance domain most distal from the electrochemically reactive surfaces, an enzyme domain less distal from the electrochemically reactive surfaces than the resistance domain, and an electrolyte domain adjacent to the electrochemically reactive surfaces. However, it is understood that a sensing membrane modified for other devices, for example, by including fewer or additional domains, is within the scope of the preferred embodiments. Co-pending U.S. patent application Ser. No. 09/916,711, entitled, "SENSOR HEAD FOR USE WITH IMPLANTABLE DEVICES," which is incorporated herein by reference in its entirety, describes membranes that can be used in some embodiments of the sensing membrane. It is noted that in some embodiments, the sensing membrane may additionally include an interference domain that blocks some interfering species; such as described in the above-cited co-pending patent application. Co-pending U.S. patent application Ser. No. 10/695,636, entitled, "SILICONE COMPOSITION FOR BIOCOMPATIBLE MEMBRANE" also describes membranes that may be used for the sensing membrane of the preferred embodiments, and is incorporated herein by reference in its entirety.

Preferably, the biointerface membrane supports tissue ingrowth, serves to interfere with the formation of a barrier cell layer, and protects the sensitive regions of the device from host inflammatory response. In one embodiment, the biointerface membrane generally includes a cell disruptive domain most distal from the electrochemically reactive surfaces and a cell impermeable domain less distal from the electrochemically reactive surfaces than the cell disruptive domain. The cell disruptive domain is preferably designed to support tissue ingrowth, disrupt contractile forces typically found in a foreign body response, encourage vascularity within the membrane, and disrupt the formation of a barrier cell layer. The cell impermeable domain is preferably resistant to cellular attachment, impermeable to cells, and composed of a biostable material. Copending U.S. patent application Ser. No. 09/916,386, entitled, "MEMBRANE FOR USE WITH IMPLANTABLE DEVICES," U.S. patent application Ser. No. 10/647,065, entitled, "POROUS MEMBRANES FOR USE WITH IMPLANTABLE DEVICES," and U.S. Provisional Patent Application 60/544,722, filed Feb. 12, 2004 entitled, "BIOINTERFACE WITH INTEGRATED MACRO- AND MICRO-ARCHITECTURE," describe biointerface membranes that may be used in conjunction with the preferred embodiments, and are incorporated herein by reference in their entirety. It is noted that the preferred embodiments may be used with a short term (for example, 1 to 7 day sensor), in which case a biointerface membrane may not be required. It is noted that the biointerface membranes described herein provide a continuous glucose sensor that has a useable life of greater than about one week, greater than about one month, greater than about three months, or greater than about one year, herein after referred to as "long-term."

In some embodiments, the domains of the biointerface and sensing membranes are formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones and block copolymers thereof including, for example, di-block, tri-block, alternating, random and graft copolymers.

FIG. 3 is a block diagram that illustrates the electronics associated with a continuous glucose sensor 12 in one embodiment. In this embodiment, a potentiostat 24 is shown, which is operably connected to electrodes (FIG. 2) to obtain a current value, and includes a resistor (not shown) that translates the current into voltage. An A/D converter 26 digitizes the analog signal into "counts" for processing. Accordingly, the resulting raw data stream in counts is directly related to the current measured by the potentiostat 24.

A microprocessor 28 is the central control unit that houses ROM 30 and RAM 32, and controls the processing of the sensor electronics. It is noted that certain alternative embodiments can utilize a computer system other than a microprocessor to process data as described herein. In some alternative embodiments, an application-specific integrated circuit (ASIC) can be used for some or all the sensor's central processing as is appreciated by one skilled in the art. The ROM 30 provides semi-permanent storage of data, for example, storing data such as sensor identifier (ID) and programming to process data streams (for example, programming for data smoothing and/or replacement of signal artifacts such as described in copending U.S. patent application entitled, "SYSTEMS AND METHODS FOR REPLACING SIGNAL ARTIFACTS IN A GLUCOSE SENSOR DATA STREAM," filed Aug. 22, 2003). The RAM 32 can be used for the system's cache memory, for example for temporarily storing recent sensor data. In some alternative embodiments, memory storage components comparable to ROM 30 and RAM 32 may be used instead of or in addition to the preferred hardware, such as dynamic RAM, static-RAM, non-static RAM, EEPROM, rewritable ROMs, flash memory, or the like.

A battery 34 is operably connected to the microprocessor 28 and provides the necessary power for the sensor 12. In one embodiment, the battery is a Lithium Manganese Dioxide battery, however any appropriately sized and powered battery can be used (for example, AAA, Nickel-cadmium, Zinc-carbon, Alkaline, Lithium, Nickel-metal hydride, Lithium-ion, Zinc-air, Zinc-mercury oxide, Silver-zinc, and/or hermetically-sealed). In some embodiments the battery is rechargeable. In some embodiments, a plurality of batteries can be used to power the system. In yet other embodiments, the receiver can be transcutaneously powered via an inductive coupling, for example. A Quartz Crystal 36 is operably connected to the microprocessor 28 and maintains system time for the computer system as a whole.

An RF Transceiver 38 is operably connected to the microprocessor 28 and transmits the sensor data from the sensor 12 to a receiver within a wireless transmission 40 via antenna 42. Although an RF transceiver is shown here, some other embodiments can include a wired rather than wireless connection to the receiver. A second quartz crystal 44 provides the system time for synchronizing the data transmissions from the RF transceiver. It is noted that the transceiver 38 can be substituted with a transmitter in other embodiments. In some alternative embodiments other mechanisms such as optical, infrared radiation (IR), ultrasonic, or the like may be used to transmit and/or receive data.

In one alternative embodiment, the continuous glucose sensor comprises a transcutaneous sensor such as described in U.S. Pat. No. 6,565,509 to Say et al. In another alternative embodiment, the continuous glucose sensor comprises a subcutaneous sensor such as described with reference to U.S. Pat. No. 6,579,690 to Bonnecaze et al. and U.S. Pat. No. 6,484,046 to Say et al. In another alternative embodiment, the continuous glucose sensor comprises a refillable subcutaneous sensor such as described with reference to U.S. Pat. No. 6,512,939 to Colvin et al. In another alternative embodiment, the continuous glucose sensor comprises an intravascular sensor such as described with reference to U.S. Pat. No. 6,477,395 to Schulman et al. In another alternative embodiment, the continuous glucose sensor comprises an intravascular sensor such as described with reference to U.S. Pat. No. 6,424,847 to Mastrototaro et al. All of the above patents are incorporated in their entirety herein by reference. In general, it should be understood that the disclosed embodiments are applicable to a variety of continuous glucose sensor configurations.

Receiver

Figure 9:
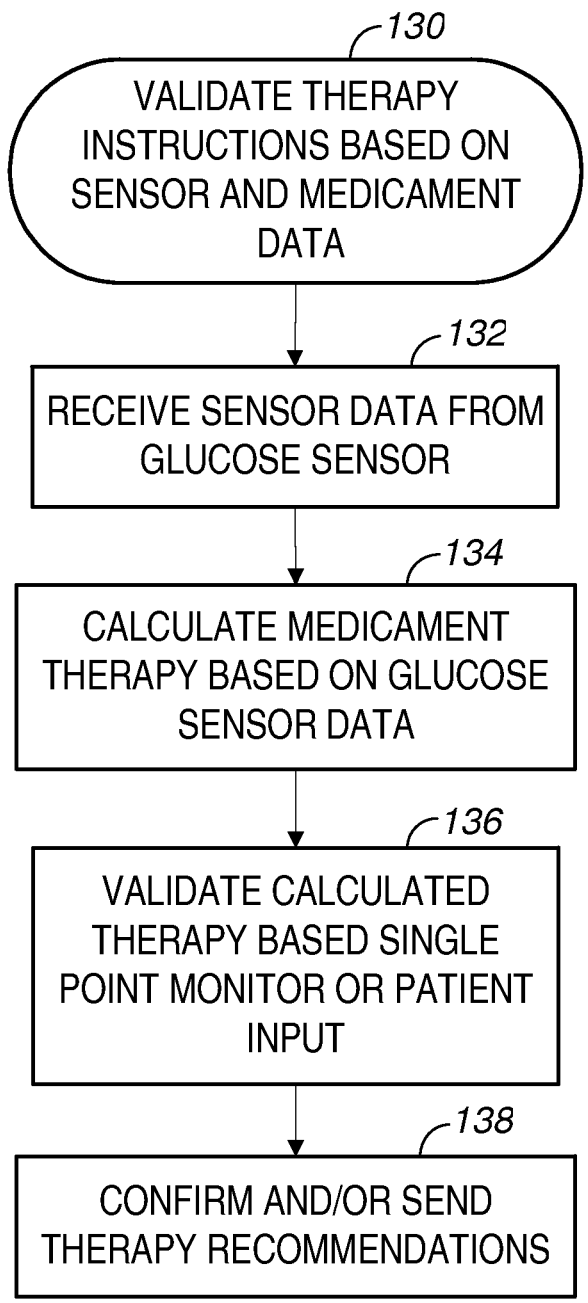
FIG. 9 is a flow chart that illustrates the process of validating therapy instructions prior to medicament delivery in one embodiment.
Figure 10:
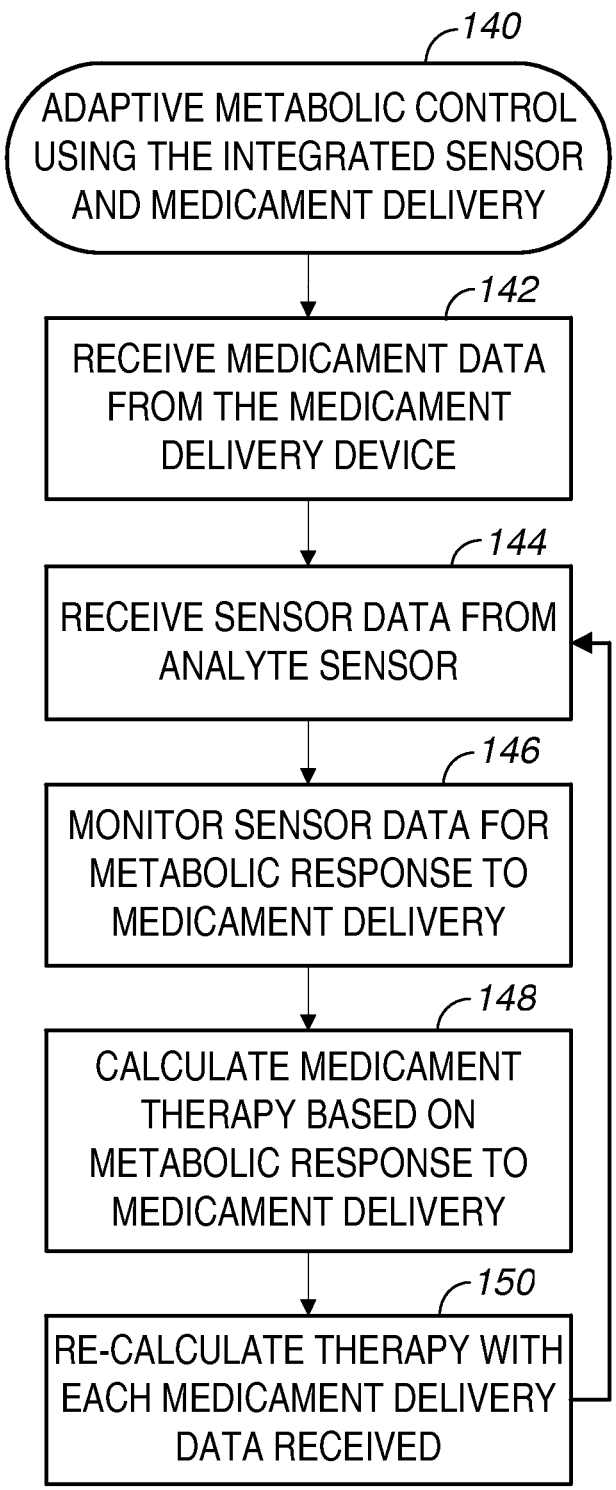
FIG. 10 is a flow chart that illustrates the process of providing adaptive metabolic control using an integrated sensor and medicament delivery device in one embodiment.
Figure 11:
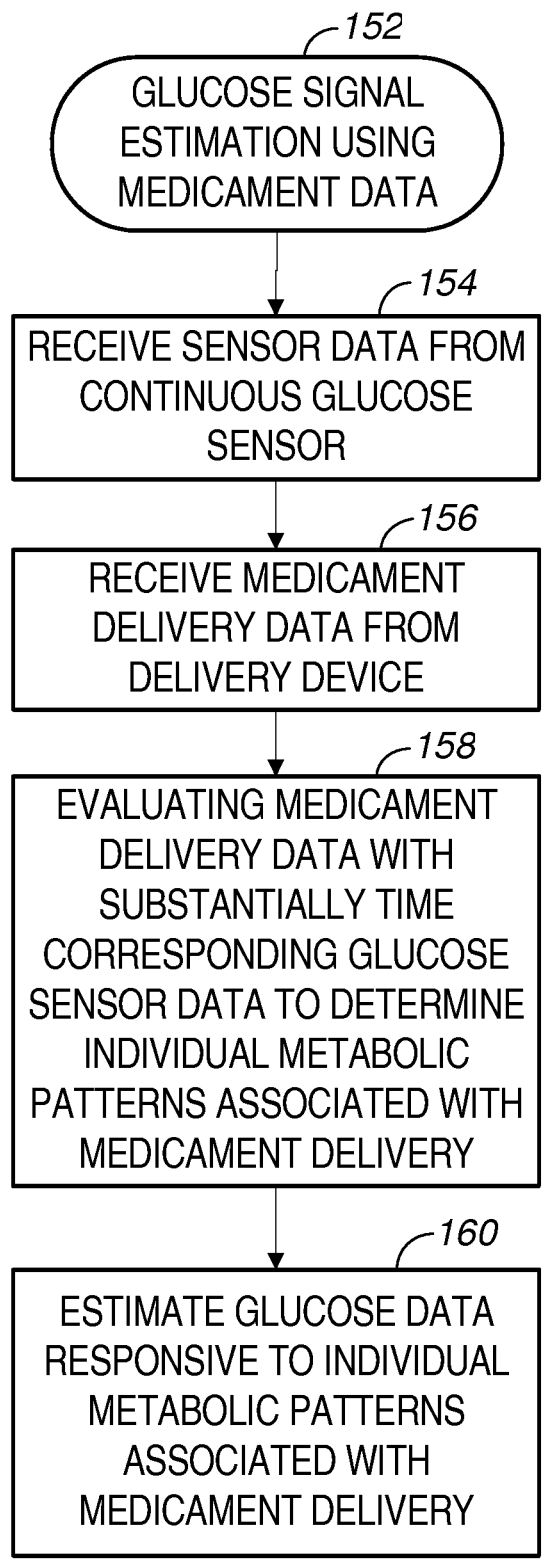
FIG. 11 is a flow chart that illustrates the process of glucose signal estimation using the integrated sensor and medicament delivery device in one embodiment.

The preferred embodiments provide an integrated system, which includes a receiver 14 that receives and processes the raw data stream from the continuous glucose sensor 12. The receiver may perform all or some of the following operations: a calibration, converting sensor data, updating the calibration, evaluating received reference and sensor data, evaluating the calibration for the analyte sensor, validating received reference and sensor data, displaying a meaningful glucose value to a user, calculating therapy recommendations, validating recommended therapy, adaptive programming for learning individual metabolic patterns, and prediction of glucose values, for example. Some complementary systems and methods associated with the receiver are described in more detail with reference to co-pending U.S. patent application Ser. No. 10/633,367, entitled, "SYSTEM AND METHODS FOR PROCESSING ANALYTE SENSOR DATA," which is incorporated herein by reference in its entirety. FIGS. 9 to 11 describe some processes that may be programmed into the receiver. Additionally, the receiver 14 of the preferred embodiments works together with the other components of the system (for example, the medicament delivery device 16 and the single point glucose monitor 18) to provide enhanced functionality, convenience, and safety, such as described in more detail herein. FIGS. 4 to 7 are illustrates of a few exemplary integrated systems of the preferred embodiments, each of which include the receiver, such as described in more detail herein.

In some embodiments, the receiver 14 is a PDA- or pager-sized housing 46, for example, and comprises a user interface 48 that has a plurality of buttons 50 and a liquid crystal display (LCD) screen, which may include a backlight. In some embodiments, the receiver may take other forms, for example a computer, server, or other such device capable of receiving and processing the data such as described herein. In some embodiments the user interface may also include a keyboard, a speaker, and a vibrator such as described with reference to FIG. 8. The receiver 46 comprises systems (for example, electronics) necessary to receive, process, and display sensor data from the glucose sensor 12, such as described in more detail with reference to FIG. 8. The receiver 14 processes data from the continuous glucose sensor 12 and additionally processes data associated with at least one of the medicament delivery device 16, single point glucose meter 16, and user 8.

In some embodiments, the receiver 14 is integrally formed with at least one of the medicament delivery device 16, and single point glucose monitor 18. In some embodiments, the receiver 14, medicament delivery device 16 and/or single point glucose monitor 18 are detachably connected, so that one or more of the components can be individually detached and attached at the user's convenience. In some embodiments, the receiver 14, medicament delivery device 16, and/or single point glucose monitor 18 are separate from, detachably connectable to, or integral with each other; and one or more of the components are operably connected through a wired or wireless connection, allowing data transfer and thus integration between the components. In some embodiments, one or more of the components are operably linked as described above, while another one or more components (for example, the syringe or patch) are provided as a physical part of the system for convenience to the user and as a reminder to enter data for manual integration of the component with the system. Some exemplary embodiments are described with reference to FIGS. 4 to 7, however suffice it to say that each of the components of the integrated system may be manually, semi-automatically, or automatically integrated with each other, and each component may be in physical and/or data communication with another component, which may include wireless connection, wired connection (for example, via cables or electrical contacts), or the like.

Medicament Delivery Device

The preferred embodiments provide an integrated system 10, which includes a medicament delivery device 16 for administering a medicament to the patient 8. The integrated medicament delivery device can be designed for bolus injection, continuous injection, inhalation, transdermal absorption, other method for administering medicament, or any combinations thereof. The term medicament includes any substance used in therapy for a patient using the system 10, for example, insulin, glucacon, or derivatives thereof. Published International Application WO 02/43566 describes glucose, glucagon, and vitamins A, C, or D that may be used with the preferred embodiments. U.S. Pat. Nos. 6,051,551 and 6,024,090 describe types of insulin suitable for inhalation that may be used with the preferred embodiments. U.S. Pat. No. 5,234,906, U.S. Pat. No. 6,319,893, and EP 760677 describe various derivatives of glucagon that may be used with the preferred embodiments. U.S. Pat. No. 6,653,332 describes a combination therapy that may be used with the preferred embodiments. U.S. Pat. No. 6,471,689 and WO 81/01794 describe insulin useful for delivery pumps that may be used with the preferred embodiments. U.S. Pat. No. 5,226,895 describes a method of providing more than one type of insulin that may be used with the preferred embodiments. All of the above references are incorporated herein by reference in their entirety and may be useful as the medicament(s) in the preferred embodiments.

Manual Integration

In some embodiments, the medicament delivery device 16 is a manual delivery device, for example a syringe, inhaler, transdermal patch, cell transplantation device, and/or manual pump for manual integration with the receiver. Manual integration includes medicament delivery devices wherein a user (for example, patient or doctor) manually selects the amount, type, and/or time of delivery. In some embodiments, the medicament delivery device 16 is any syringe suitable for injecting a medicament, as is appreciated by one skilled in the art. One example of a syringe suitable for the medicament delivery device of the preferred embodiments is described in U.S. Pat. No. 5,137,511, which is incorporated herein by reference in its entirety.

Figure 4A:
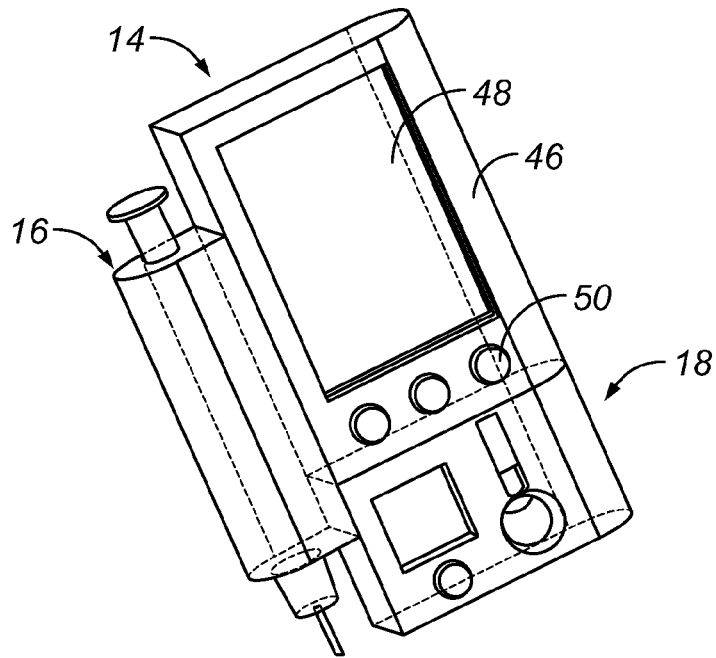
FIGS. 4A and 4B are perspective views of an integrated system 10 in one embodiment, wherein a receiver is integrated with a medicament delivery device in the form of a manual syringe, and optionally includes a single point glucose monitor.
Figure 4B:
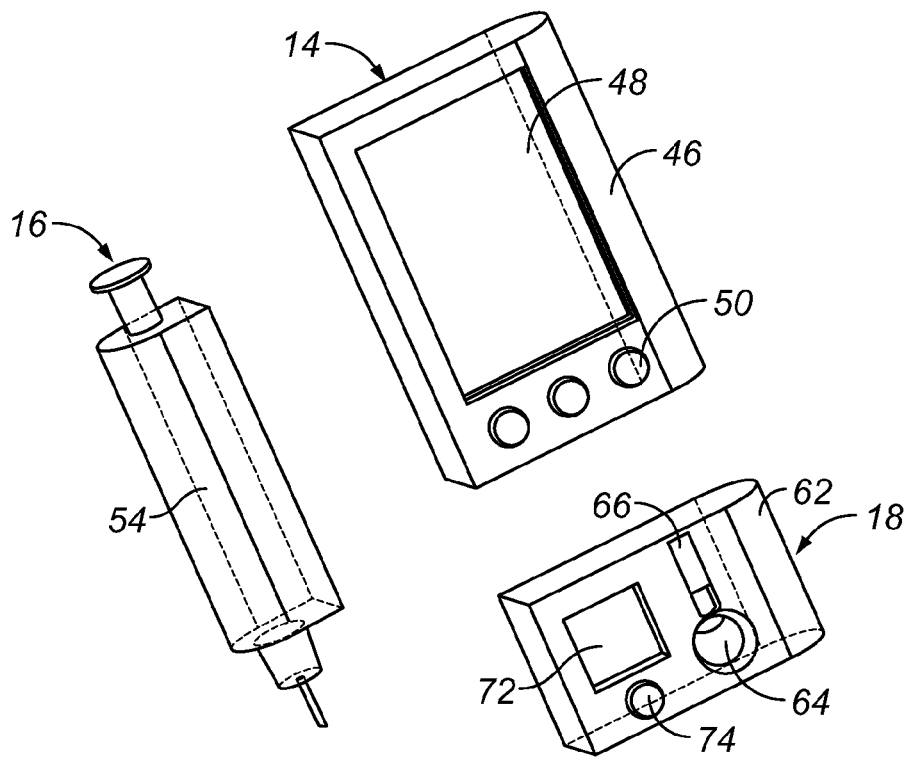

FIGS. 4A and 4B are perspective views of a integrated system 10 in one embodiment, wherein a receiver 14 is integrated with a medicament delivery device 16 in the form of a manual syringe 54, and optionally includes a single point glucose monitor 18, which will be described in more detail elsewhere herein. The receiver 14 receives, processes, and displays data from the continuous glucose monitor 12, such as described in more detail above, and may also receive, process, and display data manually entered by the user. In some embodiments, the receiver includes algorithms that use parameters provided by the continuous glucose sensor, such as glucose concentration, rate-of-change of the glucose concentration, and acceleration of the glucose concentration to more particularly determine the type, amount, and time of medicament administration. The medicament delivery device 16 is in the form of a syringe 54, which may comprise any known syringe configuration, such as described in more detail above. In some embodiments, the syringe 54 includes a housing, which is designed to hold a syringe as well as a plurality of types and amounts of medicament, for example fast-acting insulin, slow-acting insulin, and glucagon. In some embodiments, the syringe is detachably connectable to the receiver 14, and the receiver 14 provides and receives information to and from the patient associated with the time, type, and amount of medicament administered. In some embodiments, the syringe is stored in a holder that is integral with or detachably connected to the receiver 14. In some embodiments, the syringe 54 may be detachable connected directly to the receiver, provided in a kit with the receiver, or other configuration, which provides easy association between the syringe and the receiver.

Referring now to the integration between the syringe and the receiver, it is noted that the receiver can be programmed with information about the time, amount, and types of medicament that may be administered with the syringe, for example. In some embodiments during set-up of the system, the patient and/or doctor manually enters information about the amounts and types of medicament available via the syringe of the integrated system. In some alternative embodiments, manufacturer-provided data can be downloaded to the receiver so that the patient and/or doctor can select appropriate information from menus on the screen, for example, to provide easy and accurate data entry. Thus, by knowing the available medicaments, the receiver may be programmed to customize the patient's therapy recommendations considering available types and amounts of medicaments in combination with concentration, rate-of-change, and/or acceleration of the patient's glucose. While not wishing to be bound by theory, it is believed that by storing available medicament therapies, the receiver is able to customize medicament calculations and recommend appropriate therapy based glucose on trend information and the preferred types and the amounts of medicament available to the patient.

Subsequently in some embodiments, once the patient has administered a medicament (including via the syringe and or by other means), the amount, type, and/or time of medicament administration are input into the receiver by the patient. Similarly, the receiver may be programmed with standard medicaments and dosages for easy selection by the patient (for example, menus on the user interface). This information can be used by the receiver to increase the intelligence of the algorithms used in determining the glucose trends and patterns that may be useful in predicting and analyzing present, past, and future glucose trends, and in providing therapy recommendations, which will be described in more detail below. Additionally, by continuously monitoring the glucose concentration over time, the receiver provides valuable information about how a patient responds to a particular medicament, which information may be used by a doctor, patient, or by the algorithms within the receiver, to determine patterns and provide more personalized therapy recommendations. In other words, in some embodiments, the receiver includes programming that learns the patterns (for example, an individual's metabolic response to certain medicament deliveries and patient behavior) and to determine an optimum time, amount, and type of medicament to delivery in a variety of conditions (e.g., glucose concentration, rate-of-change, and acceleration). While not wishing to be bound by theory, it is believed that by continuously monitoring an individual's response to various medicaments, the patient's glucose levels can be more proactively treated, keeping the diabetic patient within safe glucose ranges substantially all the time.

In some embodiments, the receiver includes programming to predict glucose trends, such as described in co-pending U.S. provisional patent application 60/528,382, entitled, "SIGNAL PROCESSING FOR CONTINUOUS ANALYTE SENSORS", which is incorporated herein by reference in its entirety. In some embodiments, the predictive algorithms consider the amount, type, and time of medicament delivery in predicting glucose values. For example, a predictive algorithm that predicts a glucose value or trend for the upcoming 15 to 20 minutes uses a mathematical algorithm (for example, regression, smoothing, or the like) such as described in the above-cited provisional patent application 60/528,382 to project a glucose value. However outside influences, including medicament delivery may cause this projection to be inaccurate. Therefore, some embodiments provide programming in the receiver that uses the medicament delivery information received from the delivery device 14, in addition to other mathematical equations, to more accurately predict glucose values in the future.

In some alternative embodiments, the medicament delivery device 16 includes one or more transdermal patches 58 suitable for administering medicaments as is appreciated by one skilled in the art. WO 02/43566 describes one such transdermal patch, which may be used in the preferred embodiments. Although the above-cited reference and description associated with the FIGS. 5A to 5C describe a medicament (for example, glucagon) useful for treating hypoglycemia, it is understood that transdermal patches that release a medicament (for example, insulin) useful for treating hyperglycemia are also contemplated within the scope of the preferred embodiments.

FIGS. 5A to 5C are perspective views of an integrated system 10 in one embodiment, wherein a receiver 14 is integrated with a medicament delivery device 16 in the form of one or more transdermal patches 58 housed within a holder 56, and optionally includes a single point glucose monitor 18, which will be described in more detail elsewhere herein. The receiver 14 receives, processes, and displays data from the continuous glucose monitor 12, such as described in more detail above. The medicament delivery device 16 is in the form of one or more transdermal patches 58 held in a holder 56, which may comprise any known patch configuration.

The integration of the patches 58 with the receiver 14 includes similar functionality and provides similar advantages as described with reference to other manual integrations including manual medicament delivery devices (for example, syringe and inhaler). However, a unique advantage may be seen in the integration of a continuous glucose sensor with a glucagon-type patch. Namely, a continuous glucose sensor, such as described in the preferred embodiments, provides more than single point glucose readings. In fact, because the continuous glucose sensor 12 knows the concentration, rate-of-change, acceleration, the amount of insulin administered (in some embodiments), and/or individual patterns associated with a patient's glucose trends (learned over time as described in more detail elsewhere herein), the use of the glucagon patch can be iteratively optimized (inputting its usage into the receiver and monitoring the individual's metabolic response) to proactively preempt hypoglycemic events and maintain a more controlled range of glucose values. This may be particularly advantageous for nighttime hypoglycemia by enabling the diabetic patient (and his/her caretakers) to improve overall nighttime diabetic health. While not wishing to be bound by theory, the integration of the continuous glucose sensor and transdermal glucagon-type patch can provide diabetic patients with a long-term solution to reduce or avoid hypoglycemic events.

In some embodiments, the holder 58 is detachably connectable to the receiver 14 (for example on the side opposite the LCD), which enables convenient availability of the patch to the patient when the receiver indicates that a medicament (for example, glucose or glucagon) is recommended. It is further noted that although this holder is shown without another medicament delivery device 16 in the illustrations of FIGS. 5A to 5C, other medicaments (for example, insulin pen, insulin pump, such as described with reference to FIGS. 6 and 7) may be integrated into the system in combination with the medicament patch illustrated herein. While not wishing to be bound by theory, it is believed that by combining medicaments that aid the diabetic patient in different ways (for example, medicaments for treating hyper- and hypo-glycemic events, or, fast-acting and slow-acting medicaments), a simplified comprehensive solution for treating diabetes may be provided.

Manual Integration of delivery devices with the continuous glucose sensor 12 of the preferred embodiments may additionally be advantageous because the continuous device of the preferred embodiments is able to track glucose levels long-term (for example weeks to months) and adaptively improve therapy decisions based on the patients response over time.

In some alternative embodiments, the medicament delivery device 16 includes an inhaler or spray device suitable for administering a medicament into the circulatory system, as is appreciated by one skilled in the art. Some examples of inhalers suitable for use with the preferred embodiments include U.S. Pat. Nos. 6,167,880, 6,051,551, 6,024,090, which are incorporated herein by reference in their entirety. In some embodiments, the inhaler or spray device is considered a manual medicament delivery device, such as described with reference to FIGS. 4 and 5, wherein the inhaler or spray is manually administered by a patient, and wherein the patient manually enters data into the continuous receiver about the time, amount, and types of therapy. However, it is also possible that the inhaler or spray device used for administering the medicament may also comprise a microprocessor and operable connection to the receiver (for example, RF), such that data is sent and received between the receiver and inhaler or spray device, making it a semi-automated integration, which is described in more detail with reference to the integrated insulin pen below, for example.

In some embodiments, the inhaler or spray device is integrally housed within, detachably connected to, or otherwise physically associated with (for example, in a kit) to the receiver. The functionality and advantages for the integrated inhaler or spray device are similar to those described with reference to the syringe and/or patch integration, above. It is noted that the inhaler or spray device may be provided in combination with any other of the medicament delivery devices of the preferred embodiments, for example, a fast-acting insulin inhaler and a slow acting insulin pump may be advantageously integrated into the system of the preferred embodiments and utilized at the appropriate time as is appreciated by one skilled in the art. In some embodiments, wherein the inhaler or spray device includes a semi-automated integration with the receiver, the inhaler or spray device may by physically integrated with receiver such as described above and also operably connected to the receiver, for example via a wired (for example, via electrical contacts) or wireless (for example, via RF) connection.

In one alternative embodiment, a manual medicament delivery pump is implanted such as described in U.S. Pat. No. 6,283,944, which is incorporated herein by reference in its entirety. In this alternative embodiment, the patient-controlled implantable pump allows the patient to press on the device (through the skin) to administer a bolus injection of a medicament when needed. It is believed that providing glucagon or other medicament for treating hypoglycemia within this device will provide the ease and convenience that can be easily released by the patient and/or his or her caretaker when the continuous glucose sensor indicates severe hypoglycemia, for example. In some alternative embodiments, the manual implantable pump is filled with insulin, or other medicament for treating hyperglycemia. In either case, the manual pump and continuous glucose sensor will benefit from manual integrations described in more detail above.

In another alternative embodiment, a cell transplantation device, such as described in U.S. Pat. Nos. 6,015,572, 5,964,745, and 6,083,523, which are incorporated herein by reference in their entirety, is manually integrated with the continuous sensor of the preferred embodiments. In this alternative embodiment, a patient would be implanted with beta islet cells, which provide insulin secretion responsive to glucose levels in the body. The receiver associated with the implantable glucose sensor can be programmed with information about the cell transplantation (for example, time, amount, type, etc). In this way, the long-term continuous glucose sensor may be used to monitor the body's response to the beta islet cells. This may be particularly advantageous when a patient has been using the continuous glucose sensor for some amount of time prior to the cell transplantation, and the change in the individual's metabolic patterns associated with the transplantation of the cells can be monitored and quantified. Because of the long-term continuous nature of the glucose sensor of the preferred embodiments, the long-term continuous effects of the cell transplantation can be consistently and reliably monitored. This integration may be advantageous to monitor any person's response to cell transplantation before and/or after the implantation of the cells, which may be helpful in providing data to justify the implantation of islet cells in the treatment of diabetes.

It is noted that any of the manual medicament delivery devices can be provided with an RF ID tag or other communication-type device, which allows semi-automated integration with that manual delivery device, such as described in more detail below.

Semi-Automated Integration

Semi-automated integration of medicament delivery devices 16 in the preferred embodiments includes any integration wherein an operable connection between the integrated components aids the user (for example, patient or doctor) in selecting, inputting, or calculating the amount, type, or time of medicament delivery of glucose values, for example, by transmitting data to another component and thereby reducing the amount of user input required. In the preferred embodiments, semi-automated may also refer to a fully automated device (for example, one that does not require user interaction), wherein the fully automated device requires a validation or other user interaction, for example to validate or confirm medicament delivery amounts. In some embodiments, the semi-automated medicament delivery device is an inhaler or spray device, a pen or jet-type injector, or a transdermal or implantable pump.

Figure 6A:
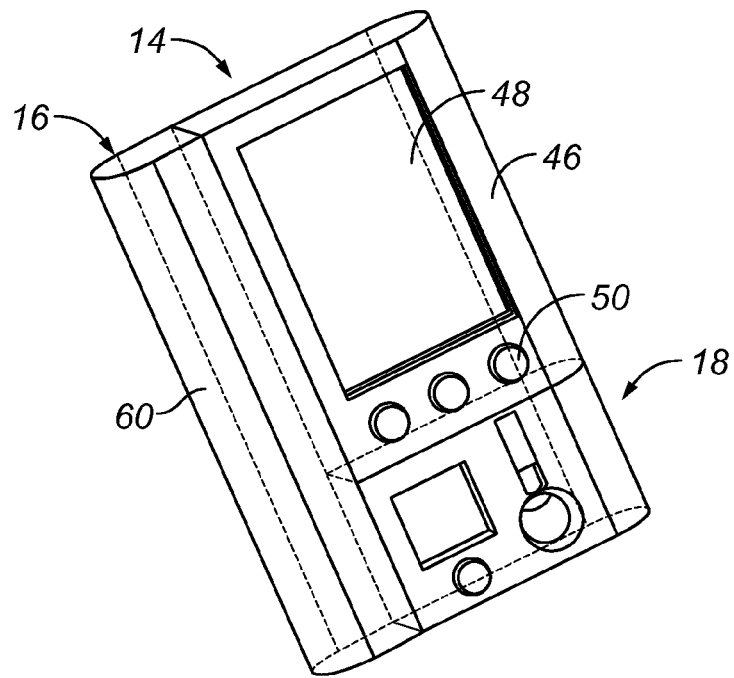
FIGS. 6A and 6B are perspective views of an integrated system in one embodiment, wherein a receiver is integrated with a medicament delivery device in the form of a pen or jet-type injector, and optionally includes a single point glucose monitor.
Figure 6B:
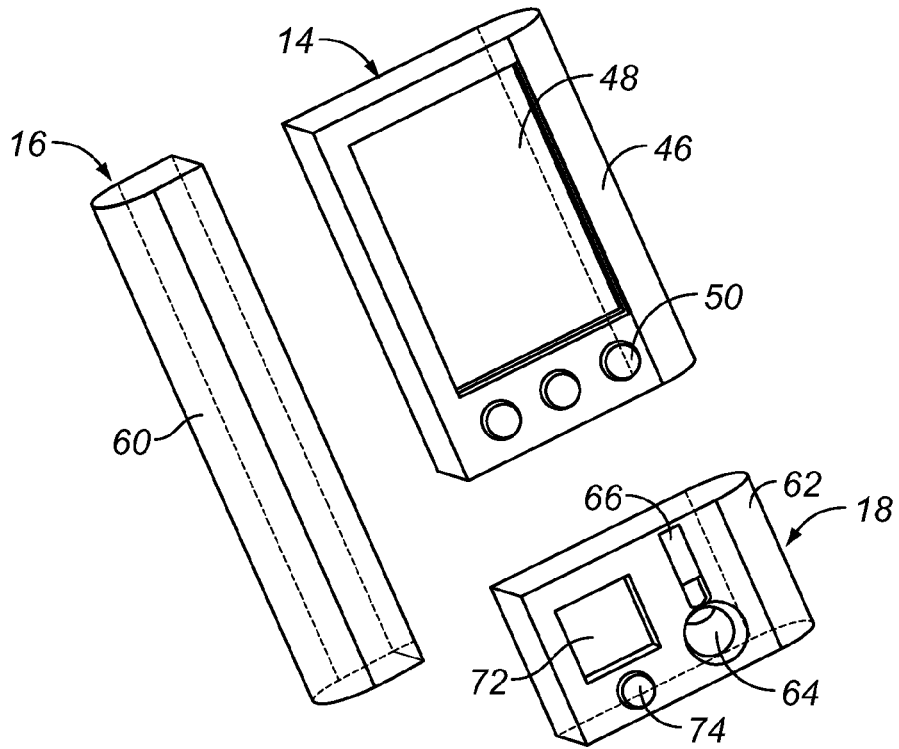

FIGS. 6A and 6B are perspective views of an integrated system 10 in one embodiment, wherein a receiver 14 is integrated with a medicament delivery device 16 in the form of a pen or jet-type injector, hereinafter referred to as a pen 60, and optionally includes a single point glucose monitor 18, which will be described in more detail elsewhere herein. The receiver 14 receives, processes, and displays data from the continuous glucose monitor 12, such as described in more detail above. The medicament delivery pen 60 of the preferred embodiments, includes any pen-type injector, such as is appreciated by one skilled in the art. A few examples of medicament pens that may be used with the preferred embodiments, include U.S. Pat. Nos. 5,226,895, 4,865,591, 6,192,891, and 5,536,249, all of which are incorporated herein by reference in their entirety.

FIG. 6A is a perspective view of an integrated system 10 in embodiment. The integrated system 10 is shown in an attached state, wherein the various elements are held by a mechanical means, as is appreciated by one skilled in the art. The components 14, 16, and 18 (optional) are also in operable connection with each other, which may include a wired or wireless connection. In some embodiments, the components include electrical contacts that operably connect the components together when in the attached state. In some embodiments, the components are operably connected via wireless connection (for example, RF), and wherein the components may or may not be detachably connectable to each other. FIG. 6B show the components in an unattached state, which may be useful when the patient would like to carry minimal components and/or when the components are integrated via a wireless connection, for example.

Medicament delivery pen 60 includes at least a microprocessor and a wired or wireless connection to the receiver 14, which are described in more detail with reference to FIG. 8. In some embodiments, the pen 60 includes programming that receives instructions sent from the receiver 14 regarding type and amount of medicament to administer. In some embodiments, wherein the pen includes more than one type of medicament, the receiver provides the necessary instructions to determine which type or types of medicament to administer, and may provide instructions necessary for mixing the one or more medicaments. In some embodiments, the receiver provides the glucose trend information (for example, concentration, rate-of-change, acceleration, or other user input information) and pen 60 includes programming necessary to determine appropriate medicament delivery.

Subsequently, the pen 60 includes programming to send information regarding the amount, type, and time of medicament delivery to the receiver 14 for processing. The receiver 14 can use this information received from the pen 60, in combination with the continuous glucose data obtained from the sensor, to monitor and determine the patient's glucose patterns to measure their response to each medicament delivery. Knowing the patient's individual response to each type and amount of medicament delivery may be useful in adjusting or optimizing the patient's therapy. It is noted that individual metabolic profiles (for example, insulin sensitivity) are variable from patient to patient. While not wishing to be bound by theory, it is believed that once the receiver has learned (for example, monitored and determined) the individual's metabolic patterns, including glucose trends and associated medicament deliveries, the receiver can be programmed to adjust and optimize the therapy recommendations for the patient's individual physiology to maintain their glucose levels within a desired target range. In alternative embodiments, the pen 60 may be manually integrated with the receiver.

In some embodiments, the receiver includes algorithms that use parameters provided by the continuous glucose sensor, such as glucose concentration, rate-of-change of the glucose concentration, and acceleration of the glucose concentration to more particularly determine the type, amount, and time of medicament administration. In fact, all of the functionality of the above-described manual and semi-automated integrated systems, including therapy recommendations, adaptive programming for learning individual metabolic patterns, and prediction of glucose values, can be applied to the semi-automated integrated system 10, such as described herein. However, the semi-automated integrated sensing and delivery system additionally provides convenience by automation (for example, data transfer through operable connection) and reduced opportunity for human error than may be experienced with the manual integration.

In some alternative embodiments, the semi-automated integration provides programming that requires at least one of the receiver 14, single point glucose monitor 18, and medicament delivery device 16 to be validated or confirmed by another of the components to provide a fail safe accuracy check; in these embodiments, the validation includes algorithms programmed into any one or more of the components. In some alternative embodiments, the semi-automated integration provides programming that requires at least one of the receiver 14 and medicament delivery device 16 to be validated or confirmed by an a human (for example, confirm the amount and/or type of medicament). In these embodiments, validation provides a means by which the receiver can be used adjunctively, when the patient or doctor would like to have more control over the patient's therapy decisions, for example. See FIGS. 9 to 11 for processes that may be implemented herein.

Although the above description of semi-automated medicament delivery is mostly directed to an integrated delivery pen, the same or similar integration can be accomplished between a semi-automated inhaler or spray device, and/or a semi-automated transdermal or implantable pump device. Additionally, any combination of the above semi-automated medicament delivery devices may be combined with other manual and/or automated medicament delivery device within the scope of the preferred embodiments as is appreciated by one skilled in the art.

Automated Integration

Automated integration medicament delivery devices 16 in the preferred embodiments are any delivery devices wherein an operable connection between the integrated components provides for full control of the system without required user interaction. Transdermal and implantable pumps are examples of medicament delivery devices that may be used with the preferred embodiments of the integrated system 10 to provide automated control of the medicament delivery device 16 and continuous glucose sensor 12. Some examples of medicament pumps that may be used with the preferred embodiments include, Patents U.S. Pat. No. 6,471,689, WO 81/01794, and EP 1281351, both of which are incorporated herein by reference in their entirety.

Figure 7A:
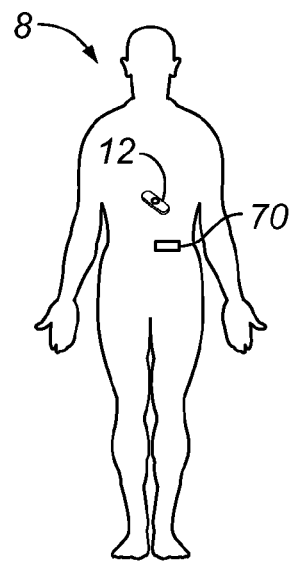
FIGS. 7A to 7C are perspective views of an integrated system in one embodiment, wherein a sensor and delivery pump, which are implanted or transdermally inserted into the patient, are operably connected to an integrated receiver, and optionally include a single point glucose monitor.
Figure 7B:
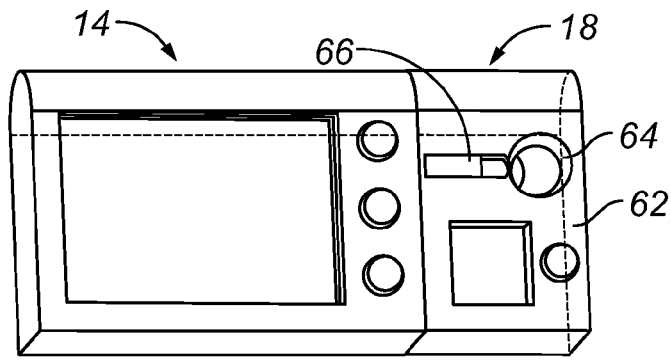
Figure 7C:
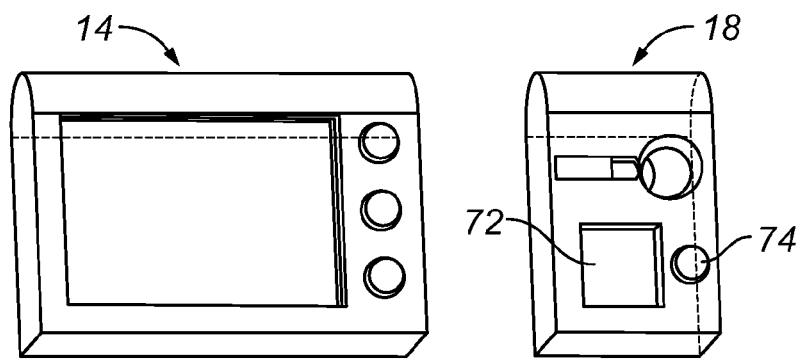

FIGS. 7A to 7C are perspective views of an integrated system in one embodiment, wherein a sensor and delivery pump, which are implanted or transdermally inserted into the patient, are operably connected to an integrated receiver, and optionally include a single point glucose monitor. FIG. 7A is a perspective view of a patient 8, in which is implanted or transdermally inserted a sensor 12 and a pump 70. FIGS. 7B and 7C are perspective views of the integrated receiver and optional single point glucose monitor in attached and unattached states. The pump 70 may be of any configuration known in the art, for example, such as cited above.

The receiver 14 receives, processes, and displays data associated with the continuous glucose monitor 12, data associated with the pump 70, and data manually entered by the patient 8. In some embodiments, the receiver includes algorithms that use parameters provided by the continuous glucose sensor, such as glucose concentration, rate-of-change of the glucose concentration, and acceleration of the glucose concentration to determine the type, amount, and time of medicament administration. In fact, all of the functionality of the above-described manual and semi-automated integrated systems, including therapy recommendations, confirmation or validation of medicament delivery, adaptive programming for learning individual metabolic patterns, and prediction of glucose values, can be applied to the fully automated integrated system 10, such as described herein with reference to FIGS. 7A to 7C. However, the fully automated sensing and delivery system can run with or without user interaction. Published Patent Application US 2003/0028089 provides some systems and methods for providing control of insulin, which may be used with the preferred embodiments, and is incorporated herein by reference in its entirety.

In some embodiments of the automated integrated system 10, a fail-safe mode is provided, wherein the system is programmed with conditions whereby when anomalies or potentially clinically risky situations arise, for example when a reference glucose value (for example, from an SMBG) indicates a discrepancy from the continuous sensor that could cause risk to the patient if incorrect therapy is administered. Another example of a situation that may benefit from a validation includes when a glucose values are showing a trend in a first direction that shows a possibility of "turn around," namely, the patient may be able to reverse the trend with a particular behavior within a few minutes to an hour, for example. In such situations, the automated system may be programmed to revert to a semi-automated system requiring user validation or other user interaction to validate the therapy in view of the situation.

It is noted that in the illustrated embodiment, only one receiver 14 is shown, which houses the electronics for both the medicament delivery pump 70 and the continuous sensor 12. Although it is possible to house the electronics in two different receiver housings, providing one integrated housing 14 increases patient convenience and minimizes confusion or errors. In some embodiments, the sensor receiver electronics and pump electronics are separate, but integrated. In some alternative embodiments, the sensor and pump share the same electronics.

Additionally, the integrated receiver for the sensor and pump, can be further integrated with any combination with the above-described integrated medicament delivery devices, including syringe, patch, inhaler, and pen, as is appreciated by one skilled in the art.

Single Point Glucose Monitor

In the illustrated embodiments (FIGS. 4 to 7), the single point glucose monitor includes a meter for measuring glucose within a biological sample including a sensing region that has a sensing membrane impregnated with an enzyme, similar to the sensing membrane described with reference to U.S. Pat. Nos. 4,994,167 and 4,757,022, which are incorporated herein in their entirety by reference. However, in alternative embodiments, the single point glucose monitor can use other measurement techniques such as optical, for example. It is noted that the meter is optional in that a separate meter can be used and the glucose data downloaded or input by a user into the receiver. However the illustrated embodiments show an integrated system that exploits the advantages associated with integration of the single point glucose monitor with the receiver 14 and delivery device 16.

FIGS. 4 to 7 are perspective views of integrated receivers including a single point glucose monitor. It is noted that the integrated single point glucose monitor may be integral with, detachably connected to, and/or operably connected (wired or wireless) to the receiver 14 and medicament delivery device 16. The single point glucose monitor 18 integrates rapid and accurate measurement of the amount of glucose in a biological fluid and its associated processing with the calibration, validation, other processes associated with the continuous receiver 14, such as described in more detail with reference to co-pending U.S. provisional patent application, 60/523,840, entitled "INTEGRATED RECEIVER FOR CONTINUOUS ANALYTE SENSOR," which is incorporated herein by reference in its entirety.

In the illustrated embodiments, the single point glucose monitor 18, such as described in the above-cited co-pending provisional patent application, 60/523,840, includes a body 62 that houses a sensing region 64, which includes a sensing membrane located within a port. A shuttle mechanism 66 may be provided that preferably feeds a single-use disposable bioprotective film that can be placed over the sensing region 64 to provide protection from contamination. The sensing region includes electrodes, the top ends of which are in contact with an electrolyte phase (not shown), which is a free-flowing fluid phase disposed between the sensing membrane and the electrodes. The sensing region measures glucose in the biological sample in a manner such as described in more detail above, with reference the continuous glucose sensor and/or U.S. Pat. Nos. 4,994,167 and 4,757,022. The similarity of the measurement technologies used for the continuous glucose sensor and the single point glucose sensor provides an internal control that creates increased reliability by nature of consistency and decreased error potential that can otherwise be increased due to combining dissimilar measurement techniques. Additionally, the disclosed membrane system is known to provide longevity, repeatability, and cost effectiveness, for example as compared to single use strips, or the like. However, other single point glucose monitors may be used with the preferred embodiments.

In one alternative embodiment, the single point glucose monitor comprises an integrated lancing and measurement device such as described in U.S. Pat. No. 6,607,658 to Heller et al. In another alternative embodiment, the single point glucose monitor comprises a near infrared device such as described in U.S. Pat. No. 5,068,536 to Rosenthal et al. In another alternative embodiment, the single point glucose monitor comprises a reflectance reading apparatus such as described in U.S. Pat. No. 5,426,032 to Phillips et al. In another alternative embodiment, the single point glucose monitor comprises a spectroscopic transflectance device such as described in U.S. Pat. No. 6,309,884 to Cooper et al. All of the above patents and patent applications are incorporated in their entirety herein by reference.

In some embodiments, the single point glucose meter further comprises a user interface that includes a display 72 and a button 74; however, some embodiments utilize the display 48 and buttons 50 of the receiver 14 rather than providing a separate user interface for the monitor 18. In some embodiments the single point glucose monitor measured glucose concentration, prompts, and/or messages can be displayed on the user interface 48 or 72 to guide the user through the calibration and sample measurement procedures, or the like. In addition, prompts can be displayed to inform the user about necessary maintenance procedures, such as "Replace Sensor" or "Replace Battery." The button 74 preferably initiates the operation and calibration sequences. The button can be used to refresh, calibrate, or otherwise interface with the single point glucose monitor 18 as is appreciated by one skilled in the art.

Integrated Electronics

Figure 8:
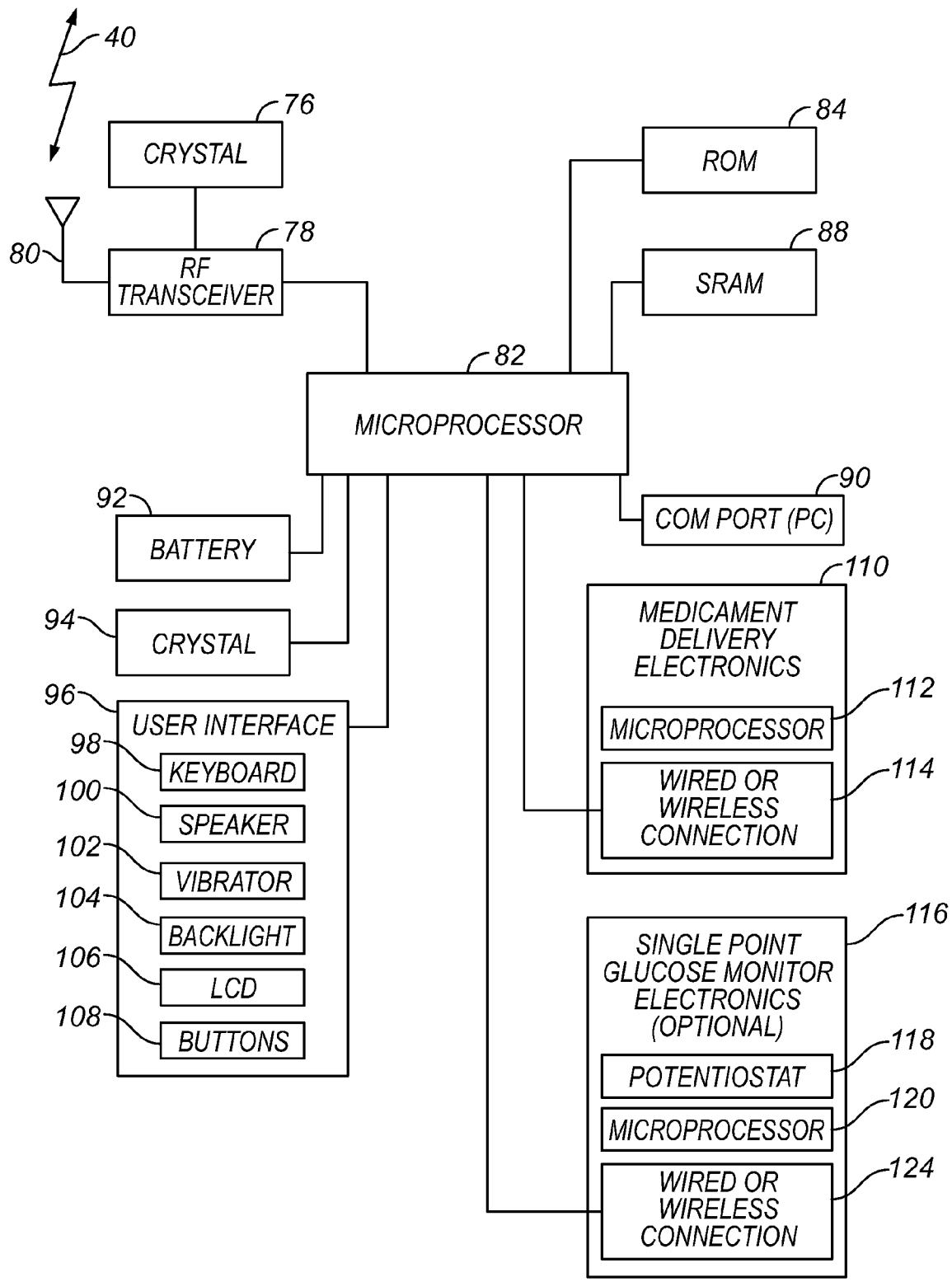
FIG. 8 is a block diagram that illustrates integrated system electronics in one embodiment.

FIG. 8 is a block diagram that illustrates integrated system electronics in one embodiment. One embodiment is described wherein the microprocessor within the receiver performs much of the processing, however it is understood that all or some of the programming and processing described herein can be accomplished within continuous glucose sensor, receiver, single point glucose monitor, and/or delivery device, or any combination thereof. Similarly, displays, alarms, and other user interface functions may be incorporated into any of the individual components of the integrated delivery device.

A quartz crystal 76 is operably connected to an RF transceiver 78 that together function to receive and synchronize data streams via an antenna 80 (for example, transmission 40 from the RF transceiver 44 shown in FIG. 3). Once received, a microprocessor 82 processes the signals, such as described below.

The microprocessor 82 is the central control unit that provides the processing for the receiver, such as storing data, analyzing continuous glucose sensor data stream, analyzing single point glucose values, accuracy checking, checking clinical acceptability, calibrating sensor data, downloading data, recommending therapy instructions, calculating medicament delivery amount, type and time, learning individual metabolic patterns, and controlling the user interface by providing prompts, messages, warnings and alarms, or the like. The ROM 84 is operably connected to the microprocessor 82 and provides semi-permanent storage of data, storing data such as receiver ID and programming to process data streams (for example, programming for performing calibration and other algorithms described elsewhere herein). RAM 88 is used for the system's cache memory and is helpful in data processing. For example, the RAM 88 stores information from the continuous glucose sensor, delivery device, and/or single point glucose monitor for later recall by the user or a doctor; a user or doctor can transcribe the stored information at a later time to determine compliance with the medical regimen or evaluation of glucose response to medication administration (for example, this can be accomplished by downloading the information through the pc com port 90). In addition, the RAM 88 may also store updated program instructions and/or patient specific information. FIGS. 9 and 10 describe more detail about programming that is preferably processed by the microprocessor 82. In some alternative embodiments, memory storage components comparable to ROM and RAM can be used instead of or in addition to the preferred hardware, such as SRAM, EEPROM, dynamic RAM, non-static RAM, rewritable ROMs, flash memory, or the like.

In some embodiments, the microprocessor 82 monitors the continuous glucose sensor data stream 40 to determine a preferable time for capturing glucose concentration values using the single point glucose monitor electronics 116 for calibration of the continuous sensor data stream. For example, when sensor glucose data (for example, observed from the data stream) changes too rapidly, a single point glucose monitor reading may not be sufficiently reliable for calibration during unstable glucose changes in the host; in contrast, when sensor glucose data are relatively stable (for example, relatively low rate of change), a single point glucose monitor reading can be taken for a reliable calibration. In some additional embodiments, the microprocessor can prompt the user via the user interface to obtain a single point glucose value for calibration at predetermined intervals. In some additional embodiments, the user interface can prompt the user to obtain a single point glucose monitor value for calibration based upon certain events, such as meals, exercise, large excursions in glucose levels, faulty or interrupted data readings, or the like. In some embodiments, certain acceptability parameters can be set for reference values received from the single point glucose monitor. For example, in one embodiment, the receiver only accepts reference glucose data between about 40 and about 400 mg/dL.

In some embodiments, the microprocessor 82 monitors the continuous glucose sensor data stream to determine a preferable time for medicament delivery, including type, amount, and time. In some embodiments, the microprocessor is programmed to detect impending clinical risk and may request data input, a reference glucose value from the single point glucose monitor, or the like, in order to confirm a therapy recommendation. In some embodiments, the microprocessor is programmed to process continuous glucose data and medicament therapies to adaptive adjust to an individual's metabolic patterns. In some embodiments, the microprocessor is programmed to project glucose trends based on data from the integrated system (for example, medicament delivery information, user input, or the like). In some embodiments, the microprocessor is programmed to calibrate the continuous glucose sensor based on the integrated single point glucose monitor. Numerous other programming may be incorporated into the microprocessor, as is appreciated by one skilled in the art, as is described in cited patents and patent applications here, and as is described with reference to flowcharts of FIGS. 9 to 11.

It is noted that one advantage of integrated system of the preferred embodiments can be seen in the time stamp of the sensor glucose data, medicament delivery data, and reference glucose data. Namely, typical implementations of the continuous glucose sensor 12, wherein the medicament delivery 16 and/or single point glucose monitor 18 is not integral with the receiver 14, the reference glucose data or medicament delivery data can be obtained at a time that is different from the time that the data is input into the receiver 14. Thus, the user may not accurately input the "time stamp" of the delivery or (for example, the time or obtaining reference glucose value or administering the medicament) at the time of reference data input into the receiver. Therefore, the accuracy of the calibration of the continuous sensor, prediction of glucose values, therapy recommendations, and other processing is subject to human error (for example, due to inconsistencies in entering the actual time of the single point glucose test). In contrast, the preferred embodiments of the integrated system advantageously do no suffer from this potential inaccuracy when the time stamp is automatically and accurately obtained at the time of the event. Additionally, the processes of obtaining reference data and administering the medicament may be simplified and made convenient using the integrated receiver because of fewer loose parts (for example, cable, test strips, etc.) and less required manual data entry.

A battery 92 is operably connected to the microprocessor 82 and provides power for the receiver. In one embodiment, the battery is a standard AAA alkaline battery, however any appropriately sized and powered battery can be used. In some embodiments, a plurality of batteries can be used to power the system. In some embodiments, a power port (not shown) is provided permit recharging of rechargeable batteries. A quartz crystal 94 is operably connected to the microprocessor 168 and maintains system time for the computer system as a whole.

A PC communication (com) port 90 may be provided to enable communication with systems, for example, a serial communications port, allows for communicating with another computer system (for example, PC, PDA, server, or the like). In one exemplary embodiment, the receiver is able to download historical data to a physician's PC for retrospective analysis by the physician. The PC communication port 90 can also be used to interface with other medical devices, for example pacemakers, implanted analyte sensor patches, infusion devices, telemetry devices, or the like.

A user interface 96 comprises a keyboard 98, speaker 100, vibrator 102, backlight 104, liquid crystal display (LCD) 106, and/or one or more buttons 108. The components that comprise the user interface 96 provide controls to interact with the user. The keyboard 98 can allow, for example, input of user information about himself/herself, such as mealtime, exercise, insulin administration, and reference glucose values. The speaker 100 can provide, for example, audible signals or alerts for conditions such as present and/or predicted hyper- and hypoglycemic conditions. The vibrator 102 can provide, for example, tactile signals or alerts for reasons such as described with reference to the speaker, above. The backlight 104 can be provided, for example, to aid the user in reading the LCD in low light conditions. The LCD 106 can be provided, for example, to provide the user with visual data output. In some embodiments, the LCD is a touch-activated screen. The buttons 108 can provide for toggle, menu selection, option selection, mode selection, and reset, for example. In some alternative embodiments, a microphone can be provided to allow for voice-activated control.

The user interface 96, which is operably connected to the microprocessor 82 serves to provide data input and output for both the continuous glucose sensor, delivery mechanism, and/or for the single point glucose monitor.

In some embodiments, prompts or messages can be displayed on the user interface to guide the user through the initial calibration and sample measurement procedures for the single point glucose monitor. Additionally, prompts can be displayed to inform the user about necessary maintenance procedures, such as "Replace Sensing Membrane" or "Replace Battery." Even more, the glucose concentration value measured from the single point glucose monitor can be individually displayed.

In some embodiments, prompts or messages can be displayed on the user interface to convey information to the user, such as malfunction, outlier values, missed data transmissions, or the like, for the continuous glucose sensor. Additionally, prompts can be displayed to guide the user through calibration of the continuous glucose sensor. Even more, calibrated sensor glucose data can be displayed, which is described in more detail with reference co-pending U.S. patent application Ser. No. 10/633,367 and copending U.S. provisional patent application 60/528,382, both of which are incorporated herein by reference in their entirety.

In some embodiments, prompts or messages about the medicament delivery device can be displayed on the user interface to inform or confirm to the user type, amount, and time of medicament delivery. In some embodiments, the user interface provides historical data and analytes pattern information about the medicament delivery, and the patient's metabolic response to that delivery, which may be useful to a patient or doctor in determining the level of effect of various medicaments.

Electronics 110 associated with the delivery device 16 (namely, the semi-automated and automated delivery devices) are operably connected to the microprocessor 82 and include a microprocessor 112 for processing data associated with the delivery device 16 and include at least a wired or wireless connection (for example, RF transceiver) 114 for transmission of data between the microprocessor 82 of the receiver 14 and the microprocessor 112 of the delivery device 16. Other electronics associated with any of the delivery devices cited herein, or other known delivery devices, may be implemented with the delivery device electronics 110 described herein, as is appreciated by one skilled in the art.

In some embodiments, the microprocessor 112 comprises programming for processing the delivery information in combination with the continuous sensor information. In some alternative embodiments, the microprocessor 82 comprises programming for processing the delivery information in combination with the continuous sensor information. In some embodiments, both microprocessors 82 and 112 mutually processor information related to each component.

In some embodiments, the medicament delivery device 16 further includes a user interface (not shown), which may include a display and/or buttons, for example. U.S. Pat. Nos. 6,192,891, 5,536,249, and 6,471,689 describe some examples of incorporation of a user interface into a medicament delivery device, as is appreciated by one skilled in the art.

Electronics 116 associated with the single point glucose monitor 18 are operably connected to the microprocessor 120 and include a potentiostat 118 in one embodiment that measures a current flow produced at the working electrode when a biological sample is placed on the sensing membrane, such as described above. The current is then converted into an analog signal by a current to voltage converter, which can be inverted, level-shifted, and sent to an A/D converter. The microprocessor can set the analog gain via its a control port (not shown). The A/D converter is preferably activated at one-second intervals. The microprocessor looks at the converter output with any number of pattern recognition algorithms known to those skilled in the art until a glucose peak is identified. A timer is then preferably activated for about 30 seconds at the end of which time the difference between the first and last electrode current values is calculated. This difference is then divided by the value stored in the memory during instrument calibration and is then multiplied by the calibration glucose concentration. The glucose value in milligram per deciliter, millimoles per liter, or the like, is then stored in the microprocessor, displayed on the user interface, used to calibrate of the glucose sensor data stream, downloaded, etc.

Programming and Processing (Draw Flow Diagrams)

FIG. 9 is a flow chart that illustrates the process 130 of validating therapy instructions prior to medicament delivery in one embodiment. In some embodiments, the therapy recommendations include a suggestion on the user interface of time, amount, and type of medicament to delivery. In some embodiments, therapy instructions includes calculating a time, amount, and/or type of medicament delivery to administer, and optionally transmitting those instructions to the delivery device. In some embodiments, therapy instructions include that portion of a closed loop system wherein the determination and delivery of medicament is accomplished, as is appreciated by one skilled in the art.

Although computing and processing of data is increasingly complex and reliable, there are circumstances by which the therapy recommendations necessitate human intervention. Some examples include when a user is about to alter his/her metabolic state, for example due to behavior such as exercise, meal, pending manual medicament delivery, or the like. In such examples, the therapy recommendations determined by the programming may not have considered present or upcoming behavior, which may change the recommended therapy. Numerous such circumstances can be contrived, suffice it to say that a validation may be advantageous in order to ensure that therapy recommendations are appropriately administered.

At block 132, a sensor data receiving module, also referred to as the sensor data module, receives sensor data (e.g., a data stream), including one or more time-spaced sensor data points, from a sensor via the receiver, which may be in wired or wireless communication with the sensor. The sensor data point(s) may be raw or smoothed, such as described in co-pending U.S. patent application Ser. No. 10/648,849, entitled "SYSTEMS AND METHODS FOR REPLACING SIGNAL ARTIFACTS IN A GLUCOSE SENSOR DATA STREAM," which is incorporated herein by reference in its entirety.

At block 134, a medicament calculation module, which is a part of a processor module, calculates a recommended medicament therapy based on the received sensor data. A variety of algorithms may be used to calculate a recommended therapy as is appreciated by one skilled in the art.

At block 136, a validation module, which is a part of the processor module, optionally validates the recommended therapy. The validation may include a request from the user, or from another component of the integrated system 10, for additional data to ensure safe and accurate medicament recommendation or delivery. In some embodiments, the validation requests and/or considers additional input, such as time of day, meals, sleep, calories, exercise, sickness, or the like. In some embodiments, the validation module is configured to request this information from the user. In some embodiments, the validation module is responsive to a user inputting such information.

In some embodiments, when the integrated system 10 is in fully automated mode, the validation module is triggered when a potential risk is evaluated. For example, when a clinically risky discrepancy is evaluated, when the acceleration of the glucose value is changing or is low (indicative of a significant change in glucose trend), when it is near a normal meal, exercise or sleep time, when a medicament delivery is expected based on an individual's dosing patterns, and/or a variety of other such situations, wherein outside influences (meal time, exercise, regular medicament delivery, or the like) may deem consideration in the therapy instructions. These conditions for triggering the validation module may be pre-programmed and/or may be learned over time, for example, as the processor module monitors and patterns an individual's behavior patterns.

In some embodiments, when the integrated system 10 is in semi-automated mode, the system may be programmed to request additional information from the user regarding outside influences unknown to the integrated system prior to validation. For example, exercise, food or medicament intake, rest, or the like may input into the receiver for incorporation into a parameter of the programming (algorithms) that processing the therapy recommendations.

At block 138, the receiver confirms and sends (for example, displays, transmits and/or delivers) the therapy recommendations. In manual integrations, the receiver may simply confirm and display the recommended therapy, for example. In semi-automated integrations, the receiver may confirm, transmit, and optionally delivery instructions to the delivery device regarding the recommended therapy, for example. In automated integrations the receiver may confirm and ensure the delivery of the recommended therapy, for example. It is noted that these examples are not meant to be limiting and there are a variety of methods by which the receiver may confirm, display, transmit, and/or deliver the recommended therapy within the scope of the preferred embodiments.

FIG. 10 is a flow chart 140 that illustrates the process of providing adaptive metabolic control using an integrated system in one embodiment. In this embodiment, the integrated system is programmed to learn the patterns of the individual's metabolisms, including metabolic response to medicament delivery.

At block 142, a medicament data receiving module, which may be programmed within the receiver 14 and/or medicament delivery device 16, receives medicament delivery data, including time, amount, and/or type. In some embodiments, the user is prompted to input medicament delivery information into the user interface. In some embodiments, the medicament delivery device 16 sends the medicament delivery data to the medicament data-receiving module.

At block 144, a sensor data receiving module, also referred to as the sensor data module, receives sensor data (e.g., a data stream), including one or more time-spaced sensor data points, from a sensor via the receiver, which may be in wired or wireless communication with the sensor.

At block 146, the processor module, which may be programmed into the receiver 14 and/or the delivery device 16 is programmed to monitor the sensor data from the sensor data module 142 and medicament delivery from the medicament delivery module 144 to determine an individual's metabolic profile, including their response to various times, amounts, and/or types of medicaments. The processor module uses any pattern recognition-type algorithm as is appreciated by one skilled in the art to quantify the individual's metabolic profile.

At block 148, a medicament calculation module, which is a part of a processor module, calculates the recommended medicament based on the sensor glucose data, medicament delivery data, and/or individual's metabolic profile. In some embodiments, the recommended therapy is validated such as described with reference to FIG. 9 above. In some embodiments, the recommended therapy is manually, semi-automatically, or automatically delivered to the patient.

At block 150, the process of monitoring and evaluation a patient's metabolic profile is repeated with new medicament delivery data, wherein the processor monitors the sensor data with the associated medicament delivery data to determine the individual's metabolic response in order to adaptively adjust, if necessary, to newly determined metabolic profile or patterns. This process may be continuous throughout the life of the integrated system, may be initiated based on conditions met by the continuous glucose sensor, may be triggered by a patient or doctor, or may be provided during a start-up or learning phase.

While not wishing to be bound by theory, it is believed that by adaptively adjusting the medicament delivery based on an individual's metabolic profile, including response to medicaments, improved long-term patient care and overall health can be achieved.

FIG. 11 is a flow chart 152 that illustrates the process of glucose signal estimation using the integrated sensor and medicament delivery device in one embodiment. It is noted that glucose estimation and/or prediction are described in co-pending patent application Ser. No. 10/633,367 and provisional patent application 60/528,382, both of which have been incorporated herein by reference in their entirety. However, the preferred embodiments described herein, further incorporated additional data of medicament delivery in estimating or predicting glucose trends.

At block 154, a sensor data receiving module, also referred to as the sensor data module, receives sensor data (e.g., a data stream), including one or more time-spaced sensor data points, from a sensor via the receiver, which may be in wired or wireless communication with the sensor.

At block 156, the medicament data receiving module, which may be programmed within the receiver 14 and/or medicament delivery device 16, receives medicament delivery data, including time, amount, and/or type.

At block 158, the processor module evaluates medicament delivery data with substantially time corresponding glucose sensor data to determine individual metabolic patterns associated with medicament delivery. "Substantially time corresponding data" refers to that time period during which the medicament is delivered and its period of release in the host.

At block 160, the processor module estimates glucose values responsive to individual metabolic patterns associated with the medicament delivery. Namely, the individual metabolic patterns associated with the medicament delivery are incorporated into the algorithms that estimate present and future glucose values, which are believed to increase accuracy of long-term glucose estimation.

EXAMPLES

In one exemplary implementation of the preferred embodiments, the continuous glucose sensor (and its receiver) comprises programming to track a patient during hypoglycemic or near-hypoglycemic conditions. In this implementation, the processor includes programming that sends instructions to administer a hypoglycemic treating medicament, such as glucagon, via an implantable pump or the like, when the glucose level and rate of change surpass a predetermined threshold (for example, 80 mg/dL and 2 mg/dL/min). In this situation, the sensor waits a predetermined amount of time (for example, 40 minutes), while monitoring the glucose level, rate of change of glucose, and/or acceleration/deceleration of glucose in the patient, wherein if the rate of change and/or acceleration shows a changing trend away from hypoglycemia (for example, decreased deceleration of glucose levels to non-hypoglycemia, then the patient need not be alarmed. In this way, the automated glucagon delivery device can proactively preempt hypoglycemic conditions without alerting or awaking the patient.

In another exemplary implementation of the preferred embodiments, a continuous glucose sensor is integrated with a continuous medicament delivery device (for example, an insulin pump) and a bolus medicament delivery device (for example, and insulin pen). In this embodiment, the integration takes exploits the benefits of automated and semi-automated device, for example, providing an automated integration with an infusion pump, while provide semi-automated integration with an insulin pen as necessary.

In yet another exemplary implementation of the preferred embodiments, a medicament delivery device is provided that includes reservoirs of both fast acting insulin and slow acting insulin. The medicament delivery device is integrated with the receiver as described elsewhere herein, however in this implementation, the receiver determines an amount of fast acting insulin and an amount of slow acting insulin, wherein the medicament delivery device is configured to mix slow- and fast-acting insulin in the amounts provided. In this way, the receiver and medicament delivery device can work together in a feedback loop to iteratively optimize amounts of slow and fast acting insulin for a variety of situations (for example, based on glucose level, rate of change, acceleration, and behavioral factors such as diet, exercise, time of day, etc.) adapted to the individual patient's metabolic profile.

In yet another exemplary implementation of the preferred embodiments, an integrated hypo- and hyper-glycemic treating system is provided. In this implementation, a manual-, semi-automated, or automated integration of an insulin delivery device is combined with a manual-, semi-automated, or automated integration of a glucose or glucagon delivery device. These devices are integrated with the receiver for the continuous glucose sensor in any manner described elsewhere herein. While not wishing to be bound by theory, it is believed that the combination of a continuous glucose sensor, integrated insulin device, and integrated glucose or glucagon device provides a simplified, comprehensive, user friendly, convenient, long-term and continuous method of monitoring, treating, and optimizing comprehensive care for diabetes.

Methods and devices that can be suitable for use in conjunction with aspects of the preferred embodiments are disclosed in copending applications including U.S. application Ser. No. 10/695,636 filed Oct. 28, 2003 and entitled, "SILICONE COMPOSITION FOR BIOCOMPATIBLE MEMBRANE"; U.S. patent application Ser. No. 10/648,849 entitled, "SYSTEMS AND METHODS FOR REPLACING SIGNAL ARTIFACTS IN A GLUCOSE SENSOR DATA STREAM," filed Aug. 22, 2003; U.S. patent application Ser. No. 10/646,333 entitled, "OPTIMIZED SENSOR GEOMETRY FOR AN IMPLANTABLE GLUCOSE SENSOR," filed Aug. 22, 2003; U.S. patent application Ser. No. 10/647,065 entitled, "POROUS MEMBRANES FOR USE WITH IMPLANTABLE DEVICES," filed Aug. 22, 2003; U.S. patent application Ser. Nos. 10/633,367, 10/632,537, 10/633,404, and 10/633,329, each entitled, "SYSTEM AND METHODS FOR PROCESSING ANALYTE SENSOR DATA," filed Aug. 1, 2003; U.S. patent application Ser. No. 09/916,386 filed Jul. 27, 2001 and entitled "MEMBRANE FOR USE WITH IMPLANTABLE DEVICES"; U.S. patent application Ser. No. 09/916,711 filed Jul. 27, 2001 and entitled "SENSING REGION FOR USE WITH IMPLANTABLE DEVICE"; U.S. patent application Ser. No. 09/447,227 filed Nov. 22, 1999 and entitled "DEVICE AND METHOD FOR DETERMINING ANALYTE LEVELS"; U.S. patent application Ser. No. 10/153,356 filed May 22, 2002 and entitled "TECHNIQUES TO IMPROVE POLYURETHANE MEMBRANES FOR IMPLANTABLE GLUCOSE SENSORS"; U.S. application Ser. No. 09/489,588 filed Jan. 21, 2000 and entitled "DEVICE AND METHOD FOR DETERMINING ANALYTE LEVELS"; U.S. patent application Ser. No. 09/636,369 filed Aug. 11, 2000 and entitled "SYSTEMS AND METHODS FOR REMOTE MONITORING AND MODULATION OF MEDICAL DEVICES"; and U.S. patent application Ser. No. 09/916,858 filed Jul. 27, 2001 and entitled "DEVICE AND METHOD FOR DETERMINING ANALYTE LEVELS," as well as issued patents including U.S. Pat. No. 6,001,067 issued Dec. 14, 1999 and entitled "DEVICE AND METHOD FOR DETERMINING ANALYTE LEVELS"; U.S. Pat. No. 4,994,167 issued Feb. 19, 1991 and entitled "BIOLOGICAL FLUID MEASURING DEVICE"; and U.S. Pat. No. 4,757,022 filed Jul. 12, 1988 and entitled "BIOLOGICAL FLUID MEASURING DEVICE." All of the above patents and patent applications are incorporated in their entirety herein by reference.

The above description provides several methods and materials of the invention. This invention is susceptible to modifications in the methods and materials, as well as alterations in the fabrication methods and equipment. Such modifications will become apparent to those skilled in the art from a consideration of this application or practice of the invention provided herein. Consequently, it is not intended that this invention be limited to the specific embodiments provided herein, but that it cover all modifications and alternatives coming within the true scope and spirit of the invention as embodied in the attached claims. All patents, applications, and other references cited herein are hereby incorporated by reference in their entirety.

What is claimed is:

1. An integrated diabetes management system for selectively switching between modes of operation, the system comprising:
    a glucose sensor, wherein the glucose sensor is configured to substantially continuously measure glucose concentration in a host for a period exceeding one hour, and to output a data stream, including one or more sensor data points; and
    a processor module operably connected to the glucose sensor, wherein the processor module is configured to receive the data stream, calculate a therapy comprising instructions for administration of a medicament, and send the instructions to a medicament delivery device, wherein the processor module is configured to operate the integrated system in a first mode unless a second mode is triggered, wherein the first mode does not require user interaction to send instructions to the medicament delivery device, wherein the second mode requires user interaction before sending instructions to the medicament delivery device that allow further medicament to be delivered to the user, and wherein the second mode is automatically triggered responsive to a predetermined condition.

2. The integrated system of claim 1, wherein the determination of the predetermined condition is based on an evaluation of information manually inputted by a user into the receiver.

3. The integrated system of claim 1, wherein the determination of the predetermined condition is based on an evaluation by the processor module of input associated with at least one of time of day, meals, sleep, calories, exercise or sickness.

4. The integrated system of claim 1, wherein the predetermined condition is adaptive over time.

5. The integrated system of claim 1, wherein the processor module is configured to learn a behavior pattern of the host, wherein the predetermined condition is a predetermined behavior pattern.

6. The integrated system of claim 5, wherein the predetermined behavior pattern is selected from the group consisting of a medicament delivery time, a meal time, an exercise time and a sleep time.

7. The integrated system of claim 1, wherein the medicament delivery device comprises an insulin delivery device, wherein the insulin delivery device is in the first mode unless the second mode is triggered.

8. An integrated diabetes management system for selectively switching between fully-automated and semi-automated modes, the system comprising:
    a glucose sensor, wherein the glucose sensor is configured to substantially continuously measure glucose concentration in a host for a period exceeding one hour, and to output a data stream, including one or more sensor data points; and
    a processor module operably connected to the glucose sensor, wherein the processor module is configured to receive the data stream, calculate a therapy comprising instructions for administration of a medicament, and send the instructions to a medicament delivery device, wherein the processor module is configured to operate the integrated system in a fully-automated mode unless a semi-automated mode is triggered, wherein the fully automated mode does not require user interaction to send instructions to the medicament delivery device, wherein the semi-automated mode requires user interaction before sending instructions to the medicament delivery device, and wherein the semi-automated mode is automatically triggered responsive to a predetermined condition, wherein the medicament delivery device comprises an insulin delivery device, wherein the insulin delivery device is in the fully automated mode unless the semi-automated mode is triggered, wherein the medicament delivery device further comprises a glucose or glucagon delivery device, wherein the glucose or glucagon delivery device is continuously in a fully automated mode so that user interaction is not required for administration of medicament using the glucose or glucagon delivery device when the insulin delivery device is in the semi-automated mode.

9. A method for selectively switching between operational modes of an integrated diabetes management system, the method comprising:
    generating a data stream from a substantially continuous glucose sensor, the data stream, including one or more sensor data points;
    receiving the data stream, by a processor module;
    calculating a therapy, by the processor module, wherein the therapy comprises instructions for administration of a medicament;
    switching the integrated system from a first mode to a second mode responsive to a predetermined condition being met; and
    sending the instructions for administration of a medicament to a medicament delivery device, wherein the first mode does not require user interaction to send the instructions to the medicament delivery device, and wherein the second mode requires user interaction before sending the instructions to the medicament delivery device that allow further medicament to be delivered to the user.

10. The method of claim 9, wherein determining whether the predetermined condition is met comprises evaluating information manually inputted by a user into the receiver.

11. The method of claim 9, wherein determining whether the predetermined condition is met comprises evaluating input associated with at least one of time of day, meals, sleep, calories, exercise or sickness.

12. The method of claim 9, wherein the predetermined condition is adaptive over time.

13. The method of claim 9, further comprising learning a behavior pattern of the host, wherein the predetermined condition is a predetermined behavior pattern.

14. The method according to 13, wherein the predetermined behavior pattern is selected from the group consisting of a medicament delivery time, a meal time, an exercise time and a sleep time.

15. The method of claim 9, wherein the medicament delivery device comprises an insulin delivery device, wherein the insulin delivery device is in the first mode unless the second mode is triggered.

16. A method for selectively switching between semi-automated and fully-automated modes of an integrated diabetes management system, the method comprising:
    generating a data stream from a substantially continuous glucose sensor, the data stream, including one or more sensor data points;

receiving the data stream, by a processor module;

calculating a therapy, by the processor module, wherein the therapy comprises instructions for administration of a medicament;

switching the integrated system from a fully-automated mode to a semi-automated mode responsive to a predetermined condition being met; and sending the instructions for administration of a medicament to a medicament delivery device, wherein the fully automated mode does not require user interaction to send the instructions to the medicament delivery device, and wherein the semi-automated mode requires user interaction before sending the instructions to the medicament delivery device that allow further medicament to be delivered to the user, wherein the medicament delivery device comprises an insulin delivery device, wherein the insulin delivery device is in the fully automated mode unless the semi-automated mode is triggered, wherein the medicament delivery device further comprises a glucose or glucagon delivery device, wherein the glucose or glucagon delivery device is continuously in a fully-automated mode so that user interaction is not required for administration of medicament using the glucose or glucagon delivery device when the insulin delivery device is in the semi-automated mode.

17. An integrated diabetes management system comprising a computer readable medium stored in memory that is configured to cause a processor to receive a data stream from a substantially continuous glucose sensor, the data stream, including one or more sensor data points, to calculate a therapy comprising instructions for administration of a medicament, and to automatically send the instructions to a medicament delivery device in a first mode unless a second mode is triggered, wherein the first mode does not require user interaction to send instructions to the medicament delivery device, wherein the second mode requires user interaction before sending instructions to the medicament delivery device that allow further medicament to be delivered to the user, and wherein the second mode is triggered responsive to a predetermined condition.

* * * * *

UNITED STATES PATENT AND TRADEMARK OFFICE
CERTIFICATE OF CORRECTION

Page 1 of 4

PATENT NO. : 8,882,741 B2
APPLICATION NO. : 13/460219
DATED : November 11, 2014
INVENTOR(S) : James H. Brauker et al.

It is certified that error appears in the above-identified patent and that said Letters Patent is hereby corrected as shown below:

On the Title Page

In column 2 (page 5, item 56) at line 29, Under Other Publications, change "Measurment:" to --Measurement:--.

In column 2 (page 5, item 56) at line 58, Under Other Publications, change "Effets" to --Effects--.

In column 1 (page 6, item 56) at line 14, Under Other Publications, change "hypoglycaemic" to --hypoglycemic--.

In column 1 (page 6, item 56) at line 65, Under Other Publications, change "systme" to --system--.

In column 2 (page 6, item 56) at line 9, Under Other Publications, change "dynamcs" to --dynamics--.

In column 1 (page 8, item 56) at line 15, Under Other Publications, change "succesfful" to --successful--.

In column 1 (page 8, item 56) at line 38, Under Other Publications, change "artifical" to --artificial--.

In column 1 (page 8, item 56) at line 47, Under Other Publications, change ""xenogenic."" to --"xenogeneic."--.

In column 1 (page 8, item 56) at line 49, Under Other Publications, change "xenogenic." to --xenogeneic.--.

In column 1 (page 8, item 56) at line 53, Under Other Publications, change "Biosens" to --Biosensors &--.

In column 1 (page 8, item 56) at line 69, Under Other Publications, change "Thechnol." to --Technol.--.

Signed and Sealed this
Sixteenth Day of June, 2015

Michelle K. Lee
*Director of the United States Patent and Trademark Office*

CERTIFICATE OF CORRECTION (continued)
U.S. Pat. No. 8,882,741 B2

In column 2 (page 8, item 56) at line 5, Under Other Publications, change "Senso" to --Sensor--.

In column 2 (page 8, item 56) at line 45, Under Other Publications, change "implntable," to --implantable,--.

In column 2 (page 8, item 56) at line 48, Under Other Publications, change "reliablity" to --reliability--.

In column 2 (page 8, item 56) at line 61, Under Other Publications, change "Enzymlology," to --Enzymology,--.

In column 2 (page 8, item 56) at line 70, Under Other Publications, change "artifical" to --artificial--.

In column 1 (page 9, item 56) at line 17, Under Other Publications, change "your and your" to --you and your--.

In column 1 (page 9, item 56) at line 30, Under Other Publications, change "glocuse" to --glucose--.

In column 1 (page 9, item 56) at line 31, Under Other Publications, change "Diabetese" to --Diabetes--.

In column 1 (page 9, item 56) at line 44, Under Other Publications, change "Hypoglycaemia/warning" to --Hypoglycemia/warning--.

In column 1 (page 9, item 56) at line 54, Under Other Publications, change "Thechnol." to --Technol.--.

In column 1 (page 9, item 56) at line 59, Under Other Publications, change "Diabetese" to --Diabetes--.

In column 2 (page 9, item 56) at line 1, Under Other Publications, change "inactiviation" to --inactivation--.

In column 1 (page 10, item 56) at line 13, Under Other Publications, change "Coimmoblized" to --Coimmobilized--.

In column 1 (page 10, item 56) at line 43, Under Other Publications, change "activitiy," to --activity,--.

In column 1 (page 10, item 56) at line 57, Under Other Publications, change "Biosensors& Beioelectronics," to --Biosensors & Bioelectronics,--.

In column 1 (page 10, item 56) at line 58, Under Other Publications, change "glocuse" to --glucose--.

In column 2 (page 10, item 56) at line 10, Under Other Publications, change "Electronanalysis" to --Electroanalysis--.

CERTIFICATE OF CORRECTION (continued)
U.S. Pat. No. 8,882,741 B2

In column 2 (page 10, item 56) at line 26, Under Other Publications, change "artifical" to --artificial--.

In column 2 (page 10, item 56) at line 37, Under Other Publications, change "amperometeric" to --amperometric--.

In column 2 (page 10, item 56) at line 44, Under Other Publications, change "Thechnol." to --Technol.--.

In column 2 (page 10, item 56) at line 55, Under Other Publications, change "Biosens" to --Biosensors &--.

In column 2 (page 10, item 56) at line 67, Under Other Publications, change "On line" to --Online--.

In column 1 (page 11, item 56) at line 11, Under Other Publications, change "termistor" to --thermistor--.

In column 1 (page 11, item 56) at line 12, Under Other Publications, change "metobolites," to --metabolites,--.

In column 1 (page 11, item 56) at line 14, Under Other Publications, change "cholesteral and cholesteral" to --cholesterol and cholesterol--.

In column 1 (page 11, item 56) at line 19, Under Other Publications, change "Apllied" to --Applied--.

In column 1 (page 11, item 56) at line 41, Under Other Publications, change "Biosens" to --Biosensors &--.

In column 1 (page 11, item 56) at line 44, Under Other Publications, change "On line" to --Online--.

In column 2 (page 11, item 56) at line 22, Under Other Publications, change "Subcutaenous" to --Subcutaneous--.

In column 2 (page 11, item 56) at line 32, Under Other Publications, change "assitance" to --assistance--.

In column 2 (page 11, item 56) at line 33, Under Other Publications, change "Thechnol." to --Technol.--.

In column 2 (page 11, item 56) at line 39, Under Other Publications, change "Membran," to --Membrane,--.

In column 1 (page 12, item 56) at line 4, Under Other Publications, change "Thechnol." to --Technol.--.

In column 1 (page 12, item 56) at line 6, Under Other Publications, change "Biosens" to --Biosensors &--.

CERTIFICATE OF CORRECTION (continued)
U.S. Pat. No. 8,882,741 B2

In column 1 (page 12, item 56) at line 21, Under Other Publications, change "Membrance" to --Membrane--.

In column 1 (page 12, item 56) at line 26, Under Other Publications, change "cholesteral" to --cholesterol--.

In column 1 (page 12, item 56) at line 40, Under Other Publications, change "Deabetes" to --Diabetes--.

In column 2 (page 12, item 56) at line 64, Under Other Publications, after "glucose" insert --sensing--.

In the Specification

In column 9 at line 59, Change "and or" to --and/or--.

In column 14 at line 33, Change "glucacon," to --glucagon,--.

In column 15 at line 52, Change "and or" to --and/or--.

In column 18 at line 5, Change "may by" to --may be--.

In column 18 at line 51, Change "RF ID" to --RFID--.

In column 20 at line 31, Change "an a" to --a--.

In column 29 at line 42, Change "(for" to --for--.

In the Claims

In column 32 at line 54, In Claim 14, after "to" insert --claim--.